(12) United States Patent
Wall

(10) Patent No.: US 11,024,422 B2
(45) Date of Patent: *Jun. 1, 2021

(54) ENHANCING DIAGNOSIS OF DISORDER THROUGH ARTIFICIAL INTELLIGENCE AND MOBILE HEALTH TECHNOLOGIES WITHOUT COMPROMISING ACCURACY

(71) Applicant: PRESIDENT AND FELLOWS OF HARVARD COLLEGE, Cambridge, MA (US)

(72) Inventor: Dennis Wall, Brookline, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/930,998

(22) Filed: May 13, 2020

(65) Prior Publication Data
US 2020/0268298 A1    Aug. 27, 2020

Related U.S. Application Data

(63) Continuation of application No. 15/227,656, filed on Aug. 3, 2016, now Pat. No. 10,687,751, which is a
(Continued)

(51) Int. Cl.
*G16H 40/63*    (2018.01)
*G06N 20/00*    (2019.01)
(Continued)

(52) U.S. Cl.
CPC ............ *G16H 40/63* (2018.01); *A61B 5/165* (2013.01); *G06F 8/30* (2013.01); *G06N 20/00* (2019.01);
(Continued)

(58) Field of Classification Search
CPC ........ A61B 5/165; G16H 40/67; G16H 50/20; G16H 10/20; G06N 20/00; G16Z 99/00; G06F 8/30
See application file for complete search history.

(56) References Cited

U.S. PATENT DOCUMENTS 6,569,093 B2    5/2003    Iliff
8,655,817 B2    2/2014    De Bruin et al.
(Continued)

FOREIGN PATENT DOCUMENTS

WO    9705553 A1    2/1997

OTHER PUBLICATIONS

Rutter, Michael, A. Le Couteur, and C. Lord. "Autism diagnostic interview-revised." Los Angeles, CA: Western Psychological Services 29.2003 (2003): 30. (Year: 2003).*
(Continued)

*Primary Examiner* — Eric Nilsson
(74) *Attorney, Agent, or Firm* — Nixon Peabody LLP; Ronald I. Eisenstein; David S. Resnick

(57) ABSTRACT

A computer system for generating a diagnostic tool by applying artificial intelligence to an instrument for diagnosis of a disorder, such as autism. For autism, the instrument can be a caregiver-directed set of questions designed for an autism classification tool or an observation of the subject in a video, video conference, or in person and associated set of questions about behavior that are designed for use in a separate autism classification tool. The computer system can have one or more processors and memory to store one or more computer programs having instructions for generating a highly statistically accurate set of diagnostic items selected from the instrument, which are tested against a first test using a technique using artificial intelligence and a second test against an independent source. Also, a computer imple-
(Continued)

mented method and a non-transitory computer-readable storage medium are disclosed.

20 Claims, 35 Drawing Sheets

Related U.S. Application Data continuation of application No. 14/354,032, filed as application No. PCT/US2012/061422 on Oct. 23, 2012, now Pat. No. 9,443,205.

(60) Provisional application No. 61/682,110, filed on Aug. 10, 2012, provisional application No. 61/567,572, filed on Dec. 6, 2011, provisional application No. 61/550,695, filed on Oct. 24, 2011.

(51) Int. Cl.
| | |
|---|---|
| *G16H 10/20* | (2018.01) |
| *G16H 50/20* | (2018.01) |
| *G16Z 99/00* | (2019.01) |
| *G16H 40/67* | (2018.01) |
| *A61B 5/16* | (2006.01) |
| *G06F 8/30* | (2018.01) |

(52) U.S. Cl.
CPC ............ *G16H 10/20* (2018.01); *G16H 40/67* (2018.01); *G16H 50/20* (2018.01); *G16Z 99/00* (2019.02)

(56) References Cited

U.S. PATENT DOCUMENTS

| | | | |
|---|---|---|---|
| 2001/0034615 | A1 | 10/2001 | Wilkinson et al. |
| 2003/0032069 | A1 | 2/2003 | Muraca |
| 2005/0176057 | A1 | 8/2005 | Bremer et al. |
| 2005/0260549 | A1 | 11/2005 | Feierstein et al. |
| 2006/0282306 | A1 | 12/2006 | Thissen-Roe |
| 2010/0280760 | A1 | 11/2010 | Pi et al. |

OTHER PUBLICATIONS

Artoni, Silvia, et al. "Accessible education for autistic children: ABA-based didactic software." International Conference on Universal Access in Human-Computer Interaction. Springer, Berlin, Heidelberg, Jul. 9, 2011. (Year: 2011).*
Muangnak, Nittaya, Wannapa Pukdee, and Thapani Hengsanunkun. "Classification students with learning disabilities using naive bayes classifier and decision tree." The 6th International Conference on Networked Computing and Advanced Information Management. IEEE, 2010. (Year: 2010).*
Skuse, David, et al. "The developmental, dimensional and diagnostic interview (3di): a novel computerized assessment for autism spectrum disorders." Journal of the American Academy of Child & Adolescent Psychiatry 43.5 (2004): 548-558. (Year: 2004).*
Bailey et al., "Autism as a strongly genetic disorder: evidence from a British twin study", Psychol. Med. 25(1):63-77 (1995).
Bernier et al., "Psychopathology, Families, and Culture: Autism", Child Adolesc Psychiatr Clin N Am 19(4):855-867 (2010).
Berument et al., "Autism screening questionnaire: diagnostic validity", Br J Psychiatry 175:444-51 (1999).
Breiman et al., "Classification and Regression Trees, Chp 6: Medical Diagnosis and Prognosis", Chapman & Hall/ CRC, Boca Raton, FL (1984).
Breiman, "Random Forests", Machine Learning, 45: 5-32 (2001).
Cicchetti et al., "Reliability of the ADI-R: Multiple Examiners Evaluate a Single Case", Autism Dev Disord., 38(4):764-70 (2008).
Cohen, "Fast Effective Rule Induction", Machine Learning: Proceedings of the Twelfth International Conference, 115-123 (1995).

Fischbach et al., "The Simons Simplex Collection: A Resource for Identification of Autism Genetic Risk Factors," Neuron, 68(2):192-195 (2010).
Frank et al., "A simple approach to ordinal prediction", In: European Conference on Machine Learning: Freigburg, Germany, Springer-Verlag, 145-156 (2001).
Frank et al., "Data mining in bioinformatics using Weka", Bioinformatics 20(15):2479-2481 (2004).
Frank et al., "Generating Accurate Rule Sets Without Global Optimization", In: Machine Learning Proceedings of the Fifteenth International Conference: San Francisco, CA, Morgan Kaufmann Publishers (1998).
Freund et al., "A Decision-Theoretic Generalization of On-Line Learning and an Application to Boosting", Journal of Computer and System Sciences, 55: 119-139 (1997).
Freund et al., "Experiments with a new boosting algorithm", In: Proceedings of the International Conference on Machine Learning, San Francisco, pp. 148-156 (1996).
Freund et al., "The alternating decision tree learning algorithm", In: Machine Learning; Proceedings of the Sixteenth International Conference, pp. 124-133 (1999).
Gaines et al., "Induction of Ripple-Down Rules Applied to Modeling Large Databases", J Intell Inf System, 5(3): 211-228 (1995).
Gama, "Functional Trees", Machine Learning, 55: 219-250 (2004).
Geschwind et al., "The Autism Genetic Resource Exchange: A Resource for the Study of Autism and Related Neuropsychiatric Conditions", American Journal of Human Genetics, 69(2): 463-466 (2001).
Gotham et al., "The Autism Diagnostic Observation Schedule: Revised Algorithms for Improved Diagnostic Validity", J.Autism Dev. Disord. 37(4):613-627 (2007).
Gura et al., "Autism spectrum disorder screening in primary care", J. Dev. Behav. Pediatr. 32(1):48-51 (2011).
Hall et al, "The WEKA Data Mining Software: An Update", SIGKDD Explorations, 11(1):10-18 (2009).
Holmes et al., "Multiclass alternating decision trees", ECML, 2430:161-172 (2002).
Holte, "Very Simple Classifcation Rules Perform Well on Most Commonly Used Datasets", Machine Learning: Proceedings of the Sixteenth International Conference, 11: 63-91 (1993).
Howlin, "Children with Autism and Asperger's Syndrome: A Guide for Practitioners and Carers, Chp 3: Identifying and Assesing Children with Autsim or Asperger Syndrome", Chichester, UK, John Wiley and Sons (1998).
Kobak et al., "Web-Based Training in Early Autism Screening: Results from a Pilot Study", Telemedicine and e-Health 17(8):640-644 (2011).
Kohavi, "A Study of Cross-Validation and Bootstrap for Accuracy Estimation and Model Selection", IJCAI 14(2):1137-1145 (1995).
Landwehr et al., "Logistic Model Trees", Machine Learning, 59: 161-205 (2005).
Lord et al., "Autism Diagnostic Interview—Revised: A Revised Version of a Diagnostic Interview for Caregivers of Individuals with Possible Pervasive Developmental Disorders," J. Autism Dev. Disord. 24(5):659-685 (1994).
Lord et al., "Autism Diagnostic Observation Schedule: A Standardized Observation of Communicative and Social Behavior", J. Autism Dev. Disord. 19(2):185-212 (1989).
Lord et al., "The Autism Diagnostic Observation Schedule— Generic: A Standard Measure of Social and Communication Deficits Associated with the Spectrum of Atusim," J. Autism Dev. Disord. 30(3):205-223 (2000).
Martin, "Instance-Based learning: Nearest Neighbor With Generalization", Hamilton, New Zealand: University of Waikato (1995).
Moore et al., "Cached Sufficient Statistics for Efficient Machine Learning with Large Datasets," Journal of Artificial Intelligence 8(3):67-91 (1998).
Pinto-Martin et al., "Screening Strategies for Autism Spectrum Disorders in Pediatric Primary Care", J. Dev. Behav. Pediatr. 29(5):345-350 (2008).
Pisula, "Parents of children with autism: review of current research", Arch. Psychiatry Psychother., 5:51-63 (2003).

(56) References Cited

OTHER PUBLICATIONS

Quinlan, "C.45: Programs for Machine Learning", San Mateo: Morgan Kaufmann Publishers (1993).
Risi et al., "Combining Information from Multiple Sources in the Diagnosis of Autism Spectrum Disorders", Journal of the American Academy of Child and Adolescent Psychiatry, 45(9):1094-1103 (2006).
Robins et al., "The Modified Checklist for Autism in Toddlers: An Initial Study Investigating the Early Detection of Autism and Pervasive Development Disorders", J Autism Dev Disord, 31(2):131-144 (2001).
Santosh et al., "The construction and validation of a short form of the developmental, diagnostic and dimensional interview", Eur. Child Adolesc. Psychiatry 18(8):521-524 (2009).
Shattuck et al., "The Timing of Identification among Children with an Autism Spectrum Disorder: Findings from a Population-Based Surveillance Study", J. Am. Acad. Child Adolesc. Psychiatry 48(5):474-483 (2009).
Shi, Thesis: "Best-first Decision Tree Learning", Hamilton, New Zealand, The University of Waikato (2007). (120 Pages).
Tadevosyan-Leyfer et al., "A Principal Components Analysis of the Autism Diagnostic Interview—Revised", J. Am. Acad. Child Adolesc. Psychiatry 42(7):864-872 (2003).
Wall et al., "Use of Artificial Intelligence to Shorten the Behavioral Diagnosis of Autism," PLOS One 7(8):e43855 (2012).
Wiggins et al., "Examination of the Time Between First Evaluation and First Autism Spectrum Diagnosis in a Population-based Sample", J. Dev. Behav. Pediatr. 27(2):S79-S87 (2006).
Witten et al., "Weka: Practical Machine Learning Tools and Techniques with Java Implementations", University of Waikato, Department of Computer Science (1999). (4 pp).
Wall et al., "Use of machine learning to shorten observation-based screening and diagnosis of austism", Transl Psychiatry, 2:e100 (2012).
Gillberg et al., "Early detection of autism. Diagnostic instruments for clinicians" European Child & Adolescent Psychiatry 5.2 67-74 (1996).
Muangnak et al., "Classification students with learning disabilities using naïve bayes classifier and decision tree", The 7th International Conference on Networked Computing and Advanced Information Management (2010).
Rutter et al., "Autism diagnostic interview—revised" Western Psychological Services 29 (2003).
Skuse, et al., "The developmental, dimensional and diagnostic interview (3di): a novel computerized assessment for autism spectrum disorders", Journal of the American Academy of Child & Adolescent Psychiatry 43.5 548-558 (2004).

* cited by examiner

FIG. 9

Harvard Autism Research Survey

[View] [Edit]

SCIENCE  TUTORIALS  COMMUNITY  ABOUT US

Harvard Autism Research Survey

Welcome and Thank You for participating

We have designed a very short exam of 7 questions, 86 questions fewer (93%) than the most commonly used test, that will help healthcare providers diagnose autism more rapidly and effectively, enabling timely delivery of key therapies that are in step with the development of the child.

...

1. It's Your Choice! Your participation in our research study is completely voluntary.

...

ELECTRONIC CONSENT: Please review our consent document before beginning the survey. Clicking on the "agree" button below indicates that:
- you have read the consent document
- you voluntarily agree to participate
- you are at least 18 years of age
- you are the parent or caregiver of the subject If you do not wish to participate in the research study, please decline participation by clicking on the "disagree" button.

○ Agree    ○ Disagree

---

Administration menu
▲ Administer

Arthur
- My account
- Create content
▲ Feed aggregator
- All Content
- Log out
- Workflow summary

Find us on...
2,114 people like Autworks.

Ann  Bill  Joe  Sara
Peg  Lou  Dan  Kate pubmed: autism and genetics
- The serum level of interleukin-6 in patients with intellectual disability and refractory epilepsy.
- Chromosome 1q21.3 microdeletions comprising BFD and MIR137 are associated with intellectual disability.

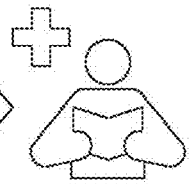
*FIG. 23*

Enter/Edit Patient Information

It's your choice! Your participation in our research study is completely voluntary. You may choose not to participate for any reason and you may withdraw at any time. ELECTRONIC CONSENT: Please review our consent document before beginning the survey. Clicking on the "agree" button below indicates that:

- You have read the consent document
- You voluntarily agree to participate
- You are at least 18 years of age
- You are the parent or caregiver of the subject
- The subject is under 10 years of age If you do not wish to participate in the research study, please decline participation by clicking on the "disagree" button.

○ Agree
○ Disagree

Caregiver/Parent Information

First name: [            ]
Last name: [            ]

Patient information

First name: [            ]
Last name: [            ]
Date of birth: [January ▼] [1 ▼] [2000 ▼]
Gender:
○ Male

FIG. 32

Upload/Change/View Your Video(s)

We ask for a 2 - 15 minute observational video including the following:

- Caregiver smiles and attempts to get patient's attention by calling their name
- Conversation between caregiver and patient (where applicable to child's abilities)
- Patient plays with a toy (doll, action figures etc.)- some object that may initiate pretend play
- Caregiver plays with a toy along with patient
- Caregiver points to specific out of reach toy/object and asks patient to bring over Select a video file to upload:

[Choose File] No file chosen

Date of video: [January ▾] [1 ▾] [2000 ▾]

*FIG. 33*

*FIG. 34*

Please rate the subject's use of socially-directed vocalization.
○ The subject directs vocalizations to the parent/caregiver in a variety of contexts, including chatting or friendly vocalization, or to express needs or interests.
○ The subject directs vocalizations to the parent/caregiver in one context, OR directs vocalizations to the parent/caregiver infrequently across a variety of contexts.
○ The subject directs an occasional vocalization to the parent/caregiver inconsistently in a limited number of contexts; may include whining or crying due to frustration.
○ Vocalizations almost never appear to be directed to the parent/caregiver, or the subject rarely or never vocalizes.
○ N/A - The video does not provide sufficient information to answer this question.

Does the subject exhibit unusual eye contact? If the child is shy initially, and his/her gaze changes markedly and consistently as he/she feels more comfortable, do not include earlier impressions.
○ Appropriate gaze with subtle changes meshed with other communication.

*FIG. 35*

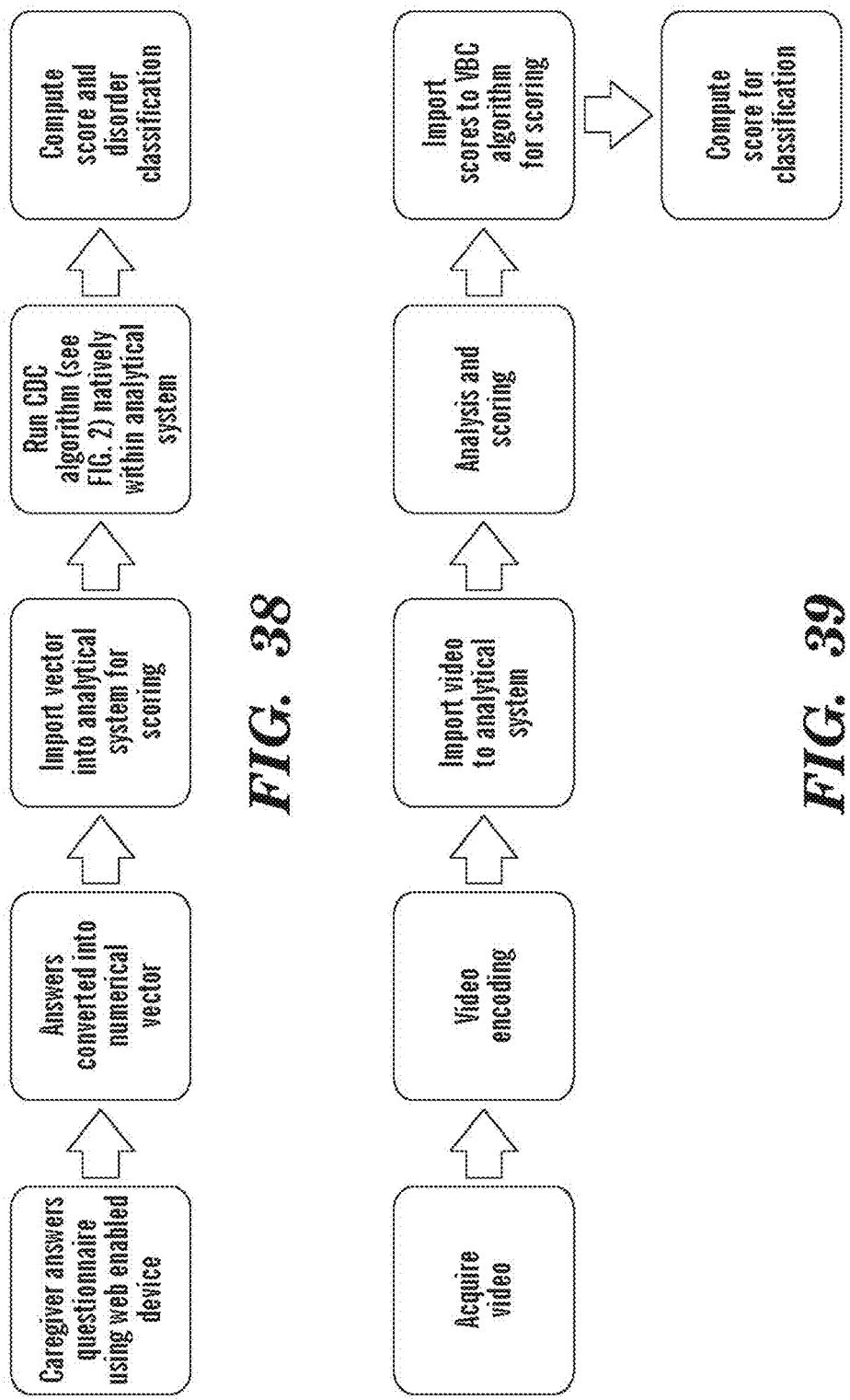

ENHANCING DIAGNOSIS OF DISORDER THROUGH ARTIFICIAL INTELLIGENCE AND MOBILE HEALTH TECHNOLOGIES WITHOUT COMPROMISING ACCURACY

CROSS-REFERENCE TO RELATED APPLICATIONS

This application is a continuation application of co-pending U.S. patent application Ser. No. 15/227,656 filed Aug. 3, 2016, which is a continuation application of application Ser. No. 14/354,032 filed Apr. 24, 2014, which is a 35 U.S.C. § 371 National Phase Entry Application of International Application No. PCT/US2012/061422 filed Oct. 23, 2012, which designates the U.S., and which claims the benefit of, and priority to, U.S. Provisional Patent Application No. 61/550,695, filed on Oct. 24, 2011, entitled "SHORTENING THE BEHAVIORAL DIAGNOSIS OF AUTISM THROUGH ARTIFICIAL INTELLIGENCE AND MOBILE HEALTH TECHNOLOGIES," the entire disclosure of each application is hereby incorporated herein by reference. Also, this application claims the benefit of, and priority to, U.S. Provisional Patent Application No. 61/567,572, filed on Dec. 6, 2011, entitled "Diagnosis of Autism with Reduced Testing," the entire disclosure of which is hereby incorporated herein by reference. This application claims priority to U.S. Provisional Patent Application No. 61/682,110, filed on Aug. 10, 2012, entitled "ENHANCING DIAGNOSIS OF DISORDER THROUGH ARTIFICIAL INTELLIGENCE AND MOBILE HEALTH TECHNOLOGIES WITHOUT COMPROMISING ACCURACY," the entire disclosure of which is hereby incorporated herein by reference.

TECHNICAL FIELD

The present invention relates generally to a method, system, non-transitory computer-readable medium and apparatus for diagnosis of an illness or disorder. Specifically, in one embodiment, a mobile (e.g., web, smart device or the like) tool that enables rapid video-based screening of children for risk of having an autism spectrum disorder is disclosed. The tool is designed to speed the process of diagnosis and increase coverage of the population.

SUMMARY OF THE INVENTION

When a caregiver, such as a parent, suspects that a care recipient, such as a child or elderly person, might have an undiagnosed, misdiagnosed, untreated or undertreated disorder, such as an autism spectrum disorder or dementia, it is important that the caregiver obtain a fast, accurate diagnosis. Problems exist in that known methods of assessment and diagnosis of a mental disorder are difficult to obtain due to a lack of access to a sufficient facility, the cost of a diagnosis, the time involved in obtaining a diagnosis and differences in a subject's behavior outside of routine conditions, such as differences in behavior exhibited at home versus in a clinical environment.

Autism rates continue to rise with more and more children being referred for autism screening every day. Behavioral exams currently used for diagnosis tend to be long and the diagnosis process as a whole is cumbersome for families. In addition, clinical professionals capable of administering the exams tend to be too few and well above capacity. The average time between initial evaluation and diagnosis for a child living in a large metropolitan area is over one year and approaches 5 years for families living in more remote areas. The delay in diagnosis is not only frustrating for families, but prevents many children from receiving medical attention until they are beyond developmental time periods when targeted behavioral therapy would have had maximal impact. The invention can include a mobile-health technology to reshape the landscape of autism screening and diagnosis in order to provide increasingly earlier recognition of autism for all families, including those in remote areas, thereby enabling rapid delivery of treatment and therapy early, often, and in the time window when it has greatest impact.

Autism spectrum disorders have a relatively high incidence rate in the general population, i.e., 1 in 150 children are affected. Autism is defined by impairments in three core domains: social interaction, language, and restricted range of interests. Autism has a genetic component and is largely diagnosed through observation and analysis behavior. Specifically, there is a defined, strong genetic basis for autism, for example, concordance rates for monozygotic twins are near 90%. Further, a significant male bias has been observed, i.e., 4 males to 1 female.

One known tool for autism diagnosis is the Autism Diagnostic Interview Revised (ADI-R) (Lord, et al., "Autism Diagnostic Interview-Revised: a revised version of a diagnostic interview for caregivers of individuals with possible pervasive developmental disorders," *J Autism Dev Disord*, 1994, 24(5):659-685). ADI-R utilizes a semi-structured, investigator-based interview for caregivers; was originally developed as a research instrument, but clinically useful; is keyed to DSM-IV/ICD-10 Criteria; has high inter-rater reliability; utilizes 93 main questions and numerous sub-elements that sum to over 150 items; and takes about 2.5-3 hours to administer.

Another known tool for autism diagnosis is the Autism Diagnostic Observation Schedule (ADOS) (Lord, et al., "The autism diagnostic observation schedule-generic: a standard measure of social and communication deficits associated with the spectrum of autism," *Journal of Autism and Developmental Disorders*, 2000, 30(3): 205-223). ADOS is an unstructured play assessment, which elicits the child's own initiations. The assessment can include social initiations, play, gestures, requests, eye contact, joint attention, etc. pressed for, observed, and coded by examiner. Using ADOS, an examiner pulls for target behaviors through specific use of toys, activities, and interview questions; and stereotypical behaviors, sensory sensitivities, aberrant behaviors and the like are also observed and coded. ADOS typically requires about 30-60 minutes of observation, followed by about 15 minutes of scoring; utilizes 29 questions, of which 12-14 are used for scoring; and requires about 60-90 minutes for total assessment. For example, the Autism Diagnostic Observational Schedule-Generic (ADOS-G) exam is divided into four modules. Each of the modules is geared towards a specific group of individuals based on their level of language and to ensure coverage for wide variety of behavioral manifestations. Module 1, containing 10 activities and 29 items, is focused on individuals with little or no language and therefore most typical for assessment of younger children.

One problem with known tools for autism diagnosis is that diagnosis is often significantly delayed. The average age of initial diagnosis is 5.7 years; 27% remain undiagnosed at age 8; the average age from initial indication to clinical diagnosis is 13 months; and diagnosis capabilities in rural areas is extremely limited. (Shattuck, et al., "Timing of identification among children with an autism spectrum disorder: findings from a population-based surveillance study," *Journal of the American Academy of Child and Adolescent Psychiatry*, 2009, 48(5):474-483. Wiggins, et al., "Examination of the time between first evaluation and first autism spectrum diagnosis in a population-based sample," *Journal of developmental and behavioral pediatrics*, IDBP 2006, 27(2 Suppl):579-87.)

Another problem with known tools for autism diagnosis is that the known tools often require that the subject and caregiver travel long distances to a clinical facility for diagnosis. As a result, the general population has limited access to appropriate resources for autism diagnosis. For example, in Massachusetts, having a population of about 6.6 million people (U.S. Census Bureau, July 2011), there are less than 10 clinical facilities for diagnosis of autism, or just one clinical facility for diagnosis of autism for every 660, 000 people.

Thus, there is a need for improvements to existing autism diagnosis systems, tools and methods, including alternatives to the existing systems, tools and methods.

According to the present invention, accurate identification of likelihood of a disorder in a subject, which normally involves a time-consuming and resource-intensive process, can be achieved in a matter of minutes.

In one embodiment of the present invention, a test is provided that takes about 7 questions to complete and requires creation and submission of a relatively short home video to a system according to the present invention.

According to the present invention, caregivers are empowered to detect a disorder as early as possible and plan an intervention with therapy as early as possible, which is highly desirable in the treatment of disorders such as autism.

One advantage of the present invention is, for example, facilitating the provision of therapy for a subject as early as possible.

For example, with autism, the average diagnosis age is around 5 years old. An autism diagnosis of a subject at age 5 means that the subject has already passed through critical developmental windows where early behavioral therapy would have had a positive impact.

The present invention may be conducted on-line with no waiting time.

The present invention improves access to a powerful screening tool for a disorder such as autism.

The present invention can be used by nearly anyone, particularly a person having a camera and an internet connection.

The present invention may be used in conjunction with a remotely located team of trained researchers, trained to score a video uploaded by a person utilizing the present invention.

The present invention has a distinct advantage over known methods of diagnosing autism in children in that children are normally more relaxed at home than in a doctor's office or clinical environment. With the present invention, a child may be observed while operating within and behaving within his or her home environment, with their siblings and so on. Using the present invention, trained reviewers are able to see signs of a disorder, such as autism, more easily and more rapidly than with known tools.

The present invention is highly accurate.

Known diagnosis methods for disorders can take several hours to complete. Also, with known methods, a family may have to go to a doctor's office, fill out lengthy forms, and be evaluated throughout the day.

It has been discovered, unexpectedly, that for either of the known autism exams, not all of the measurements (e.g., input to an algorithm, which can be descriptions of observed behavior in the format that the algorithm requires, the answers to questions about observed behaviors in the format that the algorithm requires, observations or questions) are required to produce an accurate diagnosis. Through experimentation according to the invention, autism can be diagnosed at perfect accuracy with as few as 8 of the 29 ADOS-G module 1 items, or as few as 7 out of the 93 ADI-R questions. The required number of measurements can be even lower without significant loss of diagnostic accuracy, both in terms of specificity and sensitivity.

Due to the greatly reduced number of measurements required to make the diagnosis, the diagnosis resulting from the invention can be made with near perfect accuracy on video clips, instead of live or interactive interview with the subject and care provider. In some embodiments, therefore, the video clip includes observation of a subject in a non-clinical environment, such as home. In some embodiments, the patient being video recorded is asked a number of questions that are determined to be suitable for diagnosing autism in the patient by the present disclosure. In one aspect, the video clip is shorter than about 10 minutes. In another aspect, the video clip is between about 2 and 5 minutes long. In certain embodiments, the video clips is recorded and/or displayed on a mobile device, or displayed on a web interface.

As the shortened behavioral instruments can be used both individually and combined with each other or each or both combined for the assessment of short, <10 minute video clips of the subject, either in or out of clinical environments, the entire collection of discoveries according to the invention can be integrated for the creation of a mobile health system for rapid, highly accurate, and comprehensive assessment of a subject using a mobile device or web interface.

The present invention can involve the use of a behavioral instrument for rapid screening of autism using home videos taken on hand-held recorders and smart phones. The behavioral instrument can be administered via the web in less than 5 minutes with accuracy identical to that of the gold-standard instruments used for autism diagnosis today. The analysis results in risk assessment reports that give families an unintimidating and empowering means to understand their child's behavior while also speeding the connection between families and the clinical care facilities that can offer further evaluation and care.

The present invention can include the following: (1) Novel algorithms for screening and risk assessment using 2-5 minute video clips of the subject. (2) Web portal for secure access to risk assessment report. (3) A carefully designed risk report for clinicians that includes a preliminary diagnosis, the video of the subject, recommendations for therapy (e.g., ABA, speech therapy) and detailed summary of scoring. This report is made available via secure access to a clinical care facility prior to clinical workup of the subject. (4) A carefully designed risk report for the care provider that includes a recommendation for follow up, contact details and locations of nearest clinical facilities offering diagnosis and treatment, and a collection of educational materials to browse for more information about the subject's potential condition. (5) A growing video repository and associated behavioral score sheets for use in improving recognition of autism and increasing standardization of autism diagnosis.

The present invention can utilize data mining to improve the diagnosis process. For example, the present invention can utilize data from large repositories such as the Autism Genetic Resource Exchange, the Simons Simplex Collection and the Autism Consortium. The present invention can utilize Retrospective analysis of shore sheets such as ADI-R and ADOS, which have large numbers of participants. The present invention uses objective methods to avoid bias. The present invention can utilize artificial intelligence and machine learning. The present invention utilizes classification of diagnostic questions, tested accuracy of the diagnostic questions and alters the known diagnostic instruments in a manner that maximizes efficiency of the diagnosis with little or no negative affect on the accuracy of the diagnosis.

One aspect of the present invention includes an algorithm for parent/caregiver-directed assessment strategy for diagnosis of autism spectrum disorder.

Another aspect of the present invention includes an algorithm for observation of a subject (individual at or above approximately 13 months of age) and assessment strategy for diagnosis of autism spectrum disorder.

Yet another aspect of the present invention includes a machine learning protocol for analysis of behavioral data that results in improved forms of testing of autism spectrum disorder, and other behaviorally diagnosed disorders including but not limited to ADHD, PTSD, and mild cognitive impairment.

Still another aspect of the present invention includes infrastructure, including a database management system, software, and computing equipment associated with the delivery of algorithms disclosed herein.

Another aspect of the present invention includes a quantitative score for diagnosis of subjects and for placement of subjects on a continuous scale from least extreme or severe, to most extreme or severe. For example, in the case of autism spectrum disorders this scale would range from the most severe form of autism to the most extreme phenotype in a neurotypical population.

Yet another aspect of the present invention includes a repository of quantitative scores valuable for the diagnosis of subjects with autism spectrum disorder, for assessment of confidence in diagnosis of subjects with autism spectrum disorder, and for the stratification of subjects for subsequent analysis including further phenotypic evaluation/categorization as well as genotypic evaluation/categorization.

Still another aspect of the present invention includes user interface technology developed for use on personal computers and smart devices such as iPhones, iPads, iPods, and tablets.

Another aspect of the present invention includes training materials needed for administration of algorithms described above.

Yet another aspect of the present invention includes training materials needed for training professionals in video analysis and scoring for observation-based diagnosis of autism spectrum disorder.

Still another aspect of the present invention includes a proprietary set of criteria for videos to be used in the video-based analysis autism spectrum disorders.

Another aspect of the present invention includes a system for clinical impact report generation that is delivered to health care professionals for further analysis of subjects at risk of autism spectrum disorders.

Yet another aspect of the present invention includes the structure and content of a clinical impact report intended for use by health care professionals for rapid assessment of subjects at risk of autism spectrum disorder.

Still another aspect of the present invention includes a system for embedding the contents from the training materials needed for training professionals in video analysis and scoring for observation-based diagnosis of autism spectrum disorder in a web-framework for restricted access by health care professionals with appropriate access credentials.

Another aspect of the present invention includes a system for generation of a report that is directed to parents and caregivers of subjects tested by algorithms mentioned above.

Yet another aspect of the present invention includes the structure and content of a parent/caregiver report intended for rapid knowledge transfer and for rapid connection between parent/caregiver and clinical services.

Still another aspect of the present invention includes code, software and infrastructure for secure, scalable storage of videos of subjects with neurodevelopmental delays including autism spectrum disorders.

Yet another aspect of the present invention includes code, software, and infrastructure for the secure, scalable management of videos of subjects with neurodevelopmental delays including autism spectrum disorders.

In one aspect, provided herein is a computer implemented method of generating a diagnostic tool by applying artificial intelligence to an instrument for diagnosis of a disorder, wherein the instrument comprises a full set of diagnostic items, the computer implemented method comprising: on a computer system having one or more processors and a memory storing one or more computer programs for execution by the one or more processors, the one or more computer programs including instructions for: testing diagnostic items from the instrument using a technique using artificial intelligence; determining from the testing the most statistically accurate set of diagnostic items from the instrument; selecting a set of the most statistically accurate diagnostic items from the instrument; determining the accuracy of the set of the most statistically accurate diagnostic items from the instrument by testing the set of the most statistically accurate diagnostic items from the instrument against an independent source; and generating the diagnostic tool for diagnosis of the disorder.

In one embodiment of this aspect, the instrument is the Autism Diagnostic Interview-Revised and the disorder is autism, the full set of diagnostic items consists of 153 diagnostic items, and the diagnostic tool consists of 7 diagnostic items.

In another embodiment of this aspect, a time for administering the full set of diagnostic items is about 2.5 hours, and a time for administering the diagnostic tool is less than about an hour.

In another embodiment of this aspect, subjects of the 7 diagnostic items are comprehension of simple language, reciprocal conversation, imaginative play, imaginative play with peers, direct gaze, group play with peers and age when abnormality first evident.

In another embodiment of this aspect, the technique using artificial intelligence is a machine learning technique.

In another embodiment of this aspect, the machine learning technique is one from the group consisting of: ADTree, BFTree, ConjunctiveRule, DecisionStump, Filtered Classifier, J48, J48graft, JRip, LADTree, NNge, OneR, OrdinalClassClassifier, PART, Ridor and SimpleCart.

In another embodiment of this aspect, the machine learning technique is ADTree.

In another embodiment of this aspect, the independent source comprises completed Autism Diagnostic Interview-Revised score sheets from Simons Foundation, Boston Autism Consortium, National Database for Autism Research or The Autism Genetic Research Exchange.

In another embodiment of this aspect, the following types of diagnostic items are removed from the 153 diagnostic items: diagnostic items containing a majority of exception codes indicating that the diagnostic item could not be answered in a desired format, diagnostic items involving special isolated skills and diagnostic items with hand-written answers.

In another embodiment of this aspect, the instrument is the Autism Diagnostic Observation Schedule-Generic and the disorder is autism, the full set of diagnostic items consists of four modules, the first of the four modules consists of 29 diagnostic items, and the diagnostic tool consists of 8 diagnostic items from the first module.

In another embodiment of this aspect, a time for administering the full set of diagnostic items is about 2-4 hours, and a time for administering the diagnostic tool is less than about an hour.

In another embodiment of this aspect, subjects of the 8 diagnostic items are frequency of vocalization directed to others, unusual eye contact, responsive social smile, shared enjoyment in interaction, showing, spontaneous initiation of joint attention, functional play with objects and imagination/creativity.

In another embodiment of this aspect, the technique using artificial intelligence is a machine learning technique.

In another embodiment of this aspect, the machine learning technique is one from the group consisting of: ADTree, BFTree, DecisionStump, FT, J48, J48graft, Jrip, LADTree, LMT, Nnge, OneR, PART, RandomTree, REPTree, Ridor and SimpleCart.

In another embodiment of this aspect, the machine learning technique is ADTree.

In another embodiment of this aspect, the independent source comprises score sheets for the first of the four modules from Boston Autism Consortium or Simons Simplex Collection.

In another embodiment of this aspect, the one or more computer programs further comprise instructions for: training an analyst to review a video of a test subject; and scoring the video using the diagnostic tool.

In another embodiment of this aspect, the one or more computer programs further comprise instructions for: generating a report based on the diagnostic tool, the report comprises a suggested clinical action.

In another embodiment of this aspect, the report further comprises at least one of the following: a link to a video of a test subject; at least one chart depicting results of the diagnostic tool; a list of facilities or clinicians, the facilities or clinicians are capable of performing the suggested clinical action; and a map depicting locations of facilities or clinicians, the facilities or clinicians are capable of performing the suggested clinical action.

In another embodiment of this aspect, the one or more computer programs further comprise instructions for: testing a test subject with the diagnostic tool; and testing the test subject with the full set of diagnostic items if the test subject demonstrates a need for the full set of diagnostic items based on the results of the diagnostic tool.

In another embodiment of this aspect, the one or more computer programs further comprise instructions for: treating a test subject for the disorder.

In another aspect, provided herein is a computer system for generating a diagnostic tool by applying artificial intelligence to an instrument for diagnosis of a disorder, the instrument comprises a full set of diagnostic items, the computer system comprising: one or more processors; and memory to store: one or more computer programs, the one or more computer programs comprising instructions for: generating a highly statistically accurate set of diagnostic items selected from the instrument, the highly statistically accurate set of diagnostic items from the instrument pass a first test using a technique using artificial intelligence and a second test against an independent source.

In another embodiment of this aspect, the instrument is the Autism Diagnostic Interview-Revised and the disorder is autism, a full set of diagnostic items from the Autism Diagnostic Interview-Revised consists of 153 diagnostic items, and the diagnostic tool consists of 7 diagnostic items.

In another embodiment of this aspect, a time for administering the full set of diagnostic items is about 2.5 hours, and a time for administering the diagnostic tool is less than about an hour.

In another embodiment of this aspect, subjects of the 7 diagnostic items are comprehension of simple language, reciprocal conversation, imaginative play, imaginative play with peers, direct gaze, group play with peers and age when abnormality first evident.

In another embodiment of this aspect, the technique using artificial intelligence is a machine learning technique.

In another embodiment of this aspect, the machine learning technique is one from the group consisting of: ADTree, BFTree, ConjunctiveRule, DecisionStump, Filtered Classifier, J48, J48graft, JRip, LADTree, NNge, OneR, OrdinalClassClassifier, PART, Ridor and SimpleCart.

In another embodiment of this aspect, the machine learning technique is ADTree.

In another embodiment of this aspect, the independent source comprises completed Autism Diagnostic Interview-Revised score sheets from Simons Foundation, Boston Autism Consortium, National Database for Autism Research or The Autism Genetic Research Exchange.

In another embodiment of this aspect, the following types of diagnostic items are removed from the 153 diagnostic items: diagnostic items containing a majority of exception codes indicating that the diagnostic item could not be answered in a desired format, diagnostic items involving special isolated skills and diagnostic items with hand-written answers.

In another embodiment of this aspect, the instrument is the Autism Diagnostic Observation Schedule-Generic and the disorder is autism, a full set of diagnostic items consists of four modules, the first of the four modules consists of 29 diagnostic items, and the diagnostic tool consists of 8 diagnostic items from the first module.

In another embodiment of this aspect, a time for administering the full set of diagnostic items is about 2-4 hours, and a time for administering the diagnostic tool is less than about an hour.

In another embodiment of this aspect, subjects of the 8 diagnostic items are frequency of vocalization directed to others, unusual eye contact, responsive social smile, shared enjoyment in interaction, showing, spontaneous initiation of joint attention, functional play with objects and imagination/creativity.

In another embodiment of this aspect, the technique using artificial intelligence is a machine learning technique.

In another embodiment of this aspect, the machine learning technique is one from the group consisting of: ADTree, BFTree, DecisionStump, FT, J48, J48graft, LADTree, LMT, Nnge, OneR, PART, RandomTree, REPTree, Ridor and SimpleCart.

In another embodiment of this aspect, the machine learning technique is ADTree.

In another embodiment of this aspect, the independent source comprises score sheets for the first of the four modules from Boston Autism Consortium or Simons Simplex Collection.

In another embodiment of this aspect, the one or more computer programs further comprise instructions for: training an analyst to review a video of a test subject; and scoring the video using the diagnostic tool.

In another embodiment of this aspect, the one or more computer programs further comprise instructions for: generating a report based on the diagnostic tool, the report comprises a suggested clinical action.

In another embodiment of this aspect, the report further comprises at least one of the following: a link to a video of a test subject; at least one chart depicting results of the diagnostic tool; a list of facilities or clinicians, the facilities or clinicians are capable of performing the suggested clinical action; and a map depicting locations of facilities or clinicians, the facilities or clinicians are capable of performing the suggested clinical action.

In another aspect, provided herein is a non-transitory computer-readable storage medium storing one or more computer programs configured to be executed by one or more processing units at a computer comprising instructions for: testing diagnostic items from the instrument using a technique using artificial intelligence; determining from the testing the most statistically accurate set of diagnostic items from the instrument; selecting a set of the most statistically accurate diagnostic items from the instrument; determining the accuracy of the set of the most statistically accurate diagnostic items from the instrument by testing the set of the most statistically accurate diagnostic items from the instrument against an independent source; and generating the diagnostic tool for diagnosis of the disorder.

In one embodiment of this aspect, the instrument is the Autism Diagnostic Interview-Revised and the disorder is autism, the full set of diagnostic items consists of 153 diagnostic items, and the diagnostic tool consists of 7 diagnostic items.

In another embodiment of this aspect, a time for administering the full set of diagnostic items is about 2.5 hours, and a time for administering the diagnostic tool is less than about an hour.

In another embodiment of this aspect, subjects of the 7 diagnostic items are comprehension of simple language, reciprocal conversation, imaginative play, imaginative play with peers, direct gaze, group play with peers and age when abnormality first evident.

In another embodiment of this aspect, the technique using artificial intelligence is a machine learning technique.

In another embodiment of this aspect, the machine learning technique is one from the group consisting of: ADTree, BFTree, ConjunctiveRule, DecisionStump, Filtered Classifier, J48, J48graft, JRip, LADTree, NNge, OneR, OrdinalClassClassifier, PART, Ridor and SimpleCart.

In another embodiment of this aspect, the machine learning technique is ADTree.

In another embodiment of this aspect, the independent source comprises completed Autism Diagnostic Interview-Revised score sheets from Simons Foundation, Boston Autism Consortium, National Database for Autism Research or The Autism Genetic Research Exchange.

In another embodiment of this aspect, the following types of diagnostic items are removed from the 153 diagnostic items: diagnostic items containing a majority of exception codes indicating that the diagnostic item could not be answered in a desired format, diagnostic items involving special isolated skills and diagnostic items with hand-written answers.

In another embodiment of this aspect, the instrument is the Autism Diagnostic Observation Schedule-Generic and the disorder is autism, the full set of diagnostic items consists of four modules, the first of the four modules consists of 29 diagnostic items, and the diagnostic tool consists of 8 diagnostic items from the first module.

In another embodiment of this aspect, a time for administering the full set of diagnostic items is about 2-4 hours, and a time for administering the diagnostic tool is less than about an hour.

In another embodiment of this aspect, subjects of the 8 diagnostic items are frequency of vocalization directed to others, unusual eye contact, responsive social smile, shared enjoyment in interaction, showing, spontaneous initiation of joint attention, functional play with objects and imagination/creativity.

In another embodiment of this aspect, the technique using artificial intelligence is a machine learning technique.

In another embodiment of this aspect, the machine learning technique is one from the group consisting of: ADTree, BFTree, DecisionStump, FT, J48, J48graft, Jrip, LADTree, LMT, Nnge, OneR, PART, RandomTree, REPTree, Ridor and SimpleCart.

In another embodiment of this aspect, the machine learning technique is ADTree.

In another embodiment of this aspect, the independent source comprises score sheets for the first of the four modules from Boston Autism Consortium or Simons Simplex Collection.

In another embodiment of this aspect, the one or more computer programs further comprise instructions for: training an analyst to review a video of a test subject; and scoring the video using the diagnostic tool.

In another embodiment of this aspect, the one or more computer programs further comprise instructions for: generating a report based on the diagnostic tool, the report comprises a suggested clinical action.

In another embodiment of this aspect, the report further comprises at least one of the following: a link to a video of a test subject; at least one chart depicting results of the diagnostic tool; a list of facilities or clinicians, the facilities or clinicians are capable of performing the suggested clinical action; and a map depicting locations of facilities or clinicians, the facilities or clinicians are capable of performing the suggested clinical action.

In another embodiment of this aspect, the one or more computer programs further comprise instructions for: testing a test subject with the diagnostic tool; and testing the test subject with the full set of diagnostic items if the test subject demonstrates a need for the full set of diagnostic items based on the results of the diagnostic tool.

In another embodiment of this aspect, the one or more computer programs further comprise instructions for: treating a test subject for the disorder.

In another aspect, provided herein is a non-transitory computer-readable storage medium storing one or more computer programs configured to be executed by one or more processing units at a computer comprising instructions for: generating a highly statistically accurate set of diagnostic items selected from the instrument, the highly statistically accurate set of diagnostic items from the instrument pass a first test using a technique using artificial intelligence and a second test against an independent source.

In one embodiment of this aspect, the instrument is the Autism Diagnostic Interview-Revised and the disorder is autism, a full set of diagnostic items from the Autism Diagnostic Interview-Revised consists of 153 diagnostic items, and the diagnostic tool consists of 7 diagnostic items.

In another embodiment of this aspect, a time for administering the full set of diagnostic items is about 2.5 hours, and a time for administering the diagnostic tool is less than about an hour.

In another embodiment of this aspect, subjects of the 7 diagnostic items are comprehension of simple language, reciprocal conversation, imaginative play, imaginative play with peers, direct gaze, group play with peers and age when abnormality first evident.

In another embodiment of this aspect, the technique using artificial intelligence is a machine learning technique.

In another embodiment of this aspect, the machine learning technique is one from the group consisting of: ADTree, BFTree, ConjunctiveRule, DecisionStump, Filtered Classifier, J48, J48graft, JRip, LADTree, NNge, OneR, OrdinalClassClassifier, PART, Ridor and SimpleCart.

In another embodiment of this aspect, the machine learning technique is ADTree.

In another embodiment of this aspect, the independent source comprises completed Autism Diagnostic Interview-Revised score sheets from Simons Foundation, Boston Autism Consortium, National Database for Autism Research or The Autism Genetic Research Exchange.

In another embodiment of this aspect, the following types of diagnostic items are removed from the 153 diagnostic items: diagnostic items containing a majority of exception codes indicating that the diagnostic item could not be answered in a desired format, diagnostic items involving special isolated skills and diagnostic items with hand-written answers.

In another embodiment of this aspect, the instrument is the Autism Diagnostic Observation Schedule-Generic and the disorder is autism, a full set of diagnostic items consists of four modules, the first of the four modules consists of 29 diagnostic items, and the diagnostic tool consists of 8 diagnostic items from the first module.

In another embodiment of this aspect, a time for administering the full set of diagnostic items is about 2-4 hours, and a time for administering the diagnostic tool is less than about an hour.

In another embodiment of this aspect, subjects of the 8 diagnostic items are frequency of vocalization directed to others, unusual eye contact, responsive social smile, shared enjoyment in interaction, showing, spontaneous initiation of joint attention, functional play with objects and imagination/creativity.

In another embodiment of this aspect, the technique using artificial intelligence is a machine learning technique.

In another embodiment of this aspect, the machine learning technique is one from the group consisting of: ADTree, BFTree, DecisionStump, FT, J48, J48graft, Jrip, LADTree, LMT, Nnge, OneR, PART, RandomTree, REPTree, Ridor and SimpleCart.

In another embodiment of this aspect, the machine learning technique is ADTree.

In another embodiment of this aspect, the independent source comprises score sheets for the first of the four modules from Boston Autism Consortium or Simons Simplex Collection.

In another embodiment of this aspect, the one or more computer programs further comprise instructions for: training an analyst to review a video of a test subject; and scoring the video using the diagnostic tool.

In another embodiment of this aspect, the one or more computer programs further comprise instructions for: generating a report based on the diagnostic tool, the report comprises a suggested clinical action.

In another embodiment of this aspect, the report further comprises at least one of the following: a link to a video of a test subject; at least one chart depicting results of the diagnostic tool; a list of facilities or clinicians, the facilities or clinicians are capable of performing the suggested clinical action; and a map depicting locations of facilities or clinicians, the facilities or clinicians are capable of performing the suggested clinical action.

In another aspect, provided herein is a method for diagnosing a disorder, comprising determining whether a subject suffers from the disorder with a multivariate mathematical algorithm taking a plurality of measurements as input, the plurality: (a) comprises a set of specific behaviors and measurements thereof identified after machine learning analysis on the Autism Diagnostic Observation Schedule-Generic (ADOS-G) first module, (b) does not include measurement items based on the "response to name" activity of the ADOS-G first module, or (c) does not include measurement items based on the "response to joint attention" activity of the ADOS-G first module, and the determination is performed by a computer suitably programmed therefor.

In one embodiment of this aspect, the method further comprises taking the plurality of measurements from the subject.

In another embodiment of this aspect, the plurality consists of 8 measurement items selected from the ADOS-G first module.

In another embodiment of this aspect, the plurality does not include measurement items based on the "response to name" activity or the "response to joint attention" activity of the ADOS-G first module.

In another embodiment of this aspect, the plurality consists essentially of measurements items selected from the ADOS-G first module.

In another embodiment of this aspect, the multivariate mathematical algorithm comprises alternating decision tree (ADTree).

In another embodiment of this aspect, the determination achieves a greater than about 95% prediction accuracy.

In another embodiment of this aspect, the determination achieves a greater than 95% specificity and a greater than 95% sensitivity.

In another embodiment of this aspect, the measurement items selected from the ADOS-G first module consist of: Frequency of Vocalization Directed to Others (A2); Unusual Eye Contact (B1); Responsive Social Smile (B2); Shared Enjoyment in Interaction (B5); Showing (B9); Spontaneous Initiation of Joint Attention (B10); Functional Play with Objects (C1); and Imagination/Creativity (C2).

In another aspect, provided herein is a non-transitory computer-readable medium comprising program code for diagnosing a disorder, which program code, when executed, determines whether a subject suffers from the disorder with a multivariate mathematical algorithm taking a plurality of measurements as input, the plurality: (a) comprises a set of specific behaviors and measurements thereof identified after machine learning analysis on the Autism Diagnostic Observation Schedule-Generic (ADOS-G) first module, (b) does not include measurement items based on the "response to name" activity of the ADOS-G first module, or (c) does not include measurement items based on the "response to joint attention" activity of the ADO S-G first module.

In another aspect, provided herein is a custom computing apparatus for diagnosing a disorder, comprising: a processor; a memory coupled to the processor; a storage medium in communication with the memory and the processor, the storage medium containing a set of processor executable instructions that, when executed by the processor configure the custom computing apparatus to determine whether a subject suffers from the disorder with a multivariate mathematical algorithm taking a plurality of measurements as input, the plurality: (a) comprises a set of specific behaviors and measurements thereof identified after machine learning analysis on the Autism Diagnostic Observation Schedule-Generic (ADOS-G) first module, (b) does not include measurement items based on the "response to name" activity of the ADOS-G first module, or (c) does not include measurement items based on the "response to joint attention" activity of the ADOS-G first module.

In another aspect, provided herein is a method for diagnosing a disorder, comprising determining whether a subject suffers from the disorder with a multivariate mathematical algorithm taking a plurality of measurements as input, the plurality comprises a set of questions directed at a parent or other caregiver that are geared towards measurement of specific behaviors learned from machine learning analysis of the Autism Diagnostic Interview-Revised (ADI-R) exam, and the determination is performed by a computer suitably programmed therefor.

In one embodiment of this aspect, the method further comprises taking the plurality of measurements from the subject.

In another embodiment of this aspect, the plurality consists of 7 measurement questions selected from the ADI-R exam.

In another embodiment of this aspect, the plurality consists essentially of measurements questions selected from the ADI-R exam.

In another embodiment of this aspect, the multivariate mathematical algorithm comprises alternating decision tree (ADTree).

In another embodiment of this aspect, the determination achieves a greater than about 95% prediction accuracy.

In another embodiment of this aspect, the determination achieves a greater than 95% specificity and a greater than 95% sensitivity.

In another embodiment of this aspect, the measurement questions selected from the ADI-R exam consist of: Comprehension of simple language: answer most abnormal between 4 and 5 (comps15); Reciprocal conversation (within subject's level of language): answer if ever (when verbal) (conver5); Imaginative play: answer most abnormal between 4 and 5 (plays); Imaginative play with peers: answer most abnormal between 4 and 5 (peerp15); Direct gaze: answer most abnormal between 4 and 5 (gazes); Group play with peers: answer most abnormal between 4 and 5 (grplay5); and Age when abnormality first evident (ageabn).

In another aspect, provided herein is a non-transitory computer-readable medium comprising program code for diagnosing a disorder, which program code, when executed, determines whether a subject suffers from the disorder with a multivariate mathematical algorithm taking a plurality of measurements as input, the plurality a set of questions directed at a parent or other caregiver that are geared towards measurement of specific behaviors learned from machine learning analysis of the Autism Diagnostic Interview-Revised (ADI-R) exam.

In another aspect, provided herein is a custom computing apparatus for diagnosing a disorder, comprising: a processor; a memory coupled to the processor; a storage medium in communication with the memory and the processor, the storage medium containing a set of processor executable instructions that, when executed by the processor configure the custom computing apparatus to determine whether a subject suffers from the disorder with a multivariate mathematical algorithm taking a plurality of measurements as input, the plurality comprises a set of questions directed at a parent or other caregiver that are geared towards measurement of specific behaviors learned from machine learning analysis of the Autism Diagnostic Interview-Revised (ADI-R) exam.

In another aspect, provided herein is a method of diagnosing an autism spectrum disorder in a subject, the method comprising: scoring the subject's behavior; analyzing results of the scoring with a diagnostic tool to generate a final score, wherein the diagnostic tool is generated by applying artificial intelligence to an instrument for diagnosis of the autism spectrum disorder; and providing an indicator as to whether the subject has the autism spectrum disorder based on the final score generated by the analyzing step.

In one embodiment of this aspect, the instrument is a caregiver-directed questionnaire, and wherein the step of scoring the subject's behavior consists of: scoring the subject's understanding of basic language; scoring the subject's use of back-and-forth conversation; scoring the subject's level of imaginative or pretend play; scoring the subject's level of imaginative or pretend play with peers; scoring the subject's use of eye contact; scoring the subject's behavior in peer groups; and scoring the subject's age when abnormality first recognized.

In another embodiment of this aspect, the subject's understanding of basic language is scored on a scale from 0 to 8, wherein the score of 0 corresponds with a subject who in response to a request can place an object, other than something to be used by himself/herself, in a new location in a different room, wherein the score of 1 corresponds with a subject who in response to a request can usually get an object, other than something for herself/himself from a different room, but usually cannot perform a new task with the object such as put it in a new place, wherein the score of 2 corresponds with a subject who understands more than 50 words, including names of friends and family, names of action figures and dolls, names of food items, but does not meet criteria for the previous two answers, wherein the score of 3 corresponds with a subject who understands fewer than 50 words, but some comprehension of "yes" and "no" and names of a favorite objects, foods, people, and also words within daily routines, wherein the score of 4 corresponds with a subject who has little or no understanding of words, and wherein the score of 8 corresponds with a subject whose understanding of basic language is not applicable.

In another embodiment of this aspect, the subject's back-and-forth conversation is scored on a scale from 0 to 8, wherein the score of 1 corresponds with a subject for whom conversation flows, with the subject and another person both contributing to an ongoing dialogue, wherein the score of 2 corresponds with a subject who exhibits occasional back-and-forth conversation, but limited in flexibility or topics, wherein the score of 3 corresponds with a subject who exhibits little or no back-and-forth conversation, wherein the subject has difficulty building a conversation, wherein the subject fails to follow a conversation topic, and wherein the subject may ask or answer questions but not as part of a dialogue, wherein the score of 4 corresponds with a subject who rarely speaks or initiates conversation, and wherein the score of 8 corresponds with a subject for whom level of back-and-forth conversation is not applicable or cannot be scored.

In another embodiment of this aspect, the subject's level of imaginative or pretend play is scored on a scale from 0 to 8, wherein the score of 0 corresponds with a subject exhibiting a variety of imagination and pretend play, including use of toys to engage in play activity, wherein the score of 1 corresponds with a subject exhibiting some imagination and pretend play, including pretending with toys, but limited in variety or frequency, wherein the score of 2 corresponds with a subject exhibiting occasional pretending or highly repetitive pretend play, or only play that has been taught by others, wherein the score of 3 corresponds with a subject showing no pretend play, and wherein the score of 8 corresponds with a subject whose level of imaginative or pretend play is not applicable.

In another embodiment of this aspect, the subject's level of imaginative or pretend play with peers is scored on a scale from 0 to 8, wherein the score of 0 corresponds with a subject who actively participates in imaginative play with other children in which the subject leads and follows another child in pretend activities, wherein the score of 1 corresponds with a subject who exhibits some participation in pretend play with another child, but not truly back-and-forth, or level of pretending/imagination is limited in variety, wherein the score of 2 corresponds with a subject who exhibits some play with other children, but little or no pretending, wherein the score of 3 corresponds with a subject who engages in no play with other children or no pretend play when alone, and wherein the score of 8 corresponds with the subject's level of imaginative or pretend play with peers is not applicable.

In another embodiment of this aspect, the subject's use of eye contact is scored on a scale from 0 to 8, wherein the score of 0 corresponds with a subject for whom normal eye contact is used to communicate across a range of situations and people, wherein the score of 1 corresponds with a subject who makes normal eye contact, but briefly or inconsistently during social interactions, wherein the score of 2 corresponds with a subject who makes uncertain/occasional direct eye contact, or eye contact rarely used during social interactions, wherein the score of 3 corresponds with a subject who exhibits unusual or odd use of eye contact, and wherein the score of 8 correspond with a subject whose use of eye contact is not applicable or scorable.

In another embodiment of this aspect, the subject's level of play behavior in peer groups is scored on a scale from 0 to 8, wherein the score of 0 corresponds with a subject who actively seeks and plays together with peers in several different groups in a variety of activities or situations, wherein the score of 1 corresponds with a subject who exhibits some play with peers, but tends not to initiate, or tends to be inflexible in the games played, wherein the score of 2 corresponds with a subject who enjoys parallel active play, but little or no cooperative play, wherein the score of 3 corresponds with a subject who seeks no play that involves participation in groups of other children, though may chase or play catch, and wherein the score of 8 corresponds with the subject's level of imaginative or pretend play with peers is not applicable.

In another embodiment of this aspect, the subject's age when abnormality first recognized is scored on a scale from 0 to 4, wherein the score of 0 corresponds with a subject for whom development in the first 3 years of life has been or was clearly normal in quality and within normal limits for social, language, and physical milestones, and wherein the subject exhibits no behavioral problems that might indicate developmental delay, wherein the score of 1 corresponds with a subject for whom development is potentially normal during first 3 years, but uncertainty because of some differences in behavior or level of skills in comparison to children of the same age, wherein the score of 2 corresponds with a subject for whom development has been or was probably abnormal by or before the age of 3 years, as indicated by developmental delay, but milder and not a significant departure from normal development, wherein the score of 3 indicates that development has been or was clearly abnormal during the first 3 years, but not obvious as autism, and wherein the score of 4 indicates that the subject's development has been or was clearly abnormal during the first 3 years and quality of behavior, social relationships, and communications appear to match behaviors consistent with autism.

In another embodiment of this aspect, the instrument is a set of questions that correspond to an observation of the subject in a video, video conference or in person, and wherein the step of scoring the subject's behavior consists of: scoring the subject's tendency to direct sounds, words or other vocalizations to others; scoring the subject's use of eye contact; scoring the subject's tendency to smile in response to social queues; scoring the subject's shared enjoyment in interaction; scoring the subject's tendency to show objects to another person; scoring the subject's tendency to initiate joint attention; scoring the subject's level of appropriate play with toys or other objects; and scoring the subject's level of imagination/creativity.

In another embodiment of this aspect, the subject's tendency to direct sounds, words or other vocalizations to others is scored on a scale from 0 to 8, wherein the score of 0 corresponds with a subject who directs sounds, words or other vocalizations to a caregiver or to other individuals in a variety of contexts and who chats or uses sounds to be friendly, express interest, and/or to make needs known, wherein the score of 1 corresponds with a subject who directs sounds, words or other vocalizations to a caregiver or to other individuals regularly in one context, or directs vocalizations to caregiver or other individuals irregularly across a variety of situations/contexts, wherein the score of 2 corresponds with a subject who occasionally vocalizes to a caregiver or other individuals inconsistently in a limited number of contexts, possibly including whining or crying due to frustration, wherein the score of 3 corresponds with a subject who almost never vocalizes or vocalizations never appear to be directed to caregiver or other individuals in the observation of the subject in a video, video conference or in person, and wherein the score of 8 corresponds with a subject whose tendency to direct sounds, words or other vocalizations to others is not applicable.

In another embodiment of this aspect, the subject's use of eye contact is scored on a scale from 0 to 8, wherein the score of 0 corresponds with a subject who makes normal eye contact, wherein the score of 2 corresponds with a subject who has some irregular or unusual use of eye contact to initiate, terminate, or regulate social interaction, and wherein the score of 8 corresponds with a subject whose use of eye contact is not applicable or scorable.

In another embodiment of this aspect, the subject's tendency to smile in response to social queues is scored on a scale from 0 to 8, wherein the score of 0 corresponds with a subject who smiles immediately in response to smiles by the caregiver or other individuals in the observation of the subject in a video, video conference or in person and with a subject who can switch from not smiling to smiling without being asked to smile, wherein the score of 1 corresponds with a subject who delays, only smiles partially, smiles only after repeated smiles by caregiver or other individuals in the observation of the subject in a video, video conference or in person, or smiles only when asked, wherein the score of 2 corresponds with a subject who smiles fully or partially at the caregiver or other individuals only after being tickled, or only after being prompted by repeated attempts which may include using a toy or other object, wherein the score of 3 corresponds with a subject who does not smile in response to another person, and wherein the score of 8 corresponds with a subject whose tendency to smile in response to social queues is not applicable or cannot be scored.

In another embodiment of this aspect, the subject's shared enjoyment in interaction is scored on a scale from 0 to 8, wherein the score of 0 corresponds with a subject who shows clear and appropriate happiness with the caregiver or other individuals during two or more activities, wherein the score of 1 corresponds with a subject who shows somewhat inconsistent signs of happiness with the caregiver or other individuals during more than one activity, or only shows signs of happiness with the caregiver or others involved during one interaction, wherein the score of 2 corresponds with a subject who shows little or no signs of happiness in interaction with the caregiver or others in the observation of the subject in a video, video conference or in person although may exhibit signs of happiness when playing alone, wherein the score of 8 corresponds with a subject whose shared enjoyment in interaction is not applicable or cannot be scored.

In another embodiment of this aspect, the subject's tendency to show objects to another person is scored on a scale from 0 to 8, wherein the score of 0 corresponds with a subject who spontaneously shows toys or objects at various times during the observation of the subject in a video, video conference or in person by holding them up or putting them in front of others and using eye contact with or without vocalization, wherein the score of 1 corresponds with a subject who shows toys or objects partially or inconsistently, wherein the score of 2 corresponds with a subject who does not show objects to another person, and wherein the score of 8 corresponds with a subject whose tendency to show objects to another person is not applicable or cannot be evaluated.

In another embodiment of this aspect, the subject's tendency to initiate joint attention is scored on a scale from 0 to 2, wherein the score of 0 corresponds with a subject who uses normal eye contact to reference an object that is out of reach by looking back-and-forth between the caregiver or other person and the object, wherein eye contact may be used with pointing and/or vocalization, wherein the score of 1 corresponds with a subject who partially references an object that is out of reach, wherein the subject may spontaneously look and point to the object and/or vocalize, but does not use eye contact to get the attention of another person and then look at or point to the examiner or the parent/caregiver, but not look back at the object, and wherein the score of 2 corresponds with a subject that does not attempt to try to get another person's attention to reference an object that is out of reach.

In another embodiment of this aspect, the subject's level of appropriate play with toys or other objects is scored on a scale from 0 to 8, wherein the score of 0 corresponds with a subject who independently plays with a variety of toys in a conventional manner, including appropriate play with action figures or dolls, wherein the score of 1 corresponds with a subject who plays appropriately with some toys but not always, wherein the score of 2 corresponds with a subject who plays with only one toy or one type of toy despite there being others around to play with, or only imitates others when playing with a toy, wherein the score of 3 corresponds with a subject who does not play with toys or plays with toys in an inappropriate, stereotyped, or repetitive way, and wherein the score of 8 corresponds with a subject whose level of appropriate play with toys or other objects is not applicable or cannot be scored.

In another embodiment of this aspect, the subject's imagination/creativity is scored on a scale from 0 to 8, wherein the score of 0 corresponds with a subject who pretends that a doll or other toy is something else during an imaginative play scenario, wherein the score of 1 corresponds with a subject who may independently play pretend with a doll or other object but with limited creativity or variation, wherein the score of 2 corresponds with a subject who only imitates the pretend play after watching a caregiver or other individual(s), and does not initiate pretend play on own, wherein the score of 3 corresponds with a subject who does not exhibit pretend play, and wherein the score of 8 corresponds with a subject for whom the subject's level of imagination/creativity is not applicable or cannot be scored.

In another aspect, provided herein is a system of diagnosing an autism spectrum disorder in a subject, the system comprising: a scoring system for scoring the subject's behavior; an analysis system for analyzing results of the scoring with a diagnostic tool to generate a final score, wherein the diagnostic tool is generated by applying artificial intelligence to an instrument for diagnosis of the autism spectrum disorder; and an indicator system for indicating whether the subject has the autism spectrum disorder based on the final score generated by the analyzing step.

In one embodiment of this aspect, the instrument is a caregiver-directed questionnaire, and wherein the scoring system consists of: a system for scoring the subject's understanding of basic language; a system for scoring the subject's use of back-and-forth conversation; a system for scoring the subject's level of imaginative or pretend play; a system for scoring the subject's level of imaginative or pretend play with peers; a system for scoring the subject's use of eye contact; a system for scoring the subject's behavior in peer groups; and a system for scoring the subject's age when abnormality first recognized.

In another embodiment of this aspect, the subject's understanding of basic language is scored on a scale from 0 to 8, wherein the score of 0 corresponds with a subject who in response to a request can place an object, other than something to be used by himself/herself, in a new location in a different room, wherein the score of 1 corresponds with a subject who in response to a request can usually get an object, other than something for herself/himself from a different room, but usually cannot perform a new task with the object such as put it in a new place, wherein the score of 2 corresponds with a subject who understands more than 50 words, including names of friends and family, names of action figures and dolls, names of food items, but does not meet criteria for the previous two answers, wherein the score of 3 corresponds with a subject who understands fewer than 50 words, but some comprehension of "yes" and "no" and names of a favorite objects, foods, people, and also words within daily routines, wherein the score of 4 corresponds with a subject who has little or no understanding of words, and wherein the score of 8 corresponds with a subject whose understanding of basic language is not applicable.

In another embodiment of this aspect, the subject's back-and-forth conversation is scored on a scale from 0 to 8, wherein the score of 1 corresponds with a subject for whom conversation flows, with the subject and another person both contributing to an ongoing dialogue, wherein the score of 2 corresponds with a subject who exhibits occasional back-and-forth conversation, but limited in flexibility or topics, wherein the score of 3 corresponds with a subject who exhibits little or no back-and-forth conversation, wherein the subject has difficulty building a conversation, wherein the subject fails to follow a conversation topic, and wherein the subject may ask or answer questions but not as part of a dialogue, wherein the score of 4 corresponds with a subject who rarely speaks or initiates conversation, and wherein the score of 8 corresponds with a subject for whom level of back-and-forth conversation is not applicable or cannot be scored.

In another embodiment of this aspect, the subject's level of imaginative or pretend play is scored on a scale from 0 to 8, wherein the score of 0 corresponds with a subject exhibiting a variety of imagination and pretend play, including use of toys to engage in play activity, wherein the score of 1 corresponds with a subject exhibiting some imagination and pretend play, including pretending with toys, but limited in variety or frequency, wherein the score of 2 corresponds with a subject exhibiting occasional pretending or highly repetitive pretend play, or only play that has been taught by others, wherein the score of 3 corresponds with a subject showing no pretend play, and wherein the score of 8 corresponds with a subject whose level of imaginative or pretend play is not applicable.

In another embodiment of this aspect, the subject's level of imaginative or pretend play with peers is scored on a scale from 0 to 8, wherein the score of 0 corresponds with a subject who actively participates in imaginative play with other children in which the subject leads and follows another child in pretend activities, wherein the score of 1 corresponds with a subject who exhibits some participation in pretend play with another child, but not truly back-and-forth, or level of pretending/imagination is limited in variety, wherein the score of 2 corresponds with a subject who exhibits some play with other children, but little or no pretending, wherein the score of 3 corresponds with a subject who engages in no play with other children or no pretend play when alone, and wherein the score of 8 corresponds with the subject's level of imaginative or pretend play with peers is not applicable.

In another embodiment of this aspect, the subject's use of eye contact is scored on a scale from 0 to 8, wherein the score of 0 corresponds with a subject for whom normal eye contact is used to communicate across a range of situations and people, wherein the score of 1 corresponds with a subject who makes normal eye contact, but briefly or inconsistently during social interactions, wherein the score of 2 corresponds with a subject who makes uncertain/occasional direct eye contact, or eye contact rarely used during social interactions, wherein the score of 3 corresponds with a subject who exhibits unusual or odd use of eye contact, and wherein the score of 8 correspond with a subject whose use of eye contact is not applicable or scorable.

In another embodiment of this aspect, the subject's level of play behavior in peer groups is scored on a scale from 0 to 8, wherein the score of 0 corresponds with a subject who actively seeks and plays together with peers in several different groups in a variety of activities or situations, wherein the score of 1 corresponds with a subject who exhibits some play with peers, but tends not to initiate, or tends to be inflexible in the games played, wherein the score of 2 corresponds with a subject who enjoys parallel active play, but little or no cooperative play, wherein the score of 3 corresponds with a subject who seeks no play that involves participation in groups of other children, though may chase or play catch, and wherein the score of 8 corresponds with the subject's level of imaginative or pretend play with peers is not applicable.

In another embodiment of this aspect, the subject's age when abnormality first recognized is scored on a scale from 0 to 4, wherein the score of 0 corresponds with a subject for whom development in the first 3 years of life has been or was clearly normal in quality and within normal limits for social, language, and physical milestones, and wherein the subject exhibits no behavioral problems that might indicate developmental delay, wherein the score of 1 corresponds with a subject for whom development is potentially normal during first 3 years, but uncertainty because of some differences in behavior or level of skills in comparison to children of the same age, wherein the score of 2 corresponds with a subject for whom development has been or was probably abnormal by or before the age of 3 years, as indicated by developmental delay, but milder and not a significant departure from normal development, wherein the score of 3 indicates that development has been or was clearly abnormal during the first 3 years, but not obvious as autism, and wherein the score of 4 indicates that the subject's development has been or was clearly abnormal during the first 3 years and quality of behavior, social relationships, and communications appear to match behaviors consistent with autism.

In another embodiment of this aspect, the instrument is a set of questions that correspond to an observation of the subject in a video, video conference or in person, and wherein the scoring system consists of: a system for scoring the subject's tendency to direct sounds, words or other vocalizations to others; a system for scoring the subject's use of eye contact; a system for scoring the subject's tendency to smile in response to social queues; a system for scoring the subject's shared enjoyment in interaction; a system for scoring the subject's tendency to show objects to another person; a system for scoring the subject's tendency to initiate joint attention; a system for scoring the subject's level of appropriate play with toys or other objects; and a system for scoring the subject's level of imagination/creativity.

In another embodiment of this aspect, the subject's tendency to direct sounds, words or other vocalizations to others is scored on a scale from 0 to 8, wherein the score of 0 corresponds with a subject who directs sounds, words or other vocalizations to a caregiver or to other individuals in a variety of contexts and who chats or uses sounds to be friendly, express interest, and/or to make needs known, wherein the score of 1 corresponds with a subject who directs sounds, words or other vocalizations to a caregiver or to other individuals regularly in one context, or directs vocalizations to caregiver or other individuals irregularly across a variety of situations/contexts, wherein the score of 2 corresponds with a subject who occasionally vocalizes to a caregiver or other individuals inconsistently in a limited number of contexts, possibly including whining or crying due to frustration, wherein the score of 3 corresponds with a subject who almost never vocalizes or vocalizations never appear to be directed to caregiver or other individuals in the observation of the subject in a video, video conference or in person, and wherein the score of 8 corresponds with a subject whose tendency to direct sounds, words or other vocalizations to others is not applicable.

In another embodiment of this aspect, the subject's use of eye contact is scored on a scale from 0 to 8, wherein the score of 0 corresponds with a subject who makes normal eye contact, wherein the score of 2 corresponds with a subject who has some irregular or unusual use of eye contact to initiate, terminate, or regulate social interaction, and wherein the score of 8 corresponds with a subject whose use of eye contact is not applicable or scorable.

In another embodiment of this aspect, the subject's tendency to smile in response to social queues is scored on a scale from 0 to 8, wherein the score of 0 corresponds with a subject who smiles immediately in response to smiles by the caregiver or other individuals in the observation of the subject in a video, video conference or in person and with a subject who can switch from not smiling to smiling without being asked to smile, wherein the score of 1 corresponds with a subject who delays, only smiles partially, smiles only after repeated smiles by caregiver or other individuals in the observation of the subject in a video, video conference or in person, or smiles only when asked, wherein the score of 2 corresponds with a subject who smiles fully or partially at the caregiver or other individuals only after being tickled, or only after being prompted by repeated attempts which may include using a toy or other object, wherein the score of 3 corresponds with a subject who does not smile in response to another person, and wherein the score of 8 corresponds with a subject whose tendency to smile in response to social queues is not applicable or cannot be scored.

In another embodiment of this aspect, the subject's shared enjoyment in interaction is scored on a scale from 0 to 8, wherein the score of 0 corresponds with a subject who shows clear and appropriate happiness with the caregiver or other individuals during two or more activities, wherein the score of 1 corresponds with a subject who shows somewhat inconsistent signs of happiness with the caregiver or other individuals during more than one activity, or only shows signs of happiness with the caregiver or others involved during one interaction, wherein the score of 2 corresponds with a subject who shows little or no signs of happiness in interaction with the caregiver or others in the observation of the subject in a video, video conference or in person although may exhibit signs of happiness when playing alone, wherein the score of 8 corresponds with a subject whose shared enjoyment in interaction is not applicable or cannot be scored.

In another embodiment of this aspect, the subject's tendency to show objects to another person is scored on a scale from 0 to 8, wherein the score of 0 corresponds with a subject who spontaneously shows toys or objects at various times during the observation of the subject in a video, video conference or in person by holding them up or putting them in front of others and using eye contact with or without vocalization, wherein the score of 1 corresponds with a subject who shows toys or objects partially or inconsistently, wherein the score of 2 corresponds with a subject who does not show objects to another person, and wherein the score of 8 corresponds with a subject whose tendency to show objects to another person is not applicable or cannot be evaluated.

In another embodiment of this aspect, the subject's tendency to initiate joint attention is scored on a scale from 0 to 2, wherein the score of 0 corresponds with a subject who uses normal eye contact to reference an object that is out of reach by looking back-and-forth between the caregiver or other person and the object, wherein eye contact may be used with pointing and/or vocalization, wherein the score of 1 corresponds with a subject who partially references an object that is out of reach, wherein the subject may spontaneously look and point to the object and/or vocalize, but does not use eye contact to get the attention of another person and then look at or point to the examiner or the parent/caregiver, but not look back at the object, and wherein the score of 2 corresponds with a subject that does not attempt to try to get another person's attention to reference an object that is out of reach.

In another embodiment of this aspect, the subject's level of appropriate play with toys or other objects is scored on a scale from 0 to 8, wherein the score of 0 corresponds with a subject who independently plays with a variety of toys in a conventional manner, including appropriate play with action figures or dolls, wherein the score of 1 corresponds with a subject who plays appropriately with some toys but not always, wherein the score of 2 corresponds with a subject who plays with only one toy or one type of toy despite there being others around to play with, or only imitates others when playing with a toy, wherein the score of 3 corresponds with a subject who does not play with toys or plays with toys in an inappropriate, stereotyped, or repetitive way, and wherein the score of 8 corresponds with a subject whose level of appropriate play with toys or other objects is not applicable or cannot be scored.

In another embodiment of this aspect, the subject's imagination/creativity is scored on a scale from 0 to 8, wherein the score of 0 corresponds with a subject who pretends that a doll or other toy is something else during an imaginative play scenario, wherein the score of 1 corresponds with a subject who may independently play pretend with a doll or other object but with limited creativity or variation, wherein the score of 2 corresponds with a subject who only imitates the pretend play after watching a caregiver or other individual(s), and does not initiate pretend play on own, wherein the score of 3 corresponds with a subject who does not exhibit pretend play, and wherein the score of 8 corresponds with a subject for whom the subject's level of imagination/creativity is not applicable or cannot be scored.

In another aspect, provided herein is a computer implemented method of generating a diagnostic tool by applying artificial intelligence to an instrument for diagnosis of a disorder, wherein the instrument comprises a full set of diagnostic items, the computer implemented method comprising: on a computer system having one or more processors and a memory storing one or more computer programs for execution by the one or more processors, the one or more computer programs including instructions for: scoring the subject's behavior; analyzing results of the scoring with a diagnostic tool to generate a final score, wherein the diagnostic tool is generated by applying artificial intelligence to an instrument for diagnosis of the autism spectrum disorder; and providing an indicator as to whether the subject has the autism spectrum disorder based on the final score generated by the analyzing step.

In another aspect, provided herein is a computer system of diagnosing an autism spectrum disorder in a subject, the system comprising: one or more processors; and memory to store: one or more computer programs, the one or more computer programs comprising instructions for: scoring the subject's behavior; analyzing results of the scoring with a diagnostic tool to generate a final score, wherein the diagnostic tool is generated by applying artificial intelligence to an instrument for diagnosis of the autism spectrum disorder; and providing an indicator as to whether the subject has the autism spectrum disorder based on the final score generated by the analyzing step.

In another aspect, provided herein is a non-transitory computer-readable storage medium storing one or more computer programs configured to be executed by one or more processing units at a computer comprising instructions for: scoring a subject's behavior; analyzing results of the scoring with a diagnostic tool to generate a final score, wherein the diagnostic tool is generated by applying artificial intelligence to an instrument for diagnosis of the autism spectrum disorder; and providing an indicator as to whether the subject has an autism spectrum disorder based on the final score generated by the analyzing step.

BRIEF DESCRIPTION OF THE DRAWINGS

The accompanying drawings, which are incorporated into this specification, illustrate one or more exemplary embodiments of the inventions disclosed herein and, together with the detailed description, serve to explain the principles and exemplary implementations of these inventions. One of skill in the art will understand that the drawings are illustrative only, and that what is depicted therein may be adapted based on the text of the specification and the spirit and scope of the teachings herein.

In the drawings, where like reference numerals refer to like reference in the specification:

FIG. 9 shows an example of the use of social networks with the present invention;

FIG. 10 is another example of the use of social networks with the present invention;

FIG. 18 is yet another example of the use of social networks with the present invention;

FIG. 23 shows an example of a query screen associated with a Watch and Score Home Videos module;

FIG. 32 shows an example of an input system prompting the user to enter patient information;

FIG. 33 shows an example of an input system prompting the user to upload, change or view a video;

FIG. 34 shows an example of a video;

FIG. 35 shows an example of video analysis web framework;

FIG. 38 shows an example of workflow for the CDC; and

FIG. 39 shows an example of workflow for the VBC.

DETAILED DESCRIPTION

Figure 1:
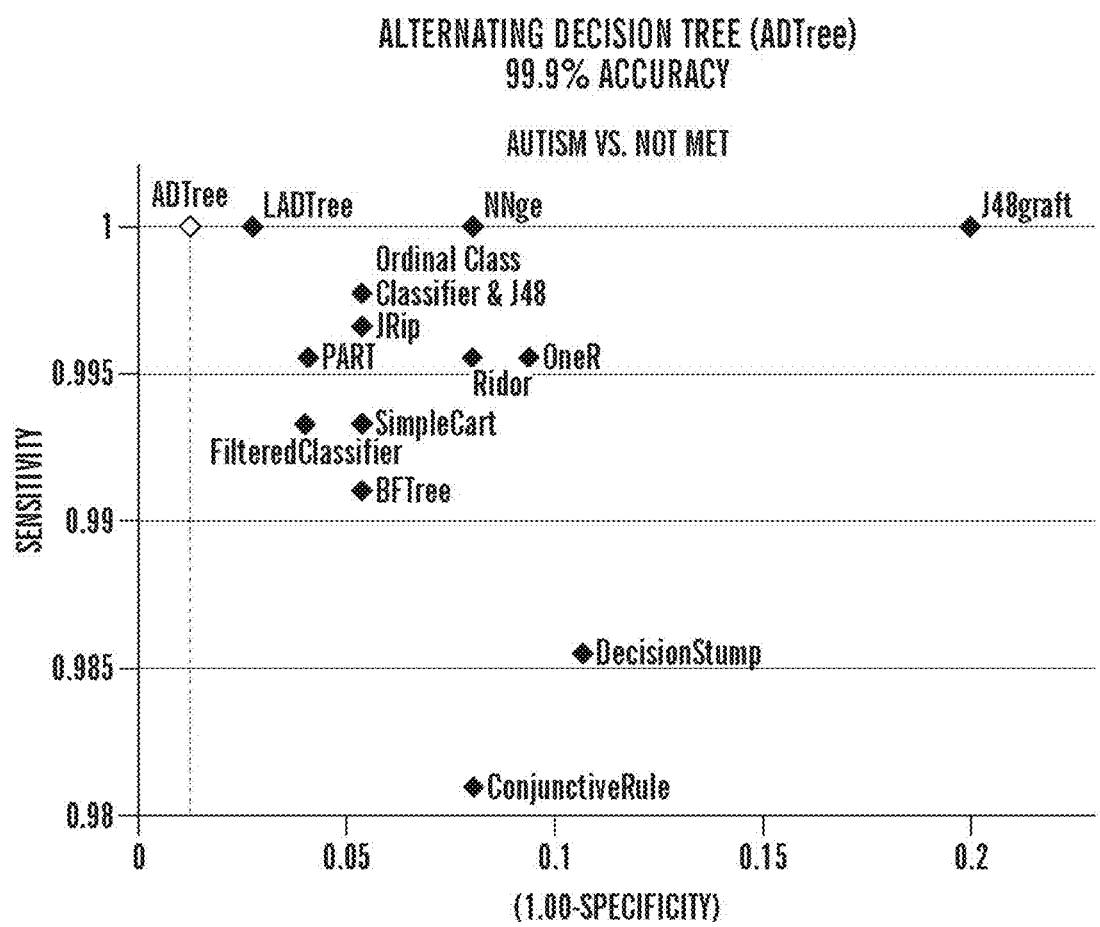
FIG. 1 is a chart showing performance of all 15 machine learning algorithms evaluated for classifying autism cases versus controls (ADI-R)

It should be understood that this invention is not limited to the particular methodology, protocols, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities used herein should be understood as modified in all instances by the term "about."

All publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

Some Selected Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments of the aspects described herein, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Other than in the operating examples, or where otherwise indicated, all numbers expressing quantities used herein should be understood as modified in all instances by the term "about." The term "about" when used in connection with percentages may mean±1%.

The singular terms "a," "an," and "the" include plural referents unless context clearly indicates otherwise. Similarly, the word "or" is intended to include "and" unless the context clearly indicates otherwise. Thus for example, references to "the method" includes one or more methods, and/or steps of the type described herein and/or which will become apparent to those persons skilled in the art upon reading this disclosure and so forth.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. The terms, "patient" and "subject" are used interchangeably herein.

The present invention can use statistical classification techniques including methods in artificial intelligence and machine learning, as well as other statistical approaches including hierarchical clustering, methods of phylogenetic tree reconstruction including parsimony, maximum likelihood, and distance optimality criteria, and pattern recognition and data exploration approaches such as principle components analysis, correspondence analysis and similar methods, to identify a minimal set of explanatory behaviors/phenotypes/morphologies that can accurately indicate the presence or absence of a human disorder (principally including autism).

To the extent not already indicated, it will be understood by those of ordinary skill in the art that any one of the various embodiments herein described and illustrated may be further modified to incorporate features shown in any of the other embodiments disclosed herein.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Part I: Use of Artificial Intelligence to Shorten the Behavioral Diagnosis of Autism Abstract The Autism Diagnostic Interview-Revised (ADI-R) is one of the most commonly used instruments for behavioral diagnosis of autism. The exam consists of over 150 elements that must be addressed by a care provider and interviewer within a focused session that can last up to 2.5 hours. According to the present invention, machine learning techniques can be used to study the complete sets of answers to the ADI-R available at the Autism Genetic Research Exchange (AGRE) for 891 individuals diagnosed with autism and 75 individuals who did not meet the criteria for autism diagnosis. The analysis according to the invention showed that 7 of the 152 items contained in the ADI-R were sufficient to diagnosis autism with 99.9% statistical accuracy. The invention can include further testing of the accuracy of this 7-question classifier against complete sets of answers from two independent sources, a collection of 1,654 autistic individuals from the Simons Foundation and a collection of 322 autistic individuals from the Boston Autism Consortium (AC). (Other independent sources can be used including but not limited to National Database for Autism Research, The Autism Genetic Research Exchange or any suitable repository of data.) In both cases, the classifier performed with nearly 100% statistical accuracy, properly categorizing all but one of the individuals from these two resources who previously had been diagnosed with autism through the standard ADI-R. With incidence rates rising, the capacity to diagnose autism quickly and effectively requires careful design of behavioral diagnostics. The invention is the first attempt to retrospectively analyze large data repositories to derive a highly accurate, but significantly abbreviated diagnostic instrument. According to the present invention, a completely new diagnostic tool is created, which is designed to target elements, i.e., behaviors and morphology, that the present machine learning processes identify as vital to a diagnosis and, critically, an algorithm is created, which intelligently, i.e., numerically and statistically, combines the target elements to provide a disorder/non-disorder classification. Such retrospective analyses provide valuable contributions to the diagnosis process and help lead to faster screening and earlier treatment of autistic individuals.

Summary

The incidence of autism has increased dramatically over recent years, making this mental disorder one of the greatest public health challenges of our time. The standard practice of diagnosis is strictly based on behavioral characteristics, as the genome has largely proved intractable for diagnostic purposes. Yet, the most commonly used behavioral instruments take as much as 3 hours to administer by a trained specialist, contributing to the substantial delays in diagnosis experienced by many children, who may go undiagnosed and untreated until ages beyond when behavioral therapy would have had more substantive positive impacts. In the present study, the invention can use machine learning techniques to analyze the answers to one of the most commonly used behavioral instruments, the Autism Diagnostic Interview-Revised (ADI-R), to determine if the exam could be shortened without loss of diagnostic accuracy. Deploying an alternative decision tree learning algorithm according to the invention, the total number of questions can be successfully reduced from 93 to 7, a total reduction of 93%. This abbreviation came with almost no loss in the accuracy when compared to the diagnosis provided by the full ADI-R in three independent collections of data and over 2,800 autistic cases. Such a diagnostic tool could have significant impact on the timeframe of diagnosis, making it possible for more children to receive diagnosis and care early in their development.

Introduction

Although autism is a genetic disease (Bailey, et al., "Autism as a strongly genetic disorder: evidence from a British twin study," *Psychol Med*, 1995, 25(1):63-77), it is diagnosed through behavior. The clinical practice of diagnosis has been formalized through instruments containing questions carefully designed to assess impairments in three developmental domains: communication and social interactions, restricted interests and activities, and stereotypical behaviors. One of the most widely adopted instruments is the Autism Diagnostic Interview—Revised (ADI-R) (Lord, et al., "Autism Diagnostic Interview-Revised: a revised version of a diagnostic interview for caregivers of individuals with possible pervasive developmental disorders," *J Autism Dev Disord*, 1994, 24(5):659-685). This exam contains 93 main questions and numerous sub-elements that sum to over 150 items. It is an interview-based exam conducted by a trained individual who obtains information from an informant, e.g., parent or caregiver. The exam is meant to inquire about individuals with a mental age of at least two years, and due to the large number of questions in the exam, can take up to 2.5 hours to complete. While the instrument is highly reliable, consistent across examiners (Cicchetti, et al., "Reliability of the ADI-R: multiple examiners evaluate a single case," Autism Dev Disord, 2008, 38(4):764-770), and results in a rich understanding of the individual suspected of having autism, its length can be prohibitive.

The practice of diagnosing autism varies widely in terms of standards and timeframes. Children may wait as long as 13 months between initial screening and diagnosis (Wiggins, et al., "Examination of the time between first evaluation and first autism spectrum diagnosis in a population-based sample," *Journal of developmental and behavioral pediatrics*, IDBP 2006, 27(2 Suppl):S79-87). Similar studies have also found substantial delays between the time of first parental concern and actual diagnosis. Substantial delays in diagnosis are often seen in families with different racial and ethnic backgrounds, partly due to socioeconomic status and cultural beliefs, for example, African American children spend more time in treatment before receiving an autism spectrum disorder (ASD) diagnosis (Bernier, et al., "Psychopathology, families, and culture: autism," *Child Adolesc Psychiatr Clin N Am*, 2010, 19(4):855-867). A shortened and readily accessible diagnostic exam could improve these statistics.

Significant attention has been paid to the design of abbreviated screening examinations that are meant to foster more rapid diagnosis, including the Autism Screening Questionnaire (ASQ, designed to discriminate between PDD and non-PDD diagnoses (Berument, et al., "Autism screening questionnaire: diagnostic validity," *Br J Psychiatry*, 1999, 175:444-451)), the Modified Checklist for Autism in Toddlers (MCHAT) (Robins, et al., "The Modified Checklist for Autism in Toddlers: an initial study investigating the early detection of autism and pervasive developmental disorders," *J Autism Dev Disord*, 2001, 31(2):131-144), and the Parents' Evaluation of Developmental Status (PEDS) (Pinto-Martin, et al., "Screening strategies for autism spectrum disorders in pediatric primary care," *J Dev Behav Pediatr*, 2008, 29(5): 345-350), to name a few. However, most of these have been adopted for basic screening rather than formal diagnosis, and are tools used prior to administering the ADI-R or Autism Diagnostic Observation Schedule (ADOS) (Lord, et al., "Autism diagnostic observation schedule: a standardized observation of communicative and social behavior," *J Autism Dev Disord*, 1989, 19(2):185-212). While some pediatricians conduct routine autism screenings during well-child visits, it has yet to become a universal practice (Gura, et al., "Autism spectrum disorder screening in primary care," *J Dev Behav Pediatr*, 2011, 32(1):48-51) leaving much of the burden on the parent or care provider. Parents often hesitate to take immediate action without a clinical assessment and formal diagnosis, furthering delays in the treatment of the child through behavioral therapy or other means (Howlin, "Children with Autism and Asperger's Syndrome: A Guide for Practitioners and Parents," Chichester, UK: Wiley; 1998)(Pisula, "Parents of children with autism: review of current research," *Arch Psychiatry Psychother*, 2003, 5:51-63). An exam that preserves the reliability of the ADI-R but that can be administered in minutes rather than hours enables more rapid diagnosis, higher throughput, as well as timely and more impactful delivery of therapy.

A direct way to test whether a reduction of the complexity of ADI-R provides the same level of accuracy as the full exam is to look retrospectively at answers to the full ADI-R for a large set of individuals with autism. Many efforts to-date on shortening the behavioral diagnosis of autism have leveraged clinical experience and criteria established by the DSM-IV to prospectively design and test new instruments. However, as a valuable byproduct of the widespread adoption and use of ADI-R, researchers now have large digital repositories of item-level answers to each question coupled with the clinical diagnosis that can be mined to test this question directly. According to the invention, analytical strategies can be employed from the field of machine learning to retrospectively analyze the full ADI-R for over 800 individuals with autism, with the aim centered on significantly reducing the number of questions while preserving the classification given by the full ADI-R.

Results

The invention may begin with ADI-R data from the Autism Genetic Resource Exchange (AGRE). After removing 24 questions that did not meet the standards for inclusion, 129 questions and sub-questions from the full ADI-R data were left. The invention can compare the performance of 15 different machine learning algorithms on these 129 attributes. In accordance with the invention, the Alternating Decision Tree (ADTree) is shown to perform the best in terms of both sensitivity and specificity of classification (FIG. 1), with perfect sensitivity of 1.0, a false positive rate (FPR) of 0.013, and overall accuracy of 99.90%. See Table 1 for a summary of the 15 machine learning algorithms used in the analysis.

Figure 2:
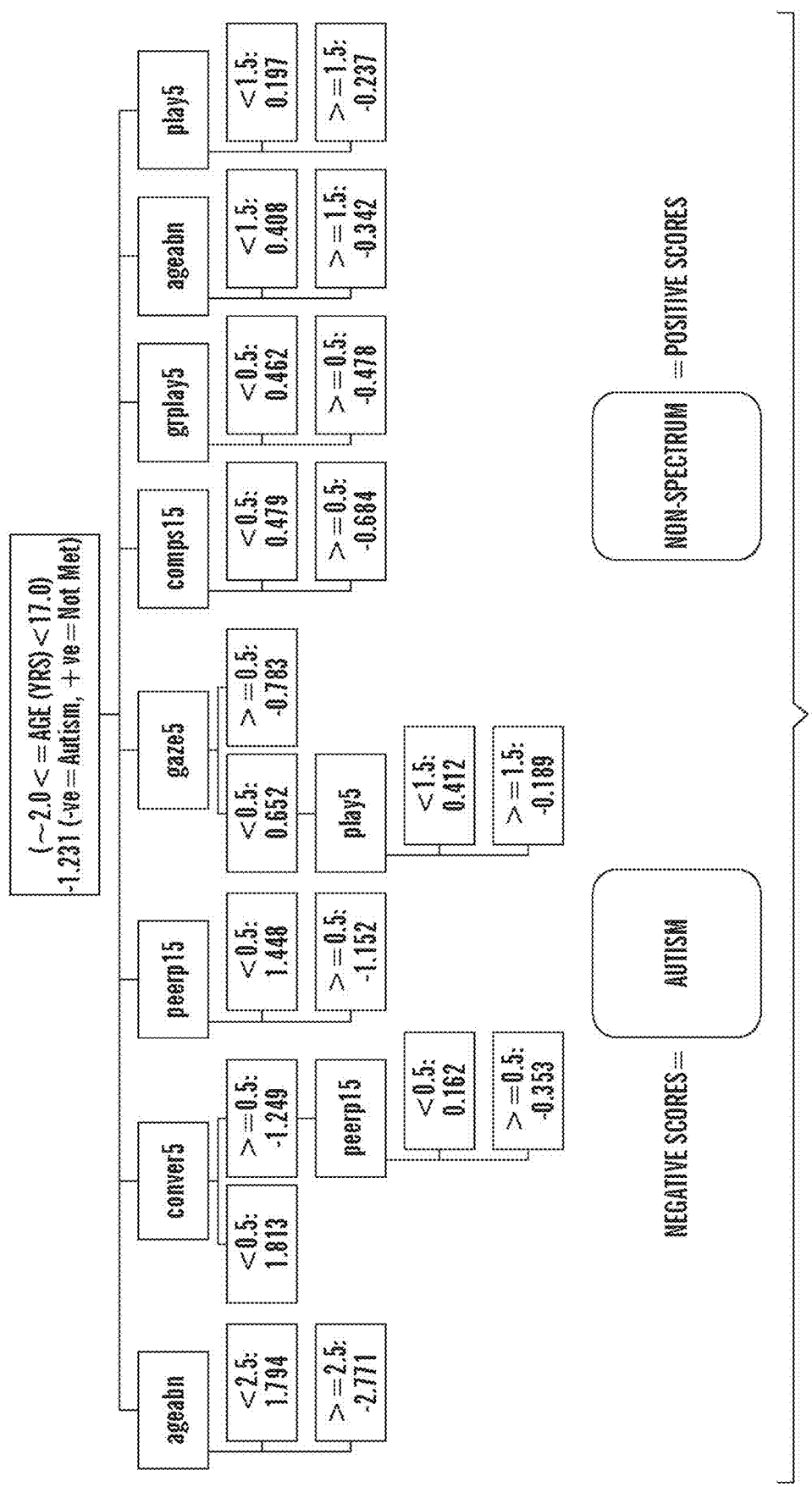
FIG. 2 shows an example of a decision tree for a behavioral classifier generated by the Alternating Decision Tree (ADTree) algorithm (ADI-R)

FIG. 1 charts the performance of all 15 machine learning algorithms evaluated for classifying autism cases versus controls. Receiver operator curves mapping 1-specificity versus sensitivity for the 15 different machine learning algorithms tested against the Autism Diagnostic Interview-Revised (ADI-R) data from the Autism Genetic Resource Exchange (ACRE). The algorithm of the present invention yielding a classifier with false positive rate closest to 0 and true positive rate closest to 1, a perfect classifier, was identified. The best performing approach was the alternating decision tree (ADTree), followed by LADTree, PART, and FilteredClassifier. Table 1 summarizes the 15 machine learning algorithms in more detail, and the resulting classifier as a decision tree is depicted in FIG. 2. In FIG. 1, the x-axis ranges from 0 to 0.2 with increments of 0.05, and the y-axis ranges from 0.98 to 1 with increments of 0.005.

Table 1 shows 15 machine learning algorithms used to analyze the Autism Genetic Resource Exchange ADI-R data. These algorithms were deployed using the toolkit WEKA. The false positive rate (FPR) and true positive rate (TPR) are provided together with overall accuracy. The Alternating Decision Tree (ADTree) performed with highest accuracy and was used for further analysis.

TABLE 1

| Classifier Name | Description | FPR | TPR | Accuracy |
| --- | --- | --- | --- | --- |
| ADTree | An ADTree combines decision trees, voted decision trees, and voted decision stumps. This particular algorithm is based on boosting, which produces accurate predictions by combining a series of "weak" learners that together, can classify accurately (Freund, et al., "The alternating decision tree learning algorithm," In: *Machine Learning: Proceedings of the Sixteenth International Conference 1999*, 124-133). | 0.013 | 1.000 | 0.999 |
| BFTree | The top node of the decision tree is the one that splits the data so that the maximum reduction of impurity (misclassified data) is achieved. This is called the "best" node, and it is expanded upon first (unlike in a C4.5 tree, for example, where nodes are expanded upon according to depth-first) (Shi, "Best-first Decision Tree Learning," Master Thesis, *The University of Waikato*, 2007). | 0.053 | 0.991 | 0.988 |
| ConjunctiveRule | Within the ConjuctiveRule classifier is a conjunctive rule learner, which can predict for both numeric and nominal class labels. A rule consists of a series of antecedents joined by "AND"s (Freund, et al., "Experiments with a new boosting algorithm," In: *Proceedings of the International Conference on Machine Learning: 1996; San Francisco*, Morgan Kautinann: 148-156). | 0.080 | 0.981 | 0.976 |
| DecisionStump | A DecisionStump classifier is a single-level decision tree with one node. The terminal nodes extend directly off of this node, so a classification is made based on a single attribute (Freund, et al., "Experiments with a new boosting algorithm," In: *Proceedings of the International Conference on Machine Learning: 1996; San Francisco*, Morgan Kautinann: 148-156). | 0.107 | 0.985 | 0.978 |
| FilteredClassifier | FilteredClassifier runs data through an arbitrary classifier after its been run through an arbitrary filter. Classifiers are built using training data, and in this case, the filter is also built based on the training data. This allows the user | 0.040 | 0.993 | 0.991 |

TABLE 1-continued

| Classifier Name | Description | FPR | TPR | Accuracy |
|---|---|---|---|---|
| | to skip the pre-processing steps associated with transforming the data (Hall, et al., "The WEKA Data Mining Software: An Update," *SIGKDD Explorations*, 2009, 11(1):1). | | | |
| J48 | J48 is a Java implementation of the C4.5 algorithm; it generates either an unpruned or a pruned C4.5 decision tree. C4.5 uses the concept of information entropy to build trees from training data (Quinlan, "C4.5," San Mateo: Morgan Kaufmann Publishers; 1993). | 0.053 | 0.998 | 0.994 |
| J48graft | This class generates a grafted C4.5 decision tree that can either be pruned or unpruned. Grafting adds nodes to already created decision trees to improve accuracy (Freund, et al., "The alternating decision tree learning algorithm," In: *Machine Learning: Proceedings of the Sixteenth International Conference 1999*, 124-133). | 0.200 | 1.000 | 0.984 |
| JRip | This classifier is an optimized version of Incremental Reduced Error Pruning, and implements a propositional learner, RIPPER (Repeated Incremental Pruning to Produce Error Reduction). It produces accurate and "readable" rules (Cohen, "Fast Effective Rule Induction," *Twelfth International Conference on Machine Learning*, 1995:115-123) | 0.053 | 0.997 | 0.993 |
| LADTree | LADTree produces a multi-class alternating decision tree. It has the capability to have more than two class inputs. It uses the LogitBoost strategy, which performs additive logistic regression (Holmes, et al., "Multiclass alternating decision trees," *ECML*, 2001:161-172) | 0.027 | 1.000 | 0.998 |
| NNge | Nearest neighbor algorithms define a distance function to separate classes. Using generalized exemplars reduce the role of the distance function (relying too heavily on the distance function can produce inaccurate results) by grouping classes together (Martin, "Instance-Based learning: Nearest Neighbor With Generalization," Hamilton, New Zealand.: University of Waikato; 1995). | 0.080 | 1.000 | 0.994 |
| OneR | This algorithm finds association rules. It finds the one attribute that classifies instances so as to reduce prediction errors (Holte, "Very simple classification rules perform well on most commonly used datasets," *Machine Learning: Proceedings of the Sixteenth International Conference*, 1993, 11:63-91). | 0.093 | 0.996 | 0.989 |
| OrdinalClassClassifier | This is a meta-classifier (meta-classifiers are like classifiers, but have added functionality) used to transform an ordinal class problem to a series of binary class problems (Frank, et al., "A simple approach to ordinal prediction," In: *European Conference on Machine Learning; Freiburg, Germany*, Springer-Verlag 2001: 145-156). | 0.053 | 0.998 | 0.994 |
| PART | A set of rules is generated using the "divide-and-conquer" strategy. From here, all instances in the training data that are covered by this rule get removed and this process is repeated until no instances remain | 0.040 | 0.996 | 0.993 |

TABLE 1-continued

| Classifier Name | Description | FPR | TPR | Accuracy |
|---|---|---|---|---|
| | (Frank, et al., "Generating Accurate Rule Sets Without Global Optimization," In: *Machine Learning: Proceedings of the Fifteenth International Conference: 1998; San Francisco, CA*, Morgan Kaufmann Publishers). | | | |
| Ridor | This classifier is an implementation of a Ripple-Down Rule Learner. An example of this is when the classifier picks a default rule (based on the least weighted error), and creates exception cases stemming from this one (Gaines, et al., "Induction of Ripple-Down Rules Applied to Modeling Large Databases," *J Intell Inf Syst*, 1995, 5(3):211-228) | 0.080 | 0.996 | 0.990 |
| SimpleCart | Classification and regression trees are used to construct prediction models for data. They are made by partitioning the data and fitting models to each partition (Breiman, et al., "Classification and Regression Trees," *Wadsworth International Group, Belmont, California*, 1984). | 0.053 | 0.993 | 0.990 |

Specifically, the ADTree classifier correctly classified all AGRE individuals previously labeled with a diagnosis of autism using the full ADI-R exam and misclassified only 1 control individual. The ADTree classifier itself was composed of only 7 questions from the 129 total used in the analysis. These were ageabn, grplay5, conver5, peerp15, gaze5, play5, and comps15 (Table 1), and together represent a 95% reduction in the total number of elements overall.

Table 2 lists the seven attributes used in the ADTree model. Listed is the number corresponding to the question in the full ADI-R instrument, the question code used by Autism Genetic Research Exchange (ACRE), a brief description of the question, and the number of classifiers of the 15 tested in which the attribute appeared.

TABLE 2

| Question Number on ADI-R | Question Code | Question subject | Classifier Frequency |
|---|---|---|---|
| 29 | compsl5 | Comprehension of simple language: answer most abnormal between 4 and 5 | 3 |
| 35 | conver5 | Reciprocal conversation (within subject's level of language): answer if ever (when verbal) | 10 |
| 48 | play5 | Imaginative play: answer most abnormal between 4 and 5 | 3 |
| 49 | peerpl5 | Imaginative play with peers: answer most abnormal between 4 and 5 | 10 |
| 50 | gaze5 | Direct gaze: answer most abnormal between 4 and 5 | 6 |
| 64 | grplay5 | Group play with peers: answer most abnormal between 4 and 5 | 7 |

TABLE 2-continued

| Question Number on ADI-R | Question Code | Question subject | Classifier Frequency |
|---|---|---|---|
| 86 | ageabn | Age when abnormality first evident | 14 |

The 7 questions formed the elements of a decision tree through which the classification of "autism" or "not met" was derived (FIG. 2). Three questions appeared more than once in the tree (ageabn, play5, and peerp15), suggesting a slightly larger role in the classification outcome than the other 4 questions. Each question either increased or decreased a running sum score called the ADTree score. A negative score resulted in a diagnosis of "autism" and a positive score yielded the classification "not met." The amplitude of the score provided a measure of confidence in classification outcome, with larger absolute values indicating higher confidence overall, as previously indicated in Freund (Freund, et al., "A decision-theoretic generalization of on-line learning and an application to boosting," *Journal of Computer and System Sciences,* 1997, 55, 119-139). In the study, the vast majority of the scores were near or at the maximum for both the case and control classes, with comparably few individuals with intermediate values (FIG. 3) indicating that the predictions made by the classifier were robust and well supported.

FIG. 2 depicts the official behavioral classifier generated by the Alternating Decision Tree (ADTree) algorithm. The ADTree was found to perform best out of 15 different machine learning approaches (FIG. 1, Table 1) and achieved nearly perfect sensitivity and specificity when distinguishing autistic cases from controls. The resulting tree enables one to follow each path originating from the top node, sum the prediction values and then use the sign to determine the class. In this case, a negative sum yielded the classification of "autism" while a positive sum yielded the classification of "not met." Additionally, the magnitude of the sum is an indicator of prediction confidence.

Figure 3:
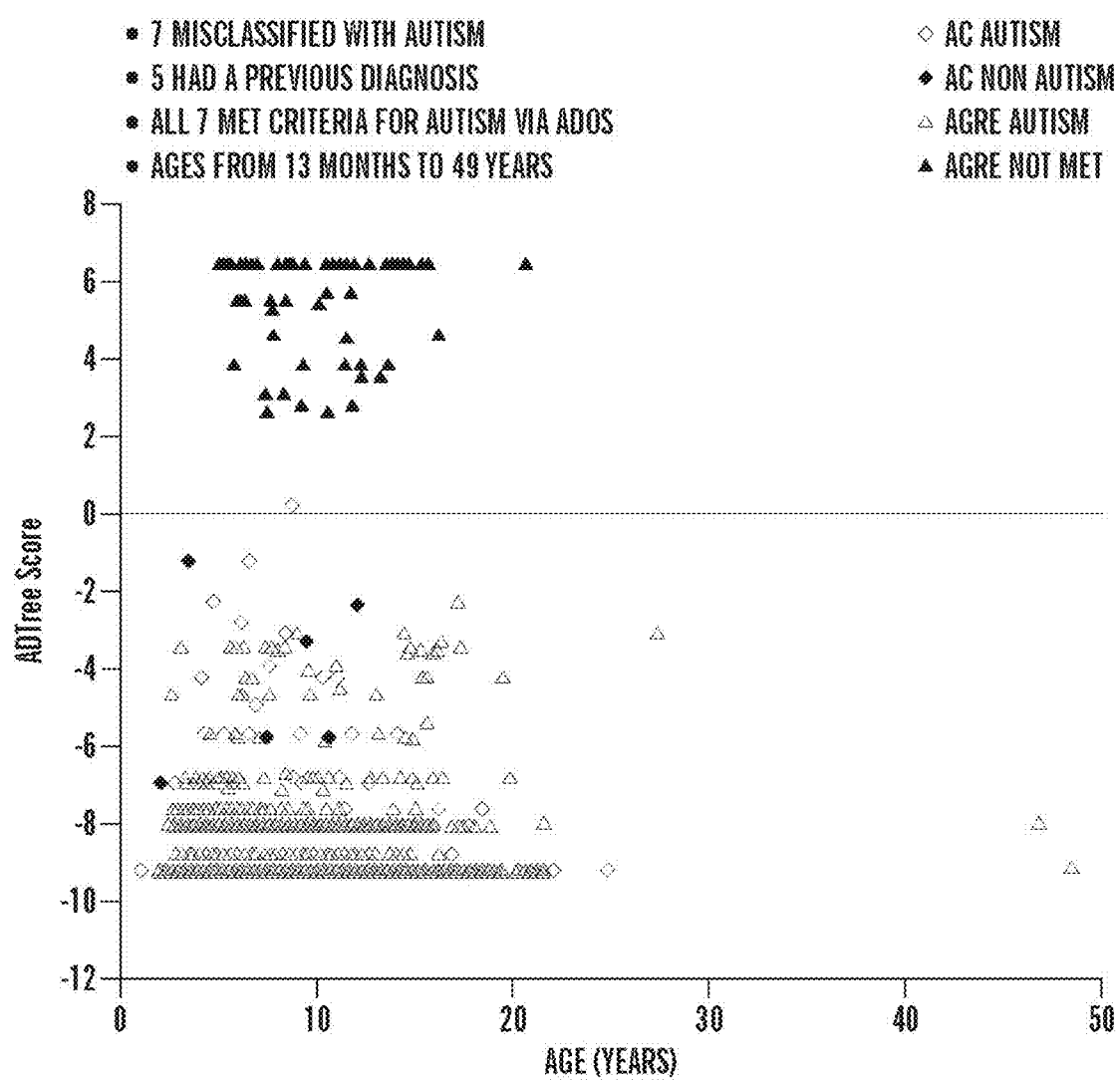
FIG. 3 is a chart showing decision tree scores and classification of cases with and without autism (ADI-R)

FIG. 3 shows an example of decision tree scores and classification of cases with and without autism. FIG. 3 includes the Alternating Decision Tree (ADTree) scores of individuals in both the AC and AGRE data sets versus their age in years. A majority of the ADTree scores are clustered towards greater magnitudes according to their respective classifications, regardless of age. In this case, 7 subjects were misclassified with autism, of which 5 had a previous diagnosis. All 7 met criteria for autism via ADOS. The subjects ranged in age from 13 months to 45 years. In FIG. 3, the x-axis ranges from 0 to 50 with increments of 10, and the y-axis ranges from −12 to 8 with increments of 2.

To independently validate the 7-question classifier, the invention can use completed ADI-R score sheets from two repositories, the Simons Foundation (SSC) and the Boston Autism consortium (AC) (Table 3).

Table 3 is a summary of the data used for both construction and validation of the autism diagnostic classifier. Full sets of answers to the Autism Diagnostic Instrument-Revised questionnaire were downloaded from the Autism Genetic Research Exchange (AGRE), the Simons Foundation (Simons), and the Boston Autism Consortium (AC). The AGRE data were used for training, testing, and construction of the classifier. The Simons and AC data were used for independent validation of the resulting classifier. Table 3 lists the total numbers of autistic and non-autistic individuals represented in each of the three data sets with a breakdown of age by quartiles.

TABLE 3

| | Classifier Data | Validation Data | |
| --- | --- | --- | --- |
| | AGRE | Simons | AC |
| | Autism Not Met | Autism Not Met | Autism Not Met |
| Sample Size | 891 75 | 1,654 4 | 308 2 |
| Q1 (Age) | 6.44 6.38 | 6.75 8.38 | 6.50 5.42 |
| Median (Age) | 8.06 9.24 | 8.75 9.75 | 8.50 9.50 |
| Q3 (Age) | 10.84 11.88 | 11.25 12.25 | 11.54 13.58 |
| IQR (Age) | 4.4 5.5 | 4.5 3.88 | 5.04 8.17 |

The classifier performed with high accuracy on both the Simons and AC data sets. All individuals in the SSC previously diagnosed with autism were accurately classified as autistic by the classifier. In the AC, the classifier accurately classified 321 of the 322 autistic cases (99.7% accuracy). Interestingly, the single misclassified individual from AC was predicted with a low-confidence ADTree score of 0.179 casting possible doubt on the classification and suggesting the potential that a further behavioral assessment of this individual could result in a non-spectrum diagnosis.

Given the limited number of individuals with the diagnosis of "not met," i.e., non-autistic individuals who could serve as controls in the validation step, the invention can group the controls from all three studies (AGRE, Simons, and AC) to increase the size of the control population to 84 individuals. In both the AC and SSC validation procedures only 7 of the 84 control individuals were misclassified, an overall accuracy of 92%. Further inspection of these 7 misclassified controls suggested that they likely had autism spectrum conditions and that their ADI-R diagnoses may not be accurate. Five had a previous diagnosis prior to recruitment to the study (2 with Asperger's Syndrome and 3 with Pervasive Developmental Disorder—Not Otherwise Specified (PDD-NOS)) and all 7 were diagnosed with either "autism" or "autism spectrum" by an alternative behavioral instrument, the Autism Diagnostic Observation Schedule (ADOS), in direct conflict with the classification diagnosis provided by the ADI-R. Such conflict in results further supported the possibility the 7 individuals misclassified by the classifier can in fact meet the criteria necessary for a formal autism diagnosis.

In an attempt to account for the small number of controls across all three datasets, the invention can simulate control data (e.g., a 1,000 simulated controls were generated) by random sampling from the pool of observed answers given by 84 control individuals classified as not meeting some or all criteria for autism diagnosis. The classifier performed with 99.9% accuracy on these 1,000 simulated controls, misclassifying only one.

Given the importance of diagnosis at early ages, the invention can also test the accuracy of the classifier on the collection of answers from children diagnosed at ages below 5. Although 5 of the 7 questions in the classifier probe for the most abnormal behavior between 4 and 5 years of age, according to the invention, the answers to those questions with the "current" behavior can be made equally accurate and allow expansion to younger children. Only the AGRE and AC datasets contained sufficient numbers of children below age 5 and thus the present invention need not use the SSC, as the Simons study restricts case recruitment to ages 4 and older, to test this hypothesis. For this analysis, the invention was tested against a total of 1,589 individuals previously listed as autistic in either AGRE or AC and 88 individuals flagged as not meeting the criteria for autism diagnosis. All but 1 of the children with autism were correctly categorized as having autism by the classifier, a near perfect accuracy of 99.9%, and 12 of the 88 controls were misclassified as having autism, corresponding to an 86% accuracy. As in the validation steps above, all 12 of these individuals had a conflicting ADOS categorization, suggesting the possibility that additional inspection and behavioral analysis can reveal that these 12 individuals meet the criteria necessary for an autism diagnosis.

Discussion

Current practices for the behavioral diagnosis of autism are highly effective but also prohibitively time consuming. A gold standard in the field is the Autism Diagnostic Interview-Revised (ADI-R), a 153-item exam that yields high inter-interviewer reliability and accuracy. The invention can use machine learning techniques to test whether the accuracy of the full ADI-R could be achieved with a significantly shorter version of the exam. The analysis found a small subset of 7 ADI-R questions targeting social, communication, and behavioral abilities to be 99.97% as effective as the full ADI-R algorithm for diagnosis of 2,867 autistic cases drawn from three separate repositories. This represents 96% fewer questions than the full ADI-R exam and 84% fewer questions than is contained in the ADI-R algorithm itself.

The analysis used machine learning techniques to analyze previous collections of data from autistic individuals, a practice that to date has not been commonplace in the field, but one that promotes novel and objective interpretation of autism data and promotes the development of an improved understanding of the autism phenotype. In the present case, several alternative machine learning strategies of the present invention yielded classifiers with very high accuracy and low rates of false positives. The top performing ADTree algorithm proved most valuable for classification as well as for measuring classification confidence, with a nearly 100% accuracy in the diagnosis of autistic cases. The ADTree algorithm resulted in a simple decision tree (FIG. 2) that can, according to the present invention, be readily converted into a behavioral algorithm for deployment in screening and/or diagnostic settings. In addition, the ADTree score provided an empirical measure of confidence in the classification that can be used to flag borderline cases likely warranting closer inspection and further behavioral assessment. In the present case, a small number of controls were misclassified, but with a low confidence score that suggested further screening and additional diagnostic tests might provide evidence that the original diagnosis was incorrect.

Limitations

The study was limited by the content of existing repositories, and as a consequence, the invention can have a relatively small number of matched controls for construction and validation of the classifier. In a prospective design for a study according to the invention, one would normally include equal numbers of cases and controls for optimal calculations of sensitivity and specificity of the classifier. Nevertheless, the clear demarcation between cases and controls found with the existing data (FIG. 3) provided confidence that the classifier scales to a larger population with equal or similar accuracy. In addition, the classifier performed with near perfect accuracy on a simulated set of 1,000 controls. While the simulated data were bounded by the empirical distribution of answers provided by the true control individuals, that empirical distribution covered a large space of answers likely to be provided by prospectively recruited controls. The invention can be expanded so as to include additional validation through the inclusion of new ADI-R data from both autistics and non-autistics.

The data used also contained a preponderance of older children, with highest density between ages of 5 and 17, potentially making the resulting classifier biased against effective diagnosis of younger children. However, the invention demonstrates near perfect classification accuracy for children 4 years of age and younger, with the youngest individual being 13 months (FIG. 3). As the sample sizes of younger children was relatively small, a larger sample can provide greater resolution and a larger set of training data to develop and test if a new classifier has greater accuracy than the one generated here.

Finally, since the classifier was trained only on individuals with or without classic autism it was not trained to pinpoint other diagnoses along the autism spectrum including Asperger and Pervasive Developmental Disorder—Not Otherwise Specified (PDD-NOS). This was a byproduct of the data available at the time of study; the data used in the study did not have sufficient granularity to test whether the classifier could be utilized for more fine-grained diagnoses. Either a large sample of ADI-R data from a range of ASDs or a prospective study, e.g., web-based survey/questionnaire (for example, like the web-based survey/questionnaire according to the present invention hosted on the Harvard Autworks website), enables measurement of the performance of the classifier outside of classic autism, and also enables retraining of the classifier should the performance be suboptimal.

Conclusions

Currently, the diagnosis of autism is through behavioral exams and questionnaires that require considerable time investment on the part of parents and clinicians. Using the present invention, the time burden for one of the most commonly used instruments for behavioral diagnosis, the Autism Diagnostic Interview-Revised (ADI-R), was significantly reduced. Deploying machine learning algorithms according to the present invention, the Alternating Decision Tree (ADTree) is found to have near perfect sensitivity and specificity in the classification of individuals with autism from controls. The ADTree classifier consisted of only 7 questions, 93% fewer than the full ADI-R, and performed with greater than 99% accuracy when applied to independent populations of autistics, misclassifying only one out of 1,962 cases. The classifier also performed with equally high accuracy on children under 4 and as young as 13 months, suggesting its applicability to a younger population of children with autism. Given this dramatic reduction in numbers of questions without appreciable loss in accuracy, the findings represent an important step to making the diagnosis of autism a process of minutes rather than hours, thereby enabling families to receive vital care far earlier in their child's development than under current diagnosis modalities.

Methods

Ethics Statement

The study (number: M18096-101) has been evaluated by the Harvard Medical School Institutional Review Board and identified as not involving human subjects as defined under 45CFR46.102(f) and as meeting the conditions regarding coded biological specimens or data. As such, (a) the specimens/data were not collected specifically for the research through an interaction or intervention with a living person, and (b) the investigators cannot "readily ascertain" the identity of the individual who provided the specimen/data to whom any code pertains. The Harvard Medical School Institutional Review Board determined the study to be exempt.

Constructing a Classifier

For constructing a classifier, phenotype data from the Autism Genetic Resource Exchange (Geschwind, et al., "The autism genetic resource exchange: a resource for the study of autism and related neuropsychiatric conditions," *American journal of human genetics,* 2001, 69(2):463-466) (AGRE) repository of families with at least one child with autism can be used. Specifically, the answers to the 153 questions and sub-questions in the 2003 version of ADI-R can be used. The initial analysis can be restricted to children with a diagnosis of "autism" from the categories "autism," "broad spectrum" and "not quite autism." Having one of these classifications was determined by the AGRE "affected status" algorithms, which used the domain scores from the ADI-R to evaluate the individuals. The "autism" classification used by AGRE follows the validated algorithm created by the authors of the ADI-R. If a child who took the ADI-R did not meet any of these classification criteria, he or she was deemed "not met," and was used as a control for the purposes of this study. Analyses were also restricted to children with and without an autism diagnosis who were 5 years of age or older and under the age of 17 years of age as the majority of data were from within this age range, thereby providing the most uniform collection of answers to the ADI-R and consequently the most complete matrix of data for machine learning. These steps resulted in 891 individuals with a classification of "autism" and 75 with a classification of "not met" (Table 3).

A series of machine learning analyses can be conducted to construct a classifier from the 93 ADI-R questions in order to distinguish individuals classified as "autistic" from those deemed "not met." In order to find an optimal classifier given the underlying data, the performance of 15 machine learning algorithms (Table 1) can be compared. For each algorithm, 10-fold cross validation can be used, with 90% of the data for training and the other 10% for testing, to build and assess the accuracy of the resulting classifier. Such cross-validation has been shown to perform optimally for structured, labeled data while reducing bias in the resulting classifier (Kohavi, "A study of cross-validation and bootstrap for accuracy estimation and model selection," In: *Proceedings IJCAI*-95: 1995; Montreal, Morgan Kaufmann, Los Altos, Calif.: 1137-I) and was therefore best suited to the present learning tasks. For each of the 15 classifiers, the false positive rate (FPR), true positive rate (TPR), as well as the accuracy can be measured. The specificity (FPR) can be plotted against sensitivity (TPR) to visualize the performance and to identify and select the optimal classifier for use in further analysis and validation. All machine learning steps were conducted using the Weka toolkit (Frank, et al., "Data mining in bioinformatics using Weka," *Bioinformatics*, 2004, 20(15):2479-2481).

Validating the Classifier

Although the 10-fold cross validation served as an internal validation of classifier accuracy, independent, age-matched ADI-R data from other families with autism whose data have been stored in the Simons Simplex Collection (Fischbach, et al., "The Simons Simplex Collection: a resource for identification of autism genetic risk factors," Neuron, 2010, 68(2):192-195) (SSC) and in the Boston Autism Consortium collection (AC) can be used to test the performance of the classifier. The SSC data consisted of 1,654 individuals classified with "autism" by the diagnostic standards of ADI-R and 4 that were found to be "nonspectrum" according to the Collaborative Programs of Excellence in Autism (CPEA) diagnostic algorithms established by Risi et al. (Risi, et al., "Combining information from multiple sources in the diagnosis of autism spectrum disorders," *Journal of the American Academy of Child and Adolescent Psychiatry*, 2006, 45(9):1094-1103). The families in the study were all simplex, i.e., only one child in the family with an ASD diagnosis. The AC set contained 322 individuals classified through the standard 2003 ADI-R as having "autism" and 5 classified as "non autism." The objective with these independent resources was to determine if the classifier constructed from the AGRE dataset could accurately distinguish between an individual classified by the full ADI-R algorithm as autistic from an individual classified as not meeting the criteria for an autism diagnosis.

Exclusion of Questions

Before running the data through the machine learning algorithms, questions can be removed from consideration if they contain a majority of exception codes indicating that the question could not be answered in the format requested. Also, all 'special isolated skills' questions and optional questions with hand-written answers can be removed.

Simulation of Controls

Because of the low numbers of controls in any of the datasets included in the study, the numbers can be boosted through a simple simulation process. For the creation of a simulated control, answers from the existing set of 84 controls can be randomly sampled, i.e., the total number of individuals who did not meet the criteria for an autism diagnosis in all three studies, SSC, AGRE, and AC. Random sampling can be performed for each question in the ADI-R by drawing randomly from the set of recorded answers for that question, therefore ensuring that distribution of answers in the simulated data were bounded by the empirical distribution in the observed answers. The process can be repeated, for example, 1,000 times and this dataset of simulated controls can be used for additional measurements (e.g., input to an algorithm, which can be descriptions of observed behavior in the format that the algorithm requires, the answers to questions about observed behaviors in the format that the algorithm requires, observations or questions) of the classifier's accuracy.

Part II: Use of Machine Learning to Shorten Observation-Based Screening and Diagnosis of Autism Abstract The Autism Diagnostic Observation Schedule-Generic (ADOS-G) is one of the most widely used instruments for behavioral evaluation of autism. It is composed of four different modules each tailored for a specific group of individuals based on their level of language. On average, each module takes between 30 to 60 minutes to deliver. A series of machine learning algorithms can be used to study the complete set of scores to the first module of the ADOS-G available at the Autism Genetic Resource Exchange (AGRE) for 612 individuals given a classification of autism and 15 individuals who did not meet the criteria for a classification of autism from AGRE and the Boston Autism Consortium (AC). The analysis indicated that 8 of the 29 items contained in the first module of the ADOS-G were sufficient to diagnose autism with 100% statistical accuracy. The accuracy of this 8-item classifier can be tested against complete sets of scores from two independent sources, a collection of 110 individuals with autism from AC and a collection of 336 individuals with autism from the Simons Foundation. (Other independent sources can be used including but not limited to National Database for Autism Research, The Autism Genetic Research Exchange or any suitable repository of data.) In both cases, the classifier performed with nearly 100% statistical accuracy correctly classifying all but two of the individuals from these two resources who previously had been diagnosed with autism through the ADOS-G. With incidence rates rising, the ability to recognize and classify autism quickly and effectively requires careful design of assessment and diagnostic tools. The research is among a small number of attempts to retrospectively analyze large data repositories to derive a highly accurate, but significantly abbreviated diagnostic instrument. According to the present invention, a completely new diagnostic tool is created, which is designed to target elements, i.e., behaviors and morphology, that the present machine learning processes identify as vital to a diagnosis and, critically, an algorithm is created, which intelligently, i.e., numerically and statistically, combines the target elements to provide a disorder/non-disorder classification. Such retrospective analyses provide valuable contributions to the diagnosis process and help lead to faster screening and treatment of individuals with autism.

Introduction

Although autism has a strong genetic component (Bailey, et al., "Autism as a strongly genetic disorder: evidence from a British twin study," *Psychol Med*, 1995, 25(1):63-77), it is largely diagnosed through behavior. Diagnosing autism has been formalized with instruments carefully devised to measure impairments indicative of autism in three developmental areas: communication and social interactions, restricted interests and activities, and stereotypical behaviors. One of the most widely used instruments is the Autism Diagnostic Observational Schedule-Generic (ADOS-G) (Lord, et al., "The autism diagnostic observation schedule-generic: a standard measure of social and communication deficits associated with the spectrum of autism," *Journal of Autism and Developmental Disorders*, 2000, 30(3): 205-223). The ADOS-G consists of a variety of semi-structured activities designed to measure social interaction, communication, play, and imaginative use of materials. The exam is divided into four modules each geared towards a specific group of individuals based on their level of language and to ensure coverage for wide variety of behavioral manifestations, with module 1, containing 10 activities and 29 items, focused on individuals with little or no language and therefore most typical for assessment of younger children. The ADOS observation is run by a certified professional in a clinical environment and its duration can range from 30 to 60 minutes. Following the observation period, the administrator will then score the individual to determine their ADOS-based diagnosis, increasing the total time from observation through scoring to between 60 to 90 minutes in length.

The long length of the ADOS exam as well as the need for administration in a clinical facility by a trained professional both contribute to delays in diagnosis and an imbalance in coverage of the population needing attention (Wiggins, et al., "Examination of the time between first evaluation and first autism spectrum diagnosis in a population-based sample," *Journal of developmental and behavioral pediatrics, IDBP* 2006, 27(2 Suppl): S79-87). The clinical facilities and trained clinical professionals tend to be geographically clustered in major metropolitan areas and far outnumbered by the individuals in need of clinical evaluation. Families may wait as long as 13 months between initial screening and diagnosis (Lord, et al., "The autism diagnostic observation schedule-generic: a standard measure of social and communication deficits associated with the spectrum of autism," *Journal of Autism and Developmental Disorders*, 2000, 30(3): 205-223) and even longer if part of a minority population or lower socioeconomic status (Bernier, et al., "Psychopathology, families, and culture: autism," *Child Adolesc Psychiatr Clin N Am*, 2010, 19(4):855-867). These delays directly translate into delays in the delivery of speech and behavioral therapies that have significant positive impacts on a child's development, especially when delivered early (Howlin, "Children with Autism and Asperger's Syndrome: A Guide for Practitioners and Parents," Chichester, UK: Wiley; 1998) (Pisula, "Parents of children with autism: review of current research," *Arch Psychiatry Psychother*, 2003, 5:51-63). Thus a large percentage of the population is diagnosed after developmental windows when behavioral therapy would have had maximal impact on future development and quality of life. The average age of diagnosis in the United States is 5.7 years and an estimated 27% remain undiagnosed at 8 years of age. At these late stages in development, many of the opportunities to intervene with therapy have evaporated.

Attention has been paid to the design of abbreviated screening examinations that are meant to foster more rapid diagnosis, including the Autism Screening Questionnaire (ASQ, designed to discriminate between PDD and non-PDD diagnoses (Berument, et al., "Autism screening questionnaire: diagnostic validity," *Br J Psychiatry*, 1999, 175:444-451)), the Modified Checklist for Autism in Toddlers (MCHAT) (Robins, et al., "The Modified Checklist for Autism in Toddlers: an initial study investigating the early detection of autism and pervasive developmental disorders," *J Autism Dev Disord*, 2001, 31(2):131-144), and the Parents' Evaluation of Developmental Status (PEDS) (Pinto-Martin, et al., "Screening strategies for autism spectrum disorders in pediatric primary care," *J Dev Behav Pediatr*, 2008, 29(5): 345-350), to name a few. However, the ADOS, due to its high degree of clinical utility and diagnostic validity, remains one of the dominant behavioral tools for finalizing a clinical diagnosis. Research has focused on manual selection of preferred questions from the full ADOS for use in scoring following the observation period, and while this work has led to critical advances in diagnostic validity and steps toward a reliable measure of severity, no efforts have focused on selection of ADOS questions to enable shortening of the diagnosis process overall.

The aim in the present study was to statistically identify a subset of items from the full ADOS module 1 that could enable faster screening both in and out of clinical settings, but that does not compromise the diagnostic validity of the complete ADOS. As a valuable byproduct of the widespread adoption and use of ADOS-G, research efforts have banked large collections of score sheets from ADOS together with the clinical diagnosis that can be utilized to address this aim directly. Leveraging these large databases, a collection of full ADOS evaluations for over 1,050 children can be collected, focusing on module 1 data alone that provides key insight into the development of shorter approaches for early detection. By application of machine learning methods, classifiers can be constructed and the sensitivity and specificity of each can be objectively measured with respect to diagnostic validity and similarity as compared to the original ADOS-G algorithms. According to the present invention, one classifier, a classifier based on the decision tree learning, performed optimally for classification of a wide range of individuals both on and off the spectrum. This classifier was significantly shorter than the standard ADOS and pinpointed several key areas for behavioral assessment that could guide future methods for observation-based screening and diagnosis in as well as out of clinical settings.

Methods

Constructing a Classifier

ADOS-G Module 1 data from the Autism Genetic Resource Exchange (AGRE) (Geschwind, et al., "The autism genetic resource exchange: a resource for the study of autism and related neuropsychiatric conditions," *American journal of human genetics*, 2001, 69(2):463-466) repository of families with at least one child diagnosed with autism can be used as the input for machine learning classification. The ADOS-G examination classifies individuals into categories of "autism" or "autism spectrum" based on the ADOS-G diagnostic algorithm. The diagnostic algorithm adds up the scores from 12 (original) to 14 (revised) items and classifies individuals as having autism or autism spectrum according to thresholds scores. Those individuals who did not meet the required threshold were classified as "non-spectrum" and were used as controls in the study. For the purposes of the analysis, the analysis can be restricted to only those with the classification of "autism." Any individuals who were untestable or where the majority of their scores were unavailable were excluded from the analysis. The final data matrix contained 612 individuals with a classification of "autism" and 11 individuals with a classification of "non-spectrum" (Table 4).

Table 4 sets forth a summary of the data used for both construction and validation of the autism diagnostic classifier. Complete sets of answers to the Autism Diagnostic Observation Schedule-Generic evaluation can be acquired from the Autism Genetic Research Exchange (AGRE), the Simons Foundation (Simons), and the Boston Autism Consortium (AC). The table lists the total numbers of individuals classified as having autism and individuals classified as non-spectrum represented in each of the three data sets as well as a breakdown of age using the interquartile range.

TABLE 4

|  | AGRE | | AC | | Simons | |
| --- | --- | --- | --- | --- | --- | --- |
|  | Autism | Non-Spectrum | Autism | Non-Spectrum | Autism | Non-Spectrum |
| Sample Size | 612 | 11 | 110 | 4 | 336 | 0 |
| Q1 | 4.7375 | 2.99 | 3.6875 | 2.771 | 5.167 | 0 |
| Median | 6.64 | 4.57 | 5.625 | 3.083 | 6.75 | 0 |
| Q3 | 8.86 | 6.93 | 8.4167 | 6.729 | 10 | 0 |
| IQR | 4.1225 | 3.94 | 4.7292 | 3.958 | 4.833 | 0 |

In the study, a classifier can be constructed by performing a series of machine learning analyses (performed using Weka (Hall, et al., "The WEKA Data Mining Software: An Update," *SIGKDD Explorations*, 2009, 11(1):1)) on the 29 ADOS-G items from module 1 to differentiate between individuals with a classification of "autism" from those with a classification of "non-spectrum." The sensitivity, specificity, and accuracy of 16 machine learning algorithms can be compared to create the best classifier (Table 5).

Table 5 sets forth the 16 machine learning algorithms used to analyze the module 1 ADOS-G data used for training the classifier. These algorithms were executed using the toolkit WEKA. The false positive rate (FPR) and true positive rate (TPR) are provided along with the overall accuracy. Both the Alternating Decision Tree (ADTree) and the functional tree (FT) performed with 100% accuracy. The ADTree can be chosen over the FT for further analysis because the former uses eight items compared to the nine items used in the latter.

TABLE 5

| Classifier Name | Description | FPR | TPR | Accuracy |
| --- | --- | --- | --- | --- |
| ADTree | An ADTree combines decision trees, voted decision trees, and voted decision stumps. The algorithm is based on boosting, which yields accurate predictions by combining a series of "weak" learners that together, can classify accurately (Freund, et al., "The alternating decision tree learning algorithm," In: *Machine Learning: Proceedings of the Sixteenth International Conference 1999*, 124-133). | 0.000 | 1.000 | 1.000 |
| BFTree | The top node of the decision tree splits the data so the maximum reduction of impurity (misclassified data) is achieved. This is called the "best" node, and it is expanded upon first (unlike in a C4.5 tree, for example, where nodes are expanded upon according to depth-first) (Shi, "Best-first Decision Tree Learning," Master Thesis, *The University of Waikato*, 2007). | 0.600 | 0.993 | 0.979 |
| Decision Stump | A DecisionStump classifier is a single-level decision tree with one node. Terminal nodes extend directly off of this node, so a classification is made based on a single attribute (Freund, et al., "Experiments with a new boosting algorithm," In: *Proceedings of the International Conference on Machine Learning: 1996; San Francisco*, Morgan Kautinann: 148-156). | 1.000 | 1.000 | |
| FT | Functional trees are classification trees which can use multiple linear regression or multiple logistic regression at decision nodes and linear models at leaf nodes (Gama J: Functional Trees. Machine Learning 2004, 219-250). | 0.000 | 1.000 | 1.000 |
| J48 | J48 is a Java implementation of the C4.5 algorithm; it generates either pruned or an unpruned or C4.5 decision tree. C4.5 build trees from training data using the concept of information entropy (Quinlan, "C4.5," San Mateo: Morgan Kaufmann Publishers; 1993). | 0.200 | 0.998 | 0.994 |
| J48graft | This class generates a grafted C4.5 decision tree that can either be pruned or unpruned. Grafting adds nodes to already created decision trees to improve accuracy (Freund, et al., "The alternating decision tree learning algorithm," In: *Machine Learning: Proceedings of the Sixteenth International Conference 1999*, 124-133). | 0.333 | 1.000 | 0.992 |
| Jrip | This classifier is an optimized version of Incremental Reduced Error Pruning implementing a propositional learner, RIPPER (Repeated Incremental Pruning to Produce Error Reduction) (Cohen, "Fast Effective Rule Induction," *Twelfth International Conference on Machine Learning*, 1995:115-123). | 0.333 | 0.995 | 0.987 |
| LADTree | LADTree produces a multi-class alternating decision tree. It has the capability to have more than two class inputs. It performs additive logistic regression using the LogitBoost strategy (Holmes, et al., "Multiclass alternating decision trees," *ECML*, 2001:161-172). | 0.133 | 0.997 | 0.994 |

TABLE 5-continued

| Classifier Name | Description | FPR | TPR | Accuracy |
|---|---|---|---|---|
| LMT | Logistic model trees combine decision trees with logistic regression models. LMTs are generated by creating a logistic model at the root using LogitBoost. The tree is extended at child nodes by using LogitBoost. Nodes are split until no additional split can be found (Landwehr, et al., "Logistic Model Trees," *Machine Learning*, 2005, 161-205). | 0.133 | 1.000 | 0.997 |
| Nnge | Nearest neighbor algorithms define a distance function to separate classes. By using generalized exemplars it reduces the role of the distance function (relying too heavily on the distance function can produce inaccurate results) by grouping classes together (Martin, "Instance-Based learning : Nearest Neighbor With Generalization," Hamilton, New Zealand.: University of Waikato; 1995). | 0.200 | 0.998 | 0.994 |
| OneR | This algorithm finds association rules. It finds the one attribute that classifies instances so as to reduce prediction errors (Holte, "Very simple classification rules perform well on most commonly used datasets," *Machine Learning: Proceedings of the Sixteenth International Conference*, 1993, 11:63-91). | 0.400 | 0.993 | 0.984 |
| PART | A set of rules is generated using the "divide-and-conquer" strategy. From here, all instances in the training data that are covered by this rule get removed and this process is repeated until no instances remain (Frank, et al., "Generating Accurate Rule Sets Without Global Optimization," In: *Machine Learning: Proceedings of the Fifteenth International Conference: 1998; San Francisco, CA, Morgan Kaufmann Publishers*). | 0.200 | 1.000 | 0.995 |
| RandomTree | The RandomTree classifier draws trees at random from a set of possible trees with k random features at each node and performs no pruning (Breiman, "Random Forest," *Machine Learning*, 2001, 45: 5-32). | 0.400 | 0.987 | 0.978 |
| REPTree | An REPTree is a fast decision tree learner that constructs a decision/regression tree using information gain for splitting, and prunes the tree using reduced-error pruning with backfitting (Witten, et al., "Data Mining: Practical Machine Learning Tools and Techniques with Java Implementations," Morgan Kaufmann, Amsterdam [etc.], second edition, October 2005). | 0.467 | 0.998 | 0.987 |
| Ridor | This classifier is an implementation of a Ripple-Down Rule Learner. An example of this is when the classifier picks a default rule (based on the least weighted error), and creates exception cases stemming from this one (Gaines, et al., "Induction of Ripple-Down Rules Applied to Modeling Large Databases," *J Intell Inf Syst*, 1995, 5(3):211-228). | 0.267 | 0.997 | 0.990 |
| Simple Cart | Classification and regression trees are used to construct prediction models for data. They are made by partitioning the data and fitting models to each partition (Breiman, et al., "Classification and Regression Trees," *Wadsworth International Group, Belmont, California*, 1984). | 0.667 | 0.992 | 0.976 |

For each algorithm, 10-fold cross-validation can be used, utilizing 90% for training and the remaining 10% for testing to construct and measure the accuracy of the resulting classifier. This procedure has been previously shown to perform optimally for structured, labeled data while reducing bias in the resulting classifier (Kohavi, "A study of cross-validation and bootstrap for accuracy estimation and model selection," In: *Proceedings IJCAI-95*: 1995; Montreal, Morgan Kaufmann, Los Altos, Calif.: 11374). The specificity of the classifiers can be plotted against its sensitivity to visualize the performance as well as to determine the most accurate classifier for each module.

Validating the Classifier

Beyond the 10-fold cross-validation, the classifier can be validated by testing it on independently collected ADOS-G data from other individuals with autism in the Boston Autism Consortium (AC) and the Simons Simplex Collection (Fischbach, et al., "The Simons Simplex Collection: a resource for identification of autism genetic risk factors," *Neuron,* 2010, 68(2):192-195) (SSC). The AC data included 110 individuals classified by the ADOS-G module 1 algorithm as "autistic" and an additional four individuals who were considered "non-spectrum." The SSC data comprised 336 individuals classified as "autistic" and no individuals who were found to be off the spectrum following the ADOS exam.

Balancing Classes Through Simulation

Because machine learning algorithms maximize performance criteria that place equal weight on each data point without regard to class distinctions, controls can be simulated to increase the number of score sheets that correspond to an ADOS-G classification of "non spectrum." This enabled a test as to whether the imbalance in the classes of autism and non-spectrum inadvertently introduced biases that skew downstream results and interpretation. To create a simulated control, scores can be randomly sampled from the existing set of 15 controls, i.e., the total number of individuals who did not meet the criteria for a classification of "autism" in all three studies. The simulated control can be done for each of the 29 items in the ADOS-G module 1 by randomly drawing from the set of recorded scores for that item. This guaranteed that the simulated scores were drawn from the same distribution of observed scores. This process was repeated 1,000 times to create artificial controls that were subsequently used to further challenge the specificity of the classifier, i.e., its ability to correctly categorize individuals with atypical development or apparent risk of neurodevelopmental delay but not on the autism spectrum. The simulated controls can be utilized to recreate a classifier based on data with balanced classes, 612 observed ADOS-G score sheets for individuals categorized as having autism and 612 individuals (15 observed+597 simulated) not meeting ADOS-G criteria for an autism diagnosis.

Results

The classifier can be constructed for module 1 using ADOS-G data from the Autism Genetic Resource Exchange (AGRE). Because the AGRE data contained only 11 controls for module 1, all other module 1 individuals can be included with a classification of "non-spectrum" from the Boston Autism Consortium (AC) in the analysis bringing the total number of controls up to 15. The accuracy of the classifier can be improved when compared to the accuracy of only using the 11 controls from AGRE. The performance of 16 different machine learning algorithms on the 29 items in module 1 (Table 5) can be tested. The best algorithm can be selected by comparing the sensitivity, specificity, and accuracy (FIG. 4).

Figure 4:
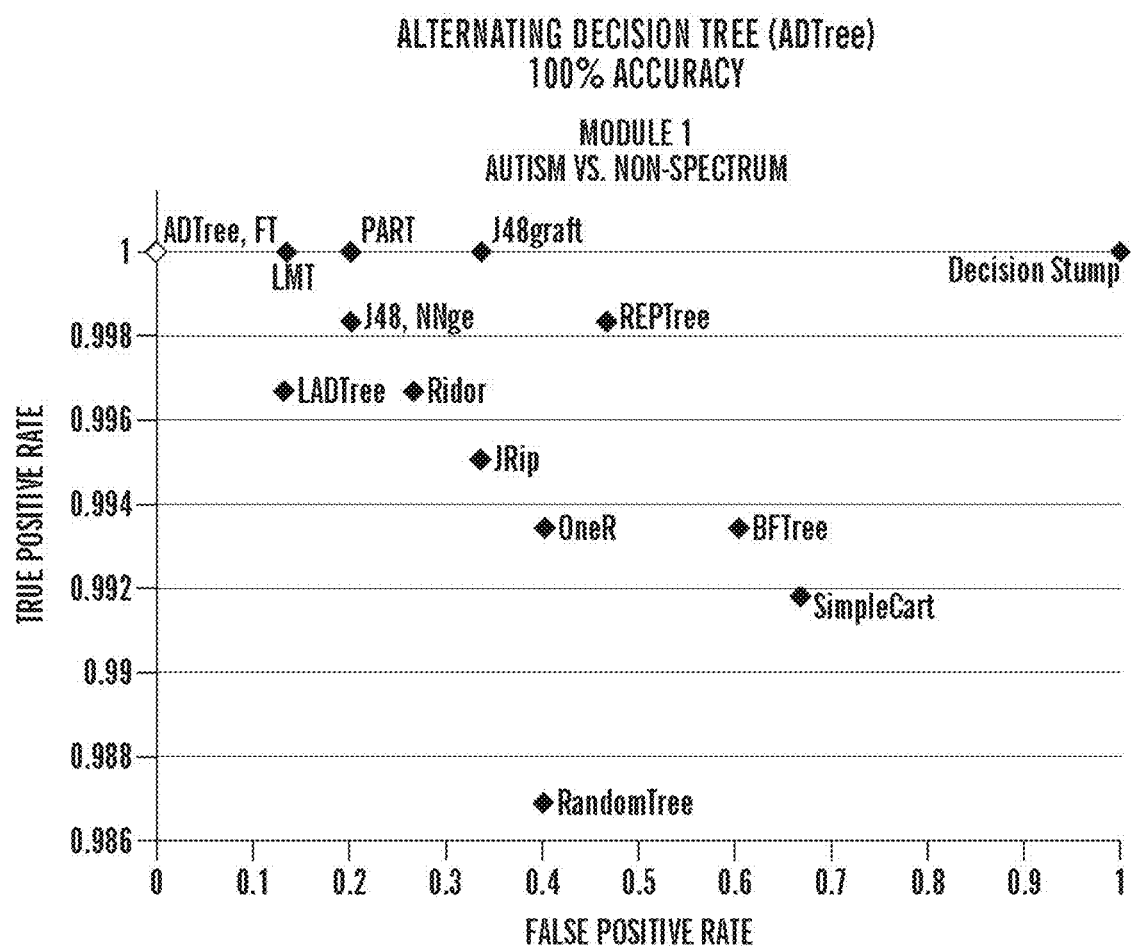
FIG. 4 is a chart showing performance of all 15 machine learning algorithms evaluated for classifying autism cases versus controls (ADOS)

FIG. 4 shows receiver operator curves mapping sensitivity versus specificity for the 16 different machine learning algorithms tested on the module 1 Autism Diagnostic Observational Schedule-Generic (ADOS-G) training data. The best classifiers can be identified as those closest to the point (1, 0) on the graph indicating perfect sensitivity (true positive rate) and 1-specificity (false positive rate). The best performing model was the alternating decision tree (ADTree) and functional tree (FT). The ADTree was chosen over the FT because it used fewer items. See Table 5 for a summary of the 16 machine learning algorithms used in the analysis.

For module 1, two algorithms, the alternating decision tree (Freund, et al., "The alternating decision tree learning algorithm," In: *Machine Learning: Proceedings of the Sixteenth International Conference* 1999, 124-133) and the functional tree (Gama J: Functional Trees. Machine Learning 2004, 219-250), operated with perfect sensitivity, specificity, and accuracy. However, the alternating decision tree used eight questions while the functional tree used nine. Because it is the goal to shorten the exam without appreciable loss of accuracy, the alternating decision tree (ADTree) can be selected as the optimum algorithm for further analysis and validation. The ADTree classifier correctly classifies all 612 individuals from AGRE who previously received a designation of "autism" by the ADOS-G module 1 algorithm as well as all 15 individuals from AGRE and AC who were given a classification of "non-spectrum" by the ADOS-G module 1 algorithm. The ADTree classifier consisted of only eight items out of the 29 used in the analysis. Those eight items included A2, B1, B2, B5, B9, B10, C1, and C2 (Table 6).

Table 6 shows the eight items used in the ADTree model. Listed are the question code used by Autism Genetic Research Exchange (AGRE), a brief description of the question, and the domain to which the question belongs.

TABLE 6

| Question Code | Question subject | Core Domain |
| --- | --- | --- |
| A2 | Frequency of Vocalization Directed to Others | Communication |
| B1 | Unusual Eye Contact | Social Interaction |
| B2 | Responsive Social Smile | Social Interaction |
| B5 | Shared Enjoyment in Interaction | Social Interaction |
| B9 | Showing | Social Interaction |
| B10 | Spontaneous Initiation of Joint Attention | Social Interaction |
| C1 | Functional Play with Objects | Play |
| C2 | Imagination/Creativity | Play |

These eight items segregated into two of three main functional domains associated with autism, language/communication and social interactions, both important indicators of autism. Item A2 (vocalization directed to others) corresponded to the language and communication domain. Items B1 (unusual eye contact), B2 (responsive social smile), B5 (shared enjoyment in interaction), B9 (showing), and B10 (spontaneous initiation of joint attention) all correspond to the domain of social interaction. Items C1 (Functional Play) and C2 (Imagination/Creativity) were designed to assess how a child plays with objects. The eight items form the elements of a decision tree that enabled classification of either "autism" or "non-spectrum" (FIG. 5).

Figure 5:
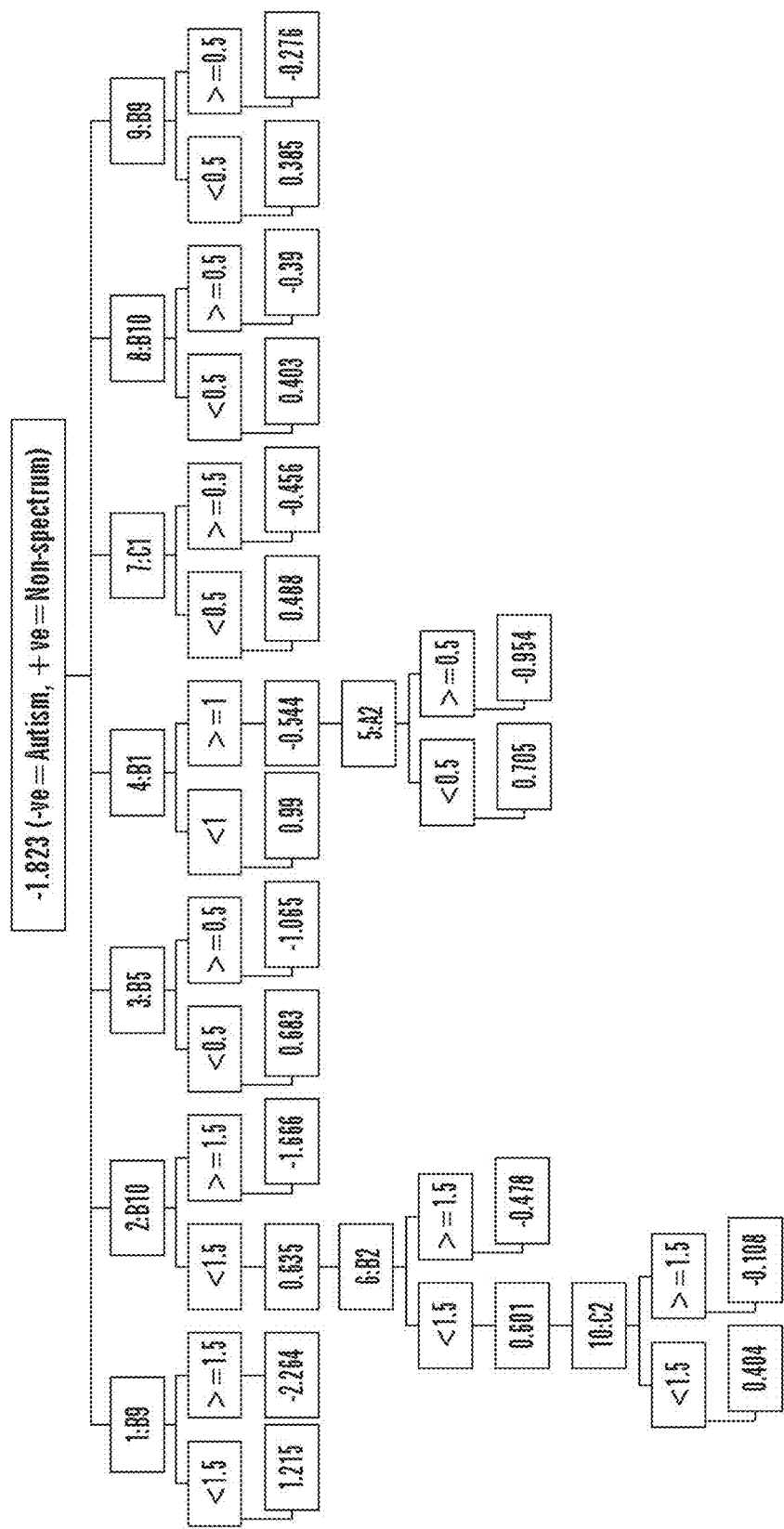
FIG. 5 shows an example of a decision tree for a video-based classifier (VBC)

FIG. 5 is a decision tree and official behavioral classifier generated by the Alternating Decision Tree (ADTree) algorithm of the present invention. The ADTree was found to perform best out of 16 different machine learning approaches (FIG. 4, Table 5). The resulting tree enables one to follow each path originating from the top node, sum the prediction values and then use the sign to determine the class. In this case, a negative sum yielded the classification of autism while a positive sum yielded the classification of non-spectrum. Additionally, the magnitude of the sum is an indicator of prediction confidence.

Two items appeared more than once in the tree (B9 and B10), which supported the possibility that these items play a relatively more important role in arriving at a classification of autism and that the domain of social interaction can have more utility in the observational-based screening and diagnosis of autism. Each item in the tree either increased or decreased a running total score known as the ADTree score. A negative score indicated a classification of "autism" while a positive score yielded the classification "not-spectrum." Importantly, the amplitude of the score provided a measure of confidence in the classification outcome, with larger absolute values indicating higher confidence overall, as previously indicated in Freund (Freund, et al., "A decision-theoretic generalization of on-line learning and an application to boosting," *Journal of Computer and System Sciences*, 1997, 55, 119-139). In the study, the vast majority of the scores were away from the borderline for both the case and control classes (FIG. 6) indicating that the predictions made by the classifier were by-and-large robust and unambiguous.

Figure 6:
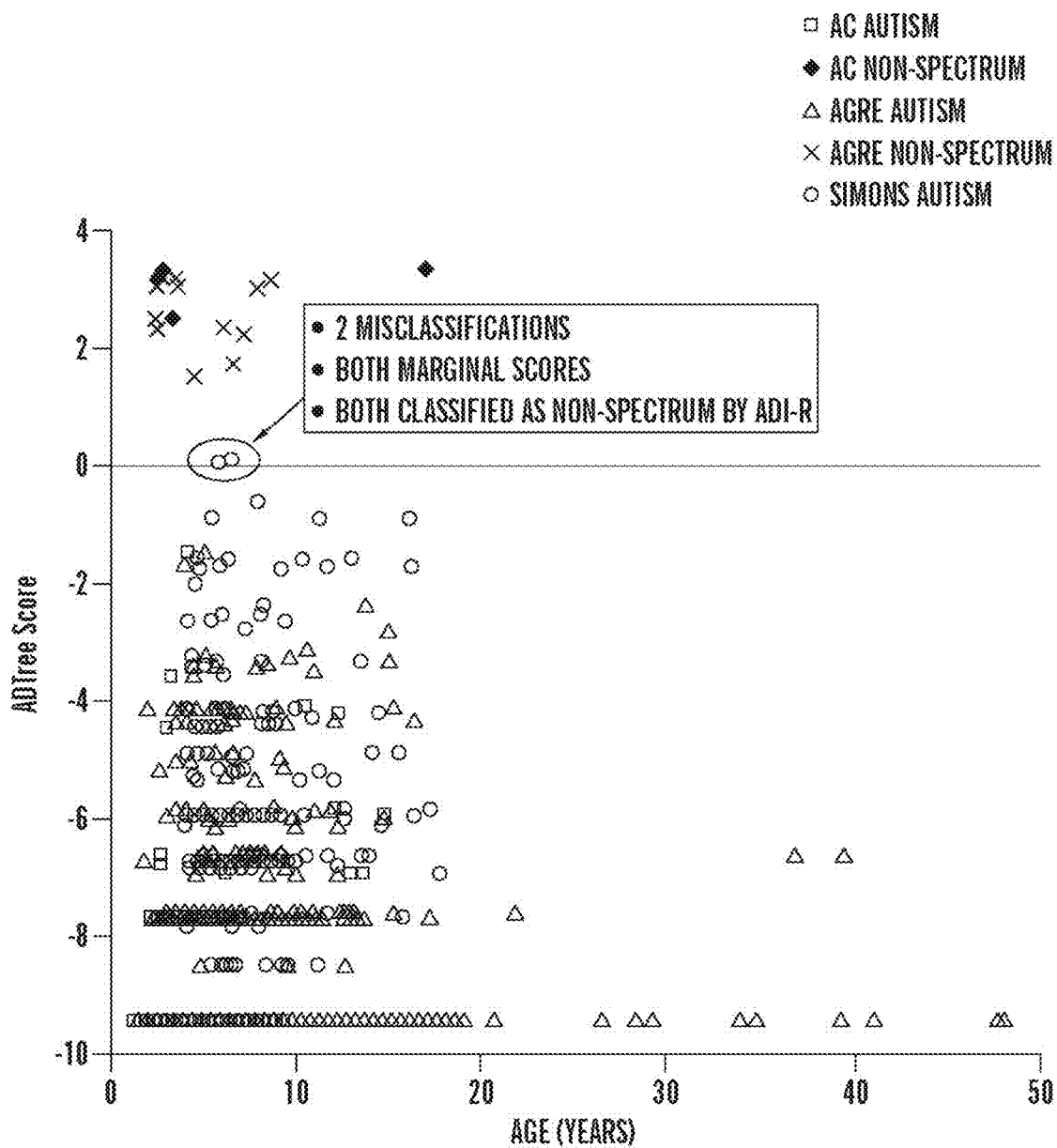
FIG. 6 is a chart showing validation and coverage (ADI-R)

FIG. 6 is a graph showing the Alternating Decision Tree (ADTree) scores of individuals in the Autism Genetic Resource Exchange, Boston Autism Consortium, and Simons Simplex Collection data sets versus their age in years. A majority of the ADTree scores are clustered towards greater magnitudes according to their respective classifications, regardless of age.

For independent validation of the 8-question classifier, score sheets can be collected for module 1 from the Boston Autism Consortium (AC) and Simons Simplex Collection (SSC). Here the objective was to determine in the classifier could correctly recapitulate the diagnosis, autism vs. not, provided by the ADOS-G assessments of the individuals recruited to these two independent studies. The classifier correctly classified all 110 individuals previously diagnosed with "autism" in AC as well as all four controls as "non-spectrum." The classifier also performed with high accuracy on the SSC dataset misclassifying only two of 336 individuals given a classification of "autism" in the original SSC (99.7% accuracy). Upon further examination of the two misclassified individuals from SSC, their ADTree scores were near zero, at 0.1 and 0.039. These low-confidence scores strongly suggested that the classifications should be questioned and that additional, more rigorous assessment of these two individuals would likely lead to a reversal of their diagnosis.

Due to the limited number of controls in module 1, 1,000 controls can be simulated by randomly sampling from the group of observed answers in the 15 individuals classified as "non-spectrum." This procedure enables construction of a series of artificial score sheets for the ADOS-G module 1 that were within the bounds of answers likely to be provided by prospectively recruited individuals who would not receive a diagnosis of autism following an ADOS-G exam. The classifier correctly classified 944 out of the 1,000 simulated controls (94.4% accuracy). Upon looking closer at the 56 simulated individuals who were given an incorrect classification of "autism" instead of "non-spectrum," all but six of them had ADTree scores less than one point away from receiving a classification of "non-spectrum." Had these been real individuals, further screening and additional diagnostic tests can be suggested to determine if the ADTree classification was correct or not.

Because of the small number of controls and imbalance in the numbers of cases and controls, a machine learning procedure called upsampling can be performed to assess and rule out biases in the original classifier. Upsampling effectively balances the numbers of cases and controls by progressive sampling from the population of observed data. A classifier can be constructed using the ADTree algorithm with the 612 individuals with a classification of "autism" from AGRE and 612 individuals with a classification of "non-spectrum" of which 11 were from AGRE, four were from AC, and the remaining 597 were from the simulated controls. The resulting classifier correctly classified 609 out of the 612 individuals with autism and all 612 individuals with a classification of "non-spectrum" (99.8% accuracy). The resulting ADTree consisted of seven items, six of which were also in the original classifier derived from imbalanced data. Additionally, the ensuing alternating decision tree closely resembled that of the original (FIG. 7), lending further support for the robustness of the classifier and supporting the notion that the imbalance of classes did not introduce appreciable bias in the results.

Figure 7:
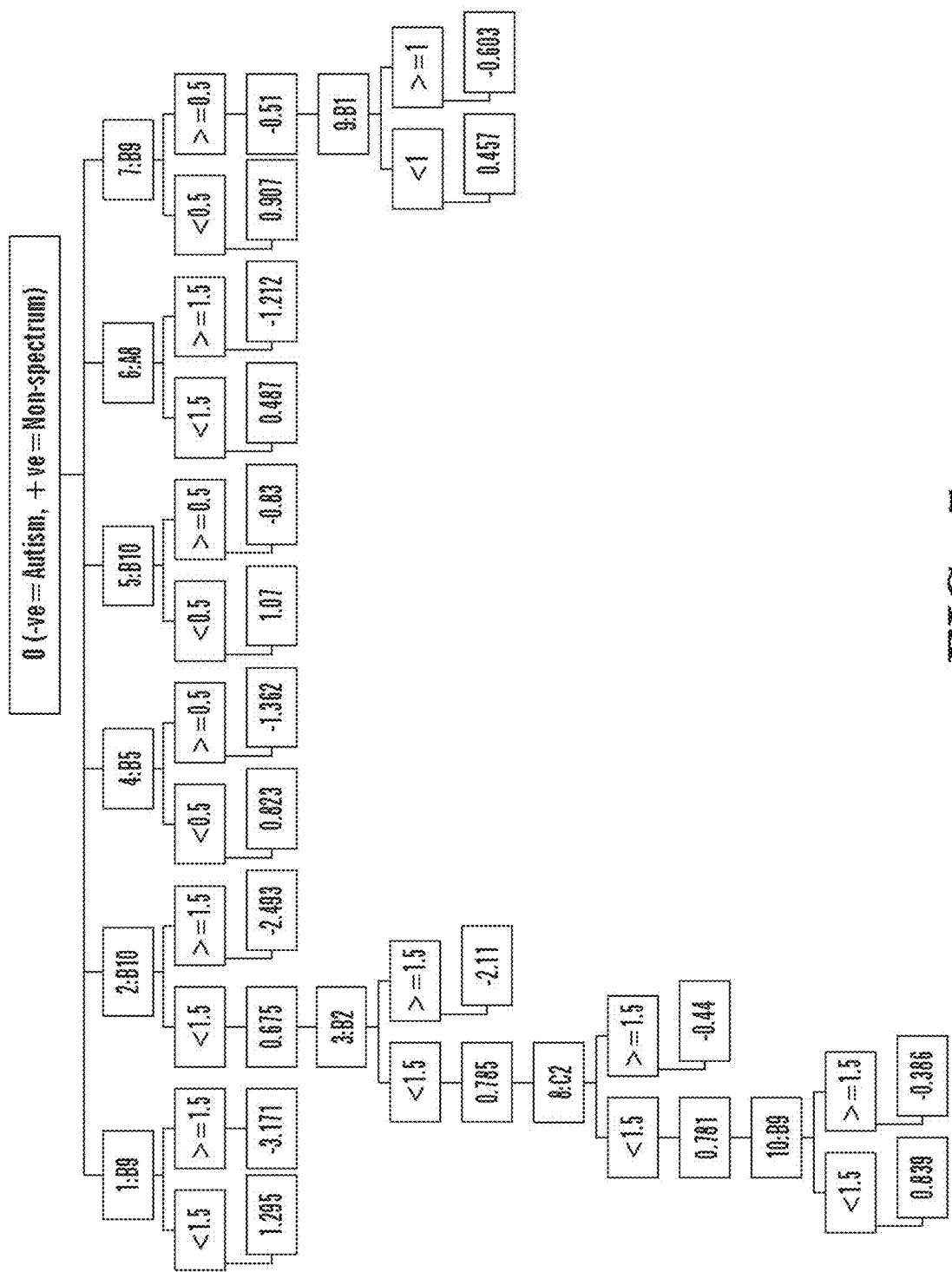
FIG. 7 shows an example of a decision tree for a classifier generated by the Alternating Decision Tree (ADTree) algorithm when applied to upsampling the controls.

FIG. 7 is a decision tree and classifier generated by the Alternating Decision Tree (ADTree) algorithm when applied to upsampling the controls. The resulting tree closely resembles that of the original tree (FIG. 5). The general shape of the tree remains the same, e.g., the left branch is nearly identical to the original.

Current practices for the behavioral diagnosis of autism can be effective but in many cases overly prohibitive and time consuming. One of the most widely used instruments in the field of autism spectrum disorders is the Autism Diagnostic Observational Schedule-Generic (ADOS-G), an exam broken up into four modules to accommodate a wide variety of individuals. Machine learning techniques can be used to determine if the classification accuracy of the full ADOS-G could be achieved with a shorter version of the exam. The analysis found a small subset of eight ADOS-G questions from module 1 targeting social, communication, and language abilities to be 99.8% as effective as the full ADOS-G module 1 algorithm for classifying 1,058 individuals with autism and 15 individuals classified as "non-spectrum" drawn from three independent repositories. This eight-item classifier represents a 72.4% reduction of the full module 1 ADOS-G exam.

The objective reduction in the number of items from the module 1 version of ADOS-G also enabled a logical reduction in the activities associated with the exam. Module 1 contains ten activities (Table 7) each designed to elicit specific behaviors and responses that are coded in the 29 items. With the reduction of the number of items from 29 to 8, 2 of the 10 activities, namely "response to name" and "response to joint attention" could be immediately eliminated as neither are required for the 8-question classifier (Table 7).

Table 7 shows the ten activities used in the original module 1 ADOS-G examination. Listed are the name of the activity and whether or not the activity still remains relevant after removing 21 of the 29 items from the original ADOS-G module 1.

TABLE 7

| Activity | Keep? |
| --- | --- |
| Free Play | Yes |
| Response to Name | No |
| Response to Joint Attention | No |
| Bubble Play | Yes |
| Anticipation of a Routine with Objects | Yes |
| Responsive Social Smile | Yes |
| Anticipation of a Social Routine | Yes |
| Functional and Symbolic Imitation | Yes |
| Birthday Party | Yes |
| Snack | Yes |

If one makes the rough assumption that each activity requires the same amount of time to administer, then this reduction of activities would correspond to minimum time reduction of 20%. This means that the exam will take on average 24 to 48 minutes instead of 30 to 60 minutes. However, because there are fewer items to score, it is feasible that the child will exhibit all behaviors required to score the eight items well before carrying out all eight activities. Under such circumstances, the exam would conceivably take significantly less time that the 20% reduction predicted from the above assumptions.

The analysis used machine learning techniques to analyze previous collections of data from individuals with autism, a practice that currently has not been commonplace in the field, but one that promotes novel and objective interpretation of autism data and promotes the development of an improved understanding of the autism phenotype. In the present case, several alternative machine learning strategies of the present invention yielded classifiers with very high accuracy and low rates of false positives. The top performing ADTree algorithm proved most valuable for classification as well as for measuring classification confidence, with a nearly 100% accuracy in the diagnosis of individuals with autism across three repositories. The ADTree algorithm resulted in a simple decision tree (FIG. 5) that can, according to the present invention, be easily converted into a behavioral algorithm for use in both screening and/or diagnostic settings. Additionally, it can, according to the present invention, be used to inform mobile health approaches, for example, through a web-based video screening tools (for example, like the web-based video screening tools according to the present invention hosted on the Harvard Autworks website). In addition, the ADTree score provided an empirical measure of confidence in the classification that can flag borderline individuals likely warranting closer inspection and further behavioral assessment. In the present case, a small number of controls were misclassified, but their low-confidence scores suggested further screening and additional diagnostic tests would result in a correct diagnosis.

An exam that preserves the reliability of the ADOS-G but can be administered in less time enables more rapid diagnosis, higher throughput, as well as timely and more impactful delivery of therapy.

Limitations

The study was limited by the content of existing repositories, that, for reasons related to the recruitment processes of those studies, contain very few individuals who did not meet the criteria for an autism diagnosis based on ADOS-G. In a prospective design for a study according to the invention, one would normally include equal numbers of cases and controls for optimal calculations of sensitivity and specificity of the classifier. The validation can be expanded through the inclusion of new ADOS-G data from both individuals with autism and individuals without autism.

Again because of limitations in available data, the classifier was trained only on individuals with or without classic autism. With sufficient data, the present invention may be adapted to test whether the classifier could accurately distinguish between autism, Asperger's syndrome, and Pervasive Developmental Disorder-Not Otherwise Specified (PDD-NOS). Those individuals not meeting the formal criteria for autism diagnosis were generally recruited to the study as high-risk individuals or as siblings of an individual with autism. Thus, these controls may have milder neurodevelopmental abnormalities that correspond to other categories outside of classic autism. Given that the classifier generally performed well at distinguishing these individuals from those with classic autism supports the possibility that the classifier already has inherent sensitivity to behavioral variants within, and outside, of the autism spectrum. Additional ADOS-G data from a range of individuals with autism spectrum disorders enables measurement of the value beyond that of classic autism as well as enables retraining of the classifier if the accuracy is low.

Conclusions

Currently, autism is diagnosed through behavioral exams and questionnaires that require significant time investment for both parents and clinicians. In the study, the amount of time required to take one of the most widely used instruments for behavioral diagnosis, the autism diagnostic observation schedule-generic (ADOS-G), can be reduced. Using machine learning algorithms according to the present invention, the alternating decision tree performs with almost perfect sensitivity, specificity, and accuracy in distinguishing individuals with autism from individuals without autism. The alternating decision tree classifier consisted of eight questions, 72.4% fewer than the full ADOS-G, and performed with greater than 99% accuracy when applied to independent populations of individuals with autism misclassifying only two out of 446 cases. Given this dramatic reduction in the number of items without a considerable loss in accuracy, the findings represent an important step forward in making the diagnosis of autism a process of minutes rather than hours, thereby allowing families to receive vital care far earlier in their child's development than under current diagnostic modalities.

Part III: Diagnosis of Autism with Reduced Testing

The present disclosure provides, in some embodiments, methods for diagnosing autism, such as but not limited to, autism spectrum disorder. In some embodiments, the methods are carried out by a computer, which includes all electronic devices having a processor capable of executing program instructions. Computer-readable medium containing instructions to carry out the methods are also disclosed, along with computational apparatuses for carrying out the methods. Accordingly, all features disclosed for the provided methods are also applicable to the media and computational apparatuses.

Thus, one embodiment of the present disclosure provides a method for diagnosing autism, comprising determining whether a subject suffers from autism with a multivariate mathematical algorithm taking a plurality of measurements (e.g., input to an algorithm, which can be descriptions of observed behavior in the format that the algorithm requires, the answers to questions about observed behaviors in the format that the algorithm requires, observations or questions) as input, wherein the plurality:

(a) comprises no more than 25, or alternatively 20, 19, 18, 17, 16, 15, 14, 13, 12, 11, 10, 9 or 8 measurement items selected from the Autism Diagnostic Observation Schedule-Generic (ADOS-G) first module, (b) does not include measurement items based on the "response to name" activity of the ADOS-G first module, or (c) does not include measurement items based on the "response to joint attention" activity of the ADOS-G first module, and (d) wherein the determination is performed by a computer suitably programmed therefor.

In one aspect, the method further comprises taking the plurality of measurements from the subject. In another aspect, the measurements are taken on a video clip. In some embodiments, therefore, the video clip includes observation of a patient in a non-clinical environment, such as home. In some embodiments, the patient being video recorded is asked a number of questions that are determined to be suitable for diagnosing autism in the patient by the present disclosure. In one aspect, the video clip is shorter than about 10 minutes. In another aspect, the video clip is between about 2 and 5 minutes long. In certain embodiments, the video clips are recorded and/or displayed on a mobile device, or displayed using a web interface.

In one aspect, the plurality comprises no more than 8 measurement items selected from the ADOS-G first module.

In another aspect, the plurality comprises at least 5 measurement items selected from the ADOS-G first module.

In one aspect, the plurality does not include measurement items based on the "response to name" activity or the "response to joint attention" activity of the ADOS-G first module.

In one aspect, the plurality comprises at least 5 types of activities of the ADOS-G first module. In another aspect, the plurality consists essentially of measurements items selected from the ADOS-G first module.

In some embodiments, the multivariate mathematical algorithm comprises alternating decision tree (ADTree), or any machine learning methods or statistical methods suitable for the diagnosis, which can be ascertained with methods known in the art.

In one aspect, the determination achieves a greater than about 95% prediction accuracy. In another aspect, the determination achieves a greater than 95% specificity and a greater than 95% sensitivity.

In a particular aspect, the measurement items selected from the ADOS-G first module consist of:
Frequency of Vocalization Directed to Others (A2);
Unusual Eye Contact (B1);
Responsive Social Smile (B2);
Shared Enjoyment in Interaction (B5); Showing (B9);
Spontaneous Initiation of Joint Attention (B10);
Functional Play with Objects (C1); and Imagination/Creativity (C2).

Also provided is a non-transitory computer-readable medium comprising program code for diagnosing autism, which program code, when executed, determines whether a subject suffers from autism with a multivariate mathematical algorithm taking a plurality of measurements as input, wherein the plurality:
(a) comprises no more than 15 measurement items selected from the Autism Diagnostic Observation Schedule-Generic (ADOS-G) first module,
(b) does not include measurement items based on the "response to name" activity of the ADOS-G first module, or
(c) does not include measurement items based on the "response to joint attention" activity of the ADOS-G first module.

Still further provided is a custom computing apparatus for diagnosing autism, comprising:
a processor;
a memory coupled to the processor;
a storage medium in communication with the memory and the processor, the storage medium containing a set of processor executable instructions that, when executed by the processor configure the custom computing apparatus to determine whether a subject suffers from autism with a multivariate mathematical algorithm taking a plurality of measurements as input, wherein the plurality:
(a) comprises no more than 15 measurement items selected from the Autism Diagnostic Observation Schedule-Generic (ADOS-G) first module,
(b) does not include measurement items based on the "response to name" activity of the ADOS-G first module, or
(c) does not include measurement items based on the "response to joint attention" activity of the ADOS-G first module.

As provided, all features disclosed for the provided methods are also applicable to the media and computational apparatuses.

Another embodiment of the present disclosure provides a method for diagnosing autism, comprising determining whether a subject suffers from autism with a multivariate mathematical algorithm taking a plurality of measurements as input, wherein the plurality comprises no more than 50, or alternatively 40, 30, 20, 15, 14, 13, 12, 11, 10, 9, 8 or 7 measurement items or questions selected from the Autism Diagnostic Interview-Revised (ADI-R) exam, and wherein the determination is performed by a computer suitably programmed therefor.

In one aspect, the method further comprises taking the plurality of measurements from the subject. In another aspect, the measurements are taken on a video clip. In some embodiments, therefore, the video clip includes observation of a patient in a non-clinical environment, such as home. In some embodiments, the patient being video recorded is asked a number of questions that are determined to be suitable for diagnosing autism in the patient by the present disclosure. In one aspect, the video clip is shorter than about 10 minutes. In another aspect, the video clip is between about 2 and 5 minutes long. In certain embodiments, the video clips is recorded and/or displayed on a mobile device, or displayed on a web interface.

In one aspect, the plurality comprises no more than 7 measurement items or questions selected from the ADI-R exam. In another aspect, the plurality comprises at least 5 measurement items or questions selected from the ADI-R exam. In yet another aspect, the plurality consists essentially of measurements items or questions selected from the ADI-R exam.

In some embodiments, the multivariate mathematical algorithm comprises alternating decision tree (ADTree), or any machine learning methods or statistical methods suitable for the diagnosis, which can be ascertained with methods known in the art.

In one aspect, the determination achieves a greater than about 95% prediction accuracy. In another aspect, the determination achieves a greater than 95% specificity and a greater than 95% sensitivity.

In a particular aspect, the measurement items or questions selected from the ADI-R exam consist of:
Comprehension of simple language: answer most abnormal between 4 and 5 (comps15);
Reciprocal conversation (within subject's level of language): answer if ever (when verbal) (conver5);
Imaginative play: answer most abnormal between 4 and 5 (play5);
Imaginative play with peers: answer most abnormal between 4 and 5 (peerp15);
Direct gaze: answer most abnormal between 4 and 5 (gazes);
Group play with peers: answer most abnormal between 4 and 5 (grplay5); and
Age when abnormality first evident (ageabn).

Also provided is a non-transitory computer-readable medium comprising program code for diagnosing autism, which program code, when executed, determines whether a subject suffers from autism with a multivariate mathematical algorithm taking a plurality of measurements as input, wherein the plurality comprises no more than 20 measurement items or questions selected from the Autism Diagnostic Interview-Revised (ADI-R) exam.

Still also provided is a custom computing apparatus for diagnosing autism, comprising:
a processor;
a memory coupled to the processor;
a storage medium in communication with the memory and the processor, the storage medium containing a set of processor executable instructions that, when executed by the processor configure the custom computing apparatus to determine whether a subject suffers from autism with a multivariate mathematical algorithm taking a plurality of measurements as input, wherein the plurality comprises no more than 20 measurement items or questions selected from the Autism Diagnostic Interview-Revised (ADI-R) exam.

As provided, all features disclosed for the provided methods are also applicable to the media and computational apparatuses.

Unless otherwise defined, all technical and scientific terms used herein have the same meaning as commonly understood by one of ordinary skill in the art to which this disclosure belongs.

The disclosures illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed.

Thus, it should be understood that although the present disclosure has been specifically disclosed by preferred embodiments and optional features, modification, improvement and variation of the disclosures embodied therein herein disclosed may be resorted to by those skilled in the art, and that such modifications, improvements and variations are considered to be within the scope of this disclosure. The materials, methods, and examples provided here are representative of preferred embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

Part IV: Shortening the Behavioral Diagnosis of Autism Through Artificial Intelligence and Mobile Health Technologies Details on initial methods to shorten the behavioral diagnosis of autism are provided below. Data were collected from three primary sources: AGRE, SSC, AC (see, Table 8, below).

TABLE 8

| | | ADI-R | | | ADOS | |
|---|---|---|---|---|---|---|
| AGRE | | Autism | Not Met | | Autism | Not Met |
| | Total | 891 | 75 | Total | 612 | 11 |
| | Age | 4.4 | 5.5 | Age | 4.1 | 3.9 |
| SSC | | Autism | Not Met | | Autism | Not Met |
| | Total | 1,654 | 4 | Total | 336 | 0 |
| | Age | 4.5 | 3.8 | Age | 4.8 | N/A |
| AC | | Autism | Not Met | | Autism | Not Met |
| | Total | 308 | 2 | Total | 110 | 4 |
| | Age | 5.04 | 8.17 | Age | 4.7 | 3.9 |

Figure 8:
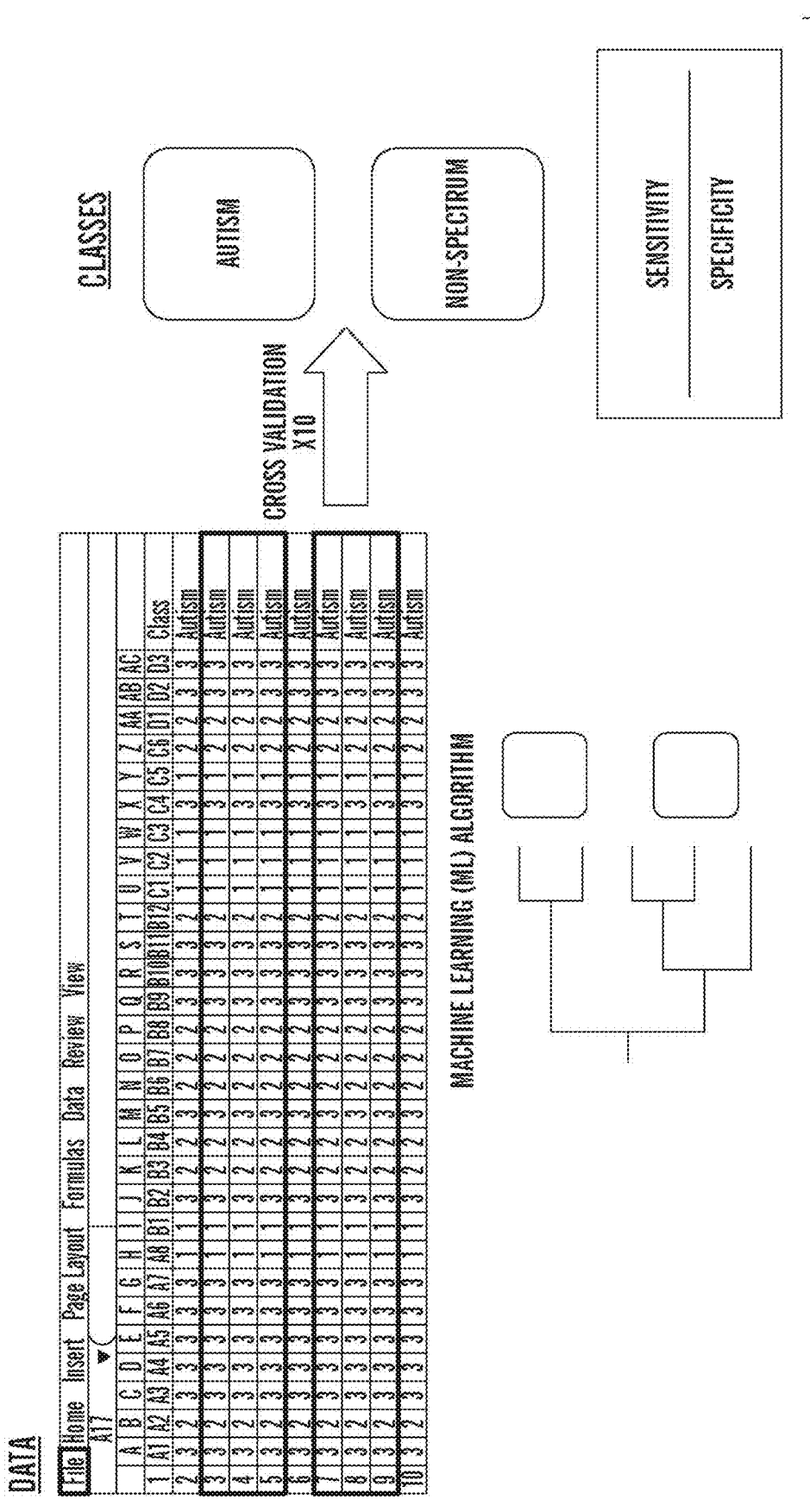
FIG. 8 is a block diagram demonstrating the input of data, analysis of data using machine learning (ML) algorithm(s), cross validation (such as 10-fold cross validation), classification of the data into two broad categories and goal of maintaining sensitivity and specificity.

A subset of the data was used for training and testing of a classifier (applying Artificial Intelligence, FIG. 8). The resulting classifier was found to contain 7 total elements and to have a testing sensitivity of 100% and testing specificity of 99.1% (see, Table 9). The classifier was then applied to the remaining data in the above table to validate the testing results. The accuracy of this newly derived parent-directed classifier was well over 90% in all tests.

An ML Algorithm Performance caregiver-directed classifier is shown, for example, in FIG. 1. A caregiver-directed classifier is shown, for example, in FIG. 2.

Table 9 shows seven questions that achieve high accuracy in ASD detection based on these tests.

TABLE 9

| Question | Code | Subject |
|---|---|---|
| 29 | compsl5 | comprehension of simple language |
| 35 | conver5 | reciprocal conversation |
| 48 | play5 | imaginative play |
| 49 | peerpl5 | imaginative play with peers |
| 50 | gaze5 | direct gaze |
| 64 | grplay5 | group play with peers |
| 86 | ageabn | age when abnormality first evident |

These seven questions translate into a complexity reduction of 93% with no loss in accuracy and also reduce exam time from 2.5 hours to less than 5 minutes.

Next, a validation of the ADI-R, which was modified according to the present invention, was performed.

Table 10 shows application of the 7 question "classifier" to new data.

TABLE 10

| | Autism | Non-Spectrum |
|---|---|---|
| SSC | 1,654/1,654 | 77/84 |
| | 100% | 92% |
| AC | 321/322 | |
| | 99.7% | |
| | Sensitivity | Specificity |

Validation and coverage for a caregiver-directed classifier is shown, for example, in FIG. 3. Seven subjects were misclassified with autism, five had previous diagnosis, all seven met criteria for autism using another trusted autism screener and the classifier was apparently valuable over a wide range of subject ages from 13 months to 45 years.

Figure 9:
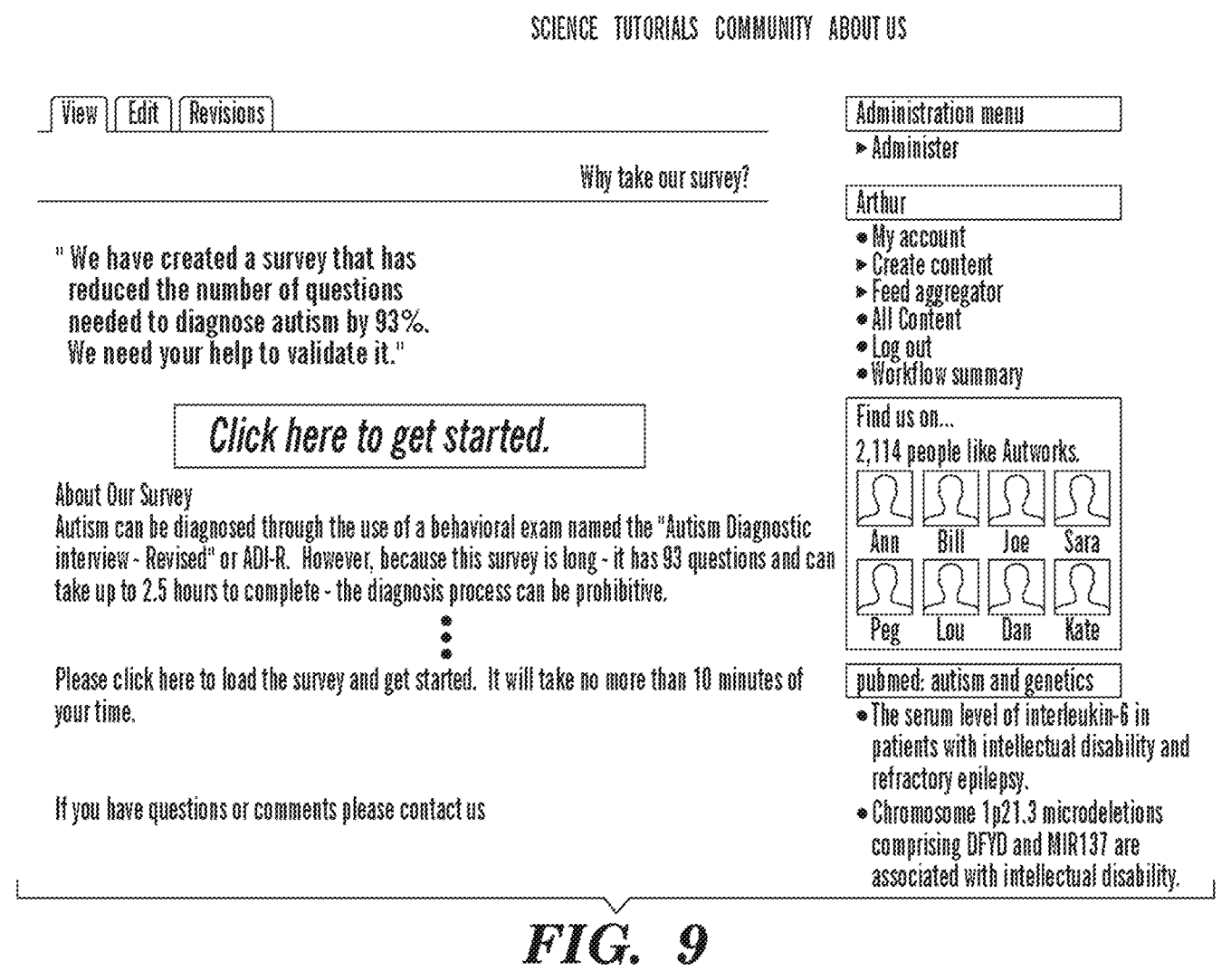

The invention can utilize social networks to prospectively recruit families with autism into the study to further validate the accuracy of this reduced testing tool (see FIG. 9 and FIG. 10). FIG. 9 shows an example of a home page for a website utilizing the present invention. The website includes a prompt to start a survey. FIG. 10 shows an example of a welcome page and consent form for the web site utilizing the present invention.

Figure 11:
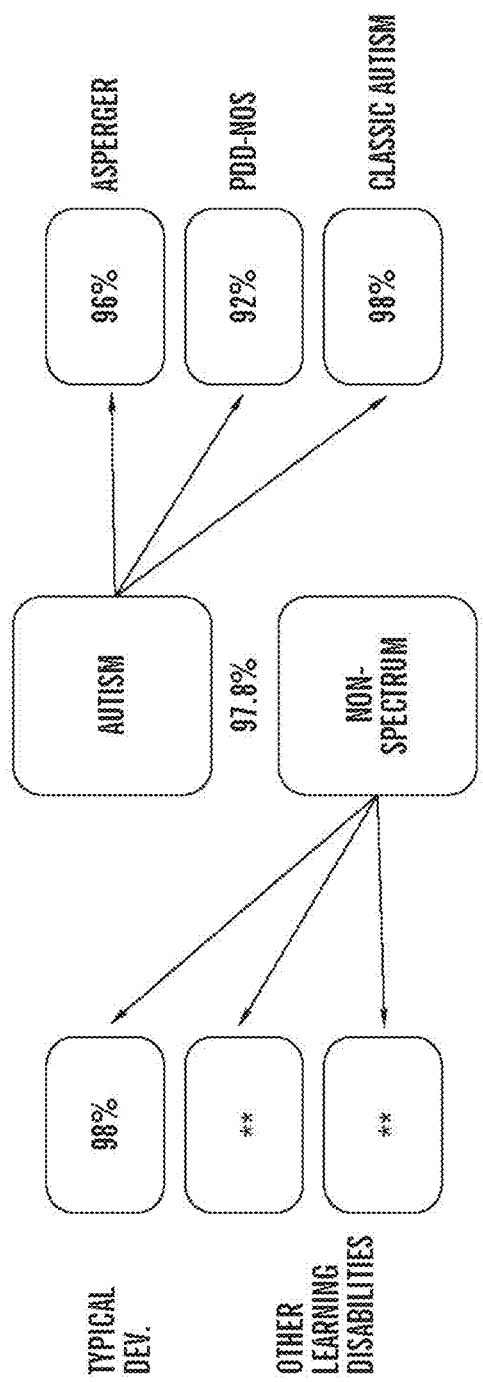
FIG. 11 displays survey results.
Figure 12:
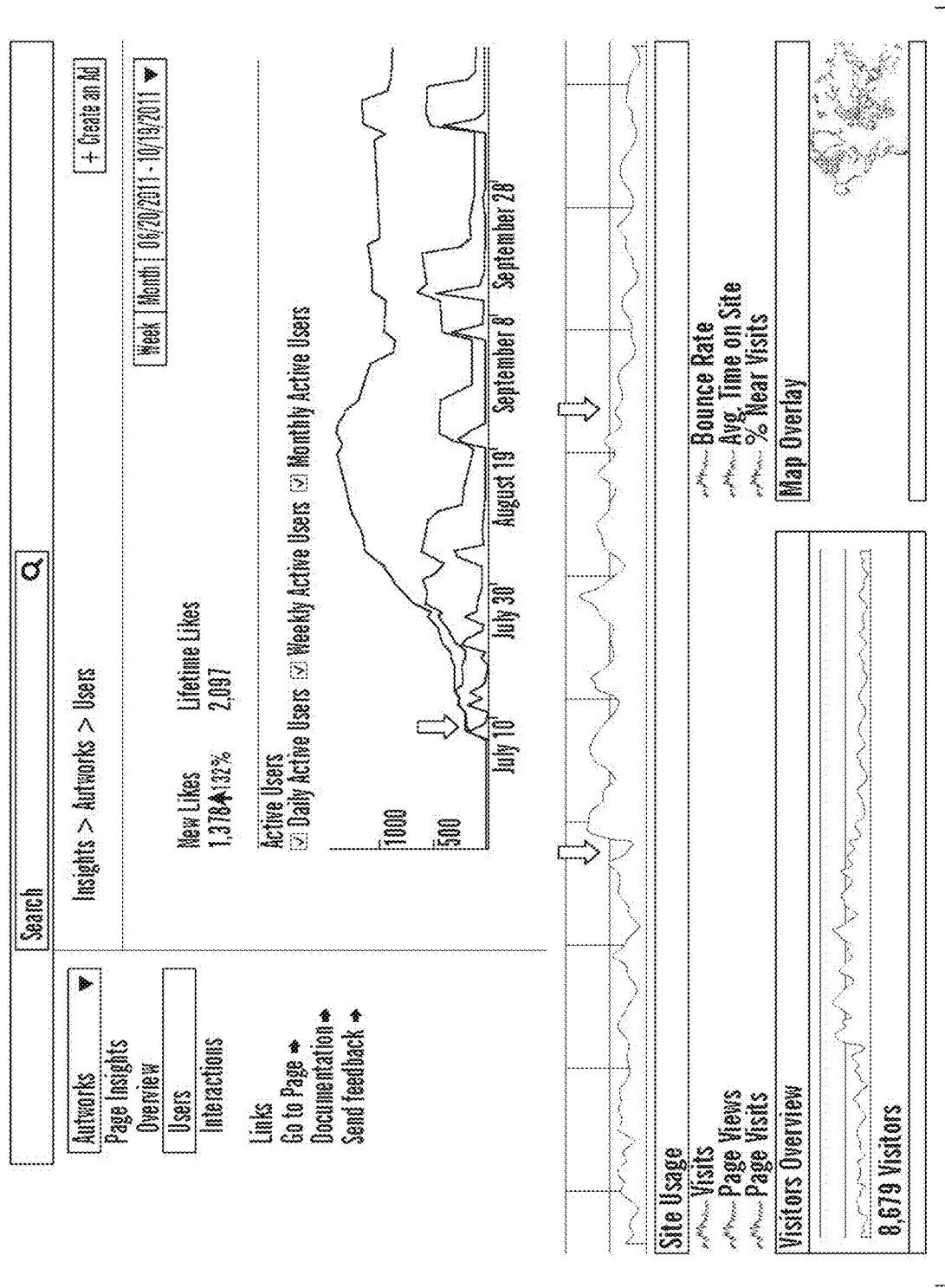
FIG. 12 shows an example of a diagnostics screen from a social network.

Over 2,000 individuals participated in less than 3 months. FIG. 11 shows the results of the trial period. Each participant completed the survey in minutes demonstrating rapid uptake and scalability.

Figure 13:
FIG. 13 is a photograph of an example of materials used for an ADOS Module.

An example of an existing "gold standard" is the ADOS Module 1 (see FIG. 13). The ADOS Module 1 is used for individuals with limited or no vocabulary, and is therefore useful for younger children. The ADOS consists of 10 activities designed to elicit behaviors associated with 29 questions. The exam takes 30-60 minutes in the clinical environment.

Figure 29:
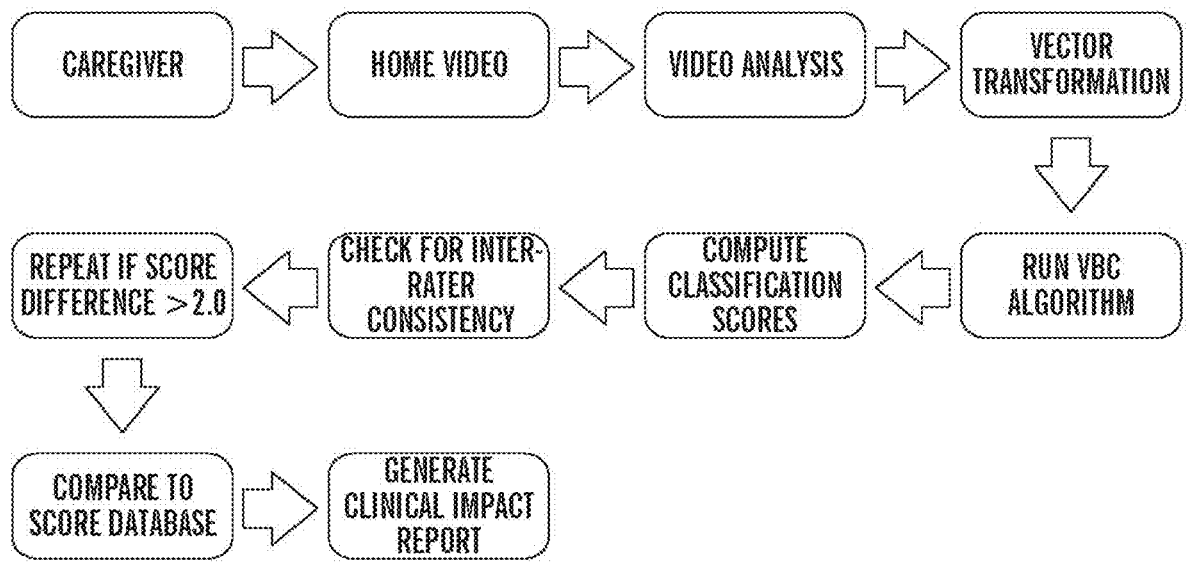
FIG. 29 shows an example of a pipeline for generating a classification score using the video-based classifier (VBC)
Figure 36:
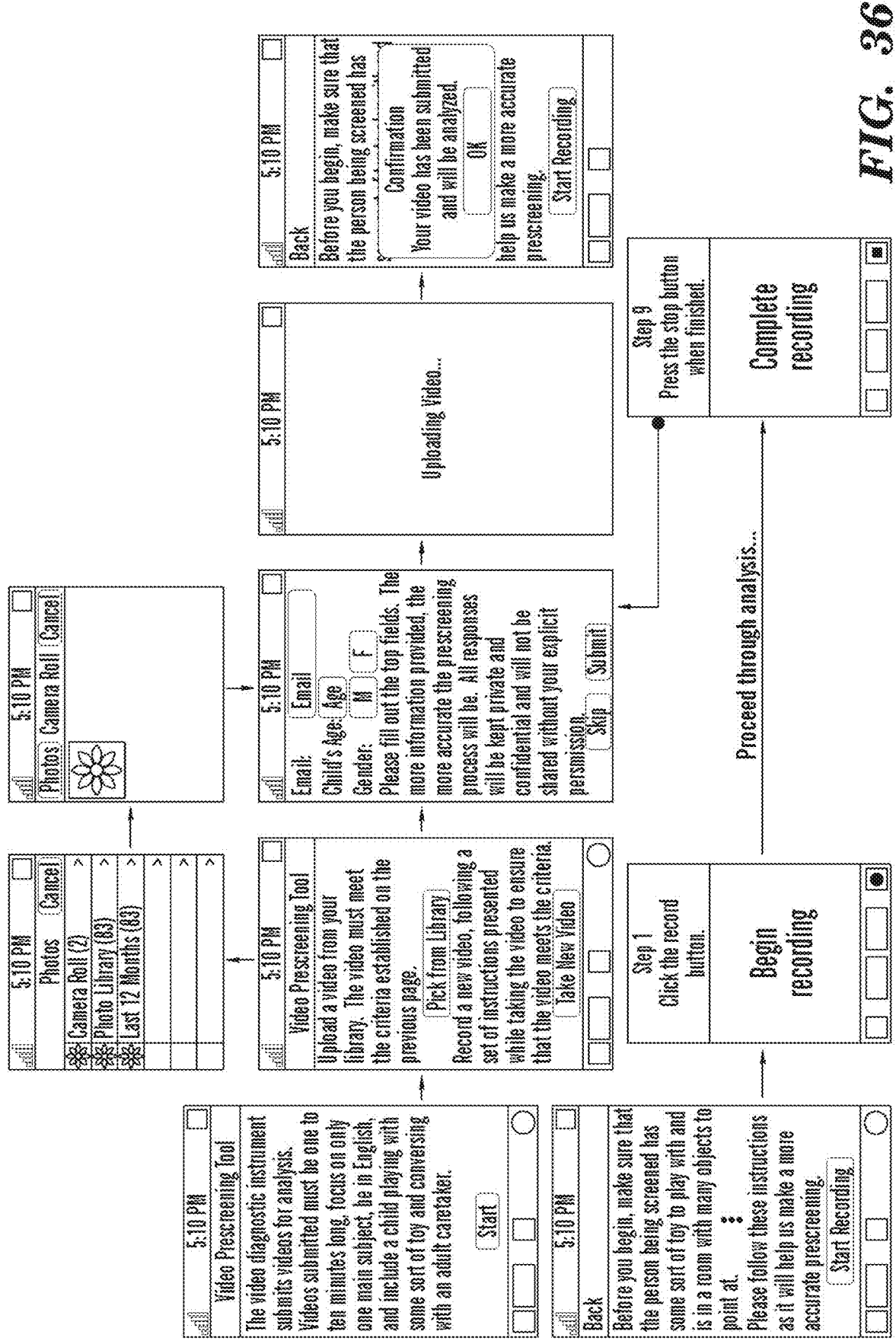
FIG. 36 shows an example of an upload process for a smart device-deployed tool, designed as a machine-specific tool for rapid capture and delivery of home videos suitable for a video-based classifier.

The invention can include a video-based classifier (see FIG. 5, FIG. 29 and FIG. 36). The video based classifier includes eight questions, which is 72% shorter than ADOS. One item focuses on language and communication, that is, A2: Frequency of Vocalization Directed to Others. Five items focus on social interactions, that is, B1: Unusual Eye Contact, B2: Responsive Social Smile; B5: Shared Enjoyment in Interaction; B9: Showing and B10: Spontaneous Initiation of Joint Attention. Two items involve how a child or subject plays with objects, that is, C1: Functional Play with Objects, and C2: Imagination/Creativity.

An example of the validation and coverage of ADI-R, which was modified according to the present invention, is shown, for example, in FIG. 6. Here, there were only two misclassifications, both of which represent marginal scores, and both were classified as non spectrum by ADI-R.

The ADI-R includes 29 questions in the following categories:
A1 Overall Level of Non-Echoed Language
A2 Frequency of Vocalization Directed to Others
A3 Intonation of Vocalizations or Verbalizations
A4 Immediate Echolalia
A5 Stereotyped/Idiosyncratic Use of Words or Phrases
A6 Use of Other's Body to Communicate
A7 Pointing
A8 Gestures
B1 Unusual Eye Contact
B2 Responsive Social Smile
B3 Facial Expressions Directed to Others
B4 Integration of Gaze and other behaviors during social overtures
B5 Shared Enjoyment in Interaction
B6 Response to Name
B7 Requesting
B8 Giving
B9 Showing
B10 Spontaneous Initiation of Joint Attention
B11 Response to Joint Attention
B12 Quality of Social Overtures
C1 Functional Play
C2 Imagination/Creativity
D1 Unusual Sensory Interest in Play Material/Person
D2 Hand and Finger and Other Complex Mannerisms
D3 Self-Injurious Behavior
D4 Unusually Repetitive Interests or Stereotyped Behaviors
E1 Over-activity
E2 Tantrums, Aggression, Negative or Disruptive Behavior
E3 Anxiety Module 1 Activities include the following:
Free Play
Response to name
Response to joint attention
Bubble play
Anticipation of a routine with objects
Responsive social smile
Anticipation of a social routine
Functional and symbolic imitation
Birthday party
Snack The present system and method reduces the number of activities and presents a potential for further reduction in activities with refinement. The present system and method can be reordered to improve efficiency. The present system and method can be adapted to provide simple parameters for home videos.

Figure 14:
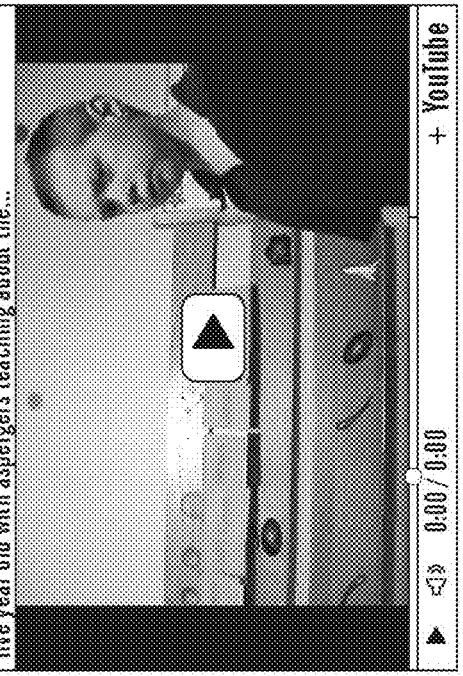
FIG. 14 shows an example of an introduction screen for The Autworks Video Project at Harvard Medical School.

For example, a screenshot from the Autworks Video Project at Harvard Medical School is shown in FIG. 14. In this example, a display is provided with descriptive text, an example of a video, a link to "See Our Videos," a link to "Share Your Video" and a link to "Learn More" about the process.

Figure 15:
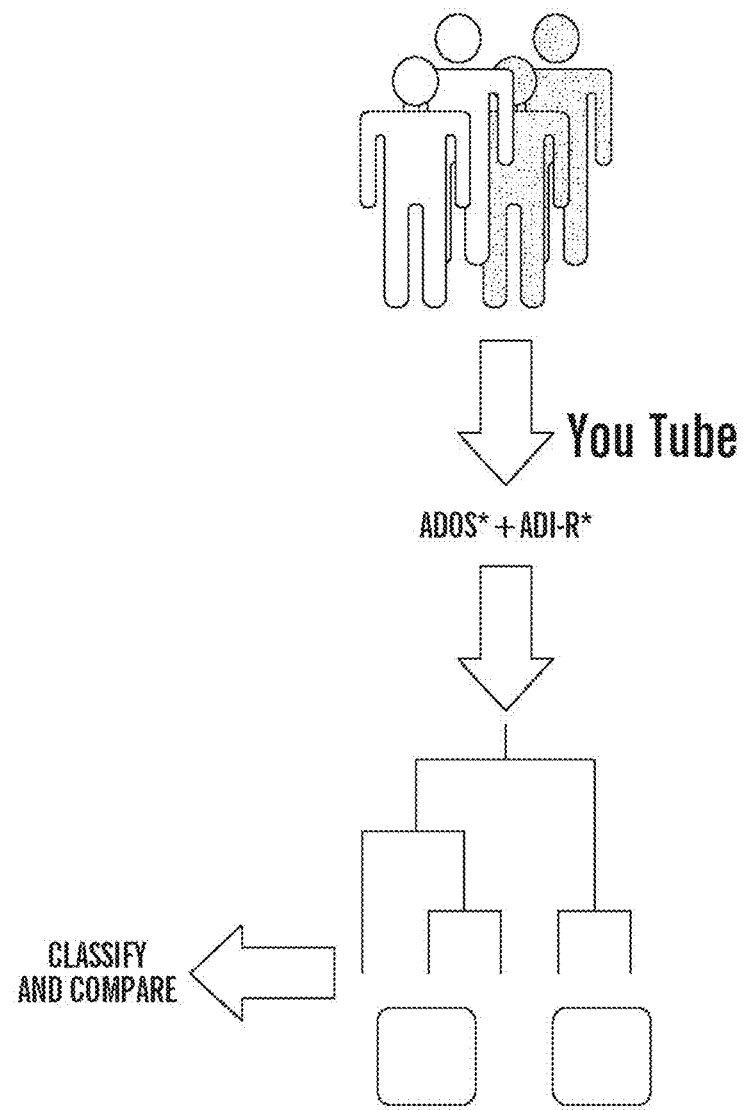
FIG. 15 is a flow chart associated with a video screening method.

A proof of concept for the video screening tool is shown, for example, in FIG. 15. The test included 8 analysts (basic training) and 100 YouTube video, which were 2-5 minutes in length and were home-style and of variable quality. The videos were scored by the analysts using a version of ADI-R, which was modified according to the present invention, and a version of ADOS, which was modified according to the present invention. The results were assessed for accuracy and inter-rater reliability.

Figure 16:
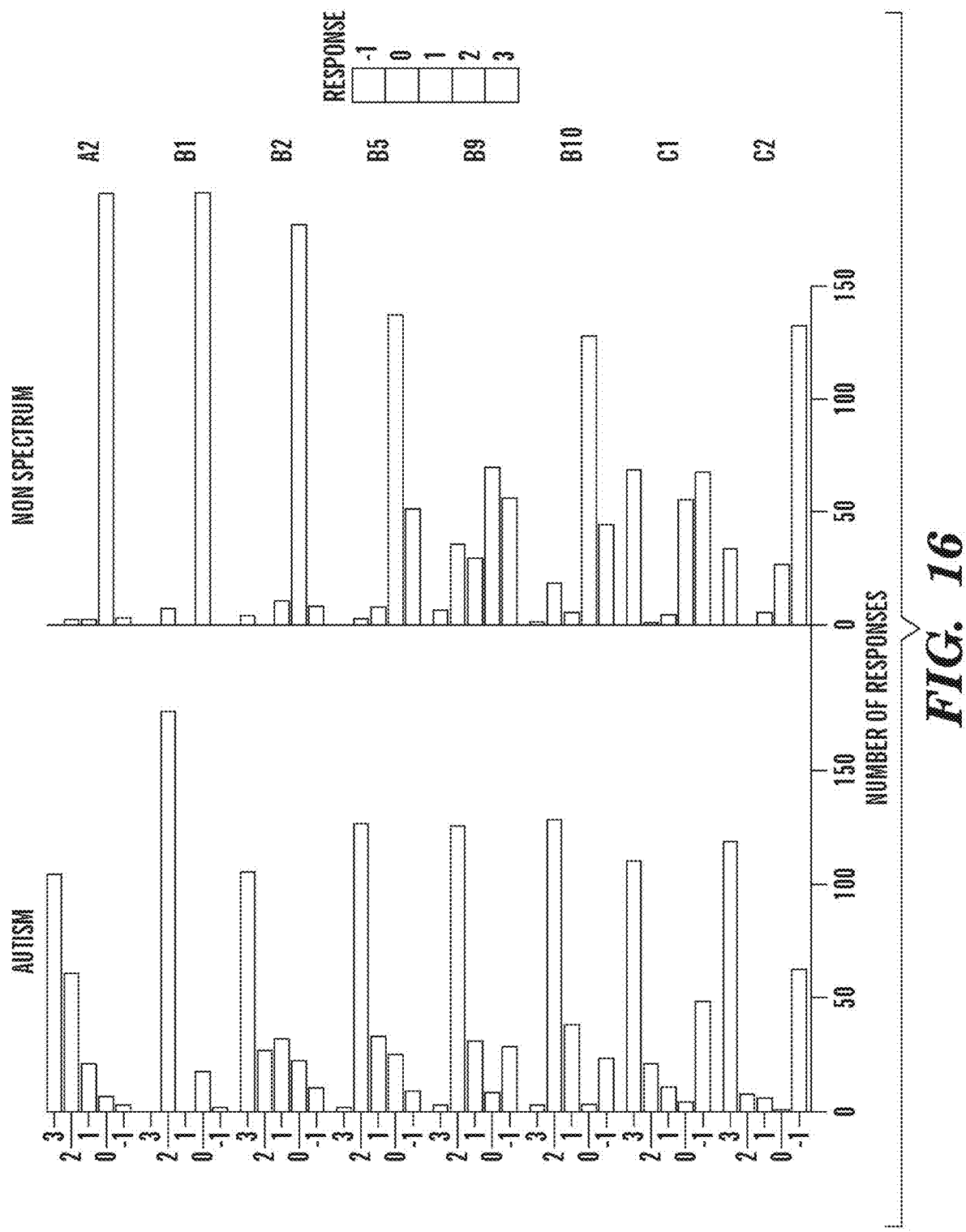
FIG. 16 is a chart demonstrating high inter-rater reliability.
Figure 17:
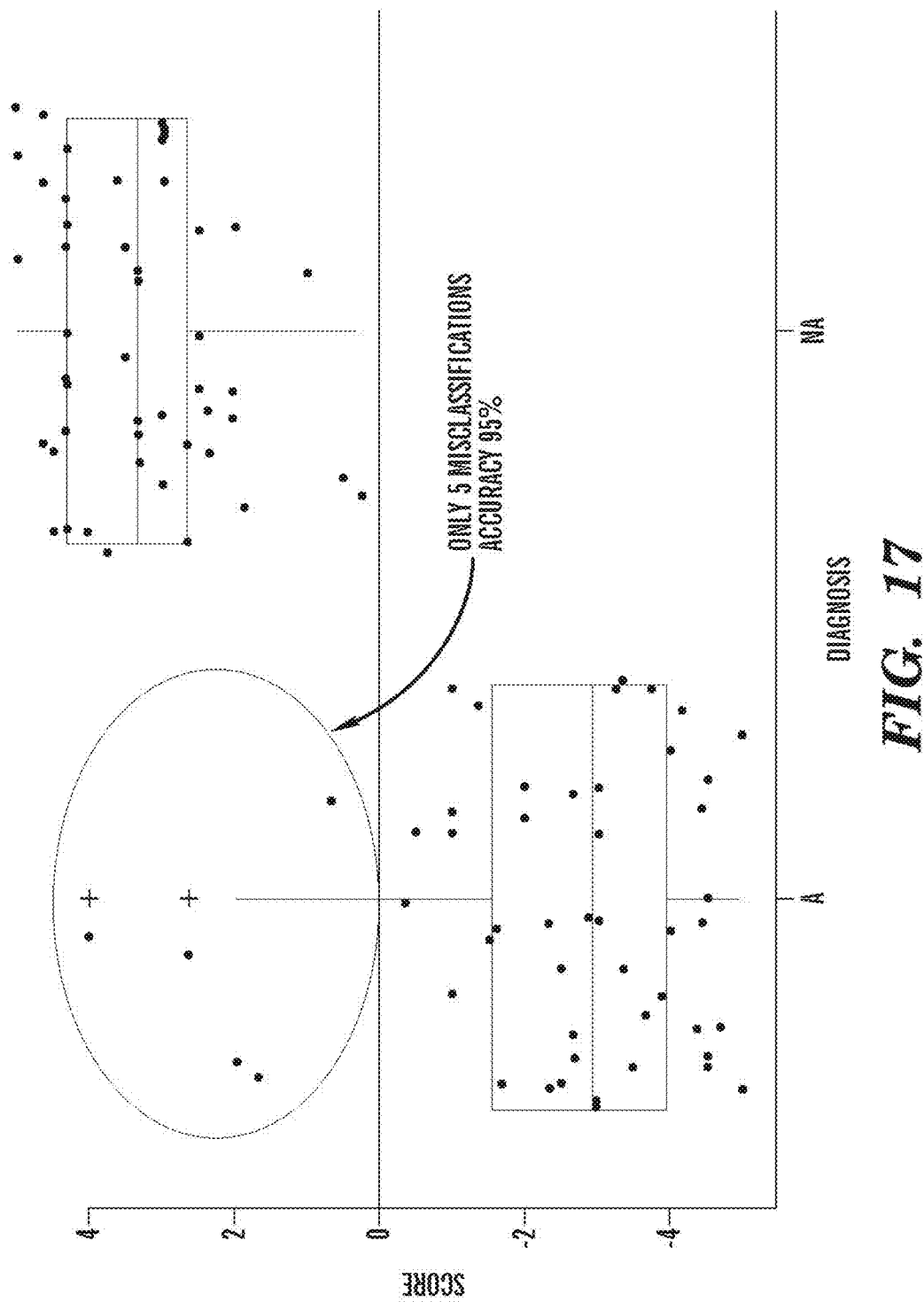
FIG. 17 is a chart demonstrating the combination of inter-rater results for maximum performance.

The inter-rater reliability for the 8 analysts was shown to be high (see FIG. 16). By combining the inter-rater results, maximum performance can be achieved as shown, for example, in FIG. 17. In the proof of concept, there were only five misclassifications, representing an accuracy of 95%.

Figure 18:
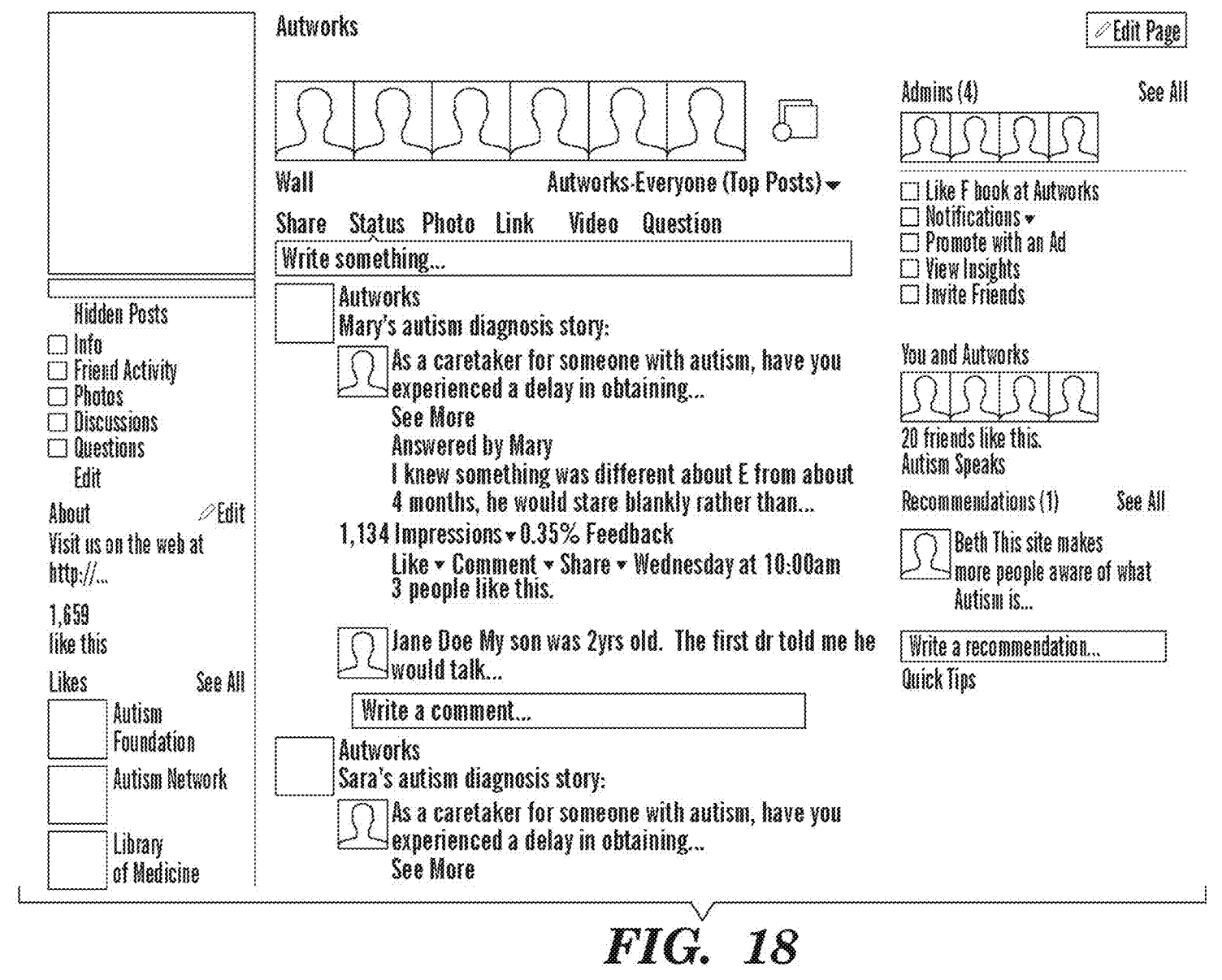
Figure 19:
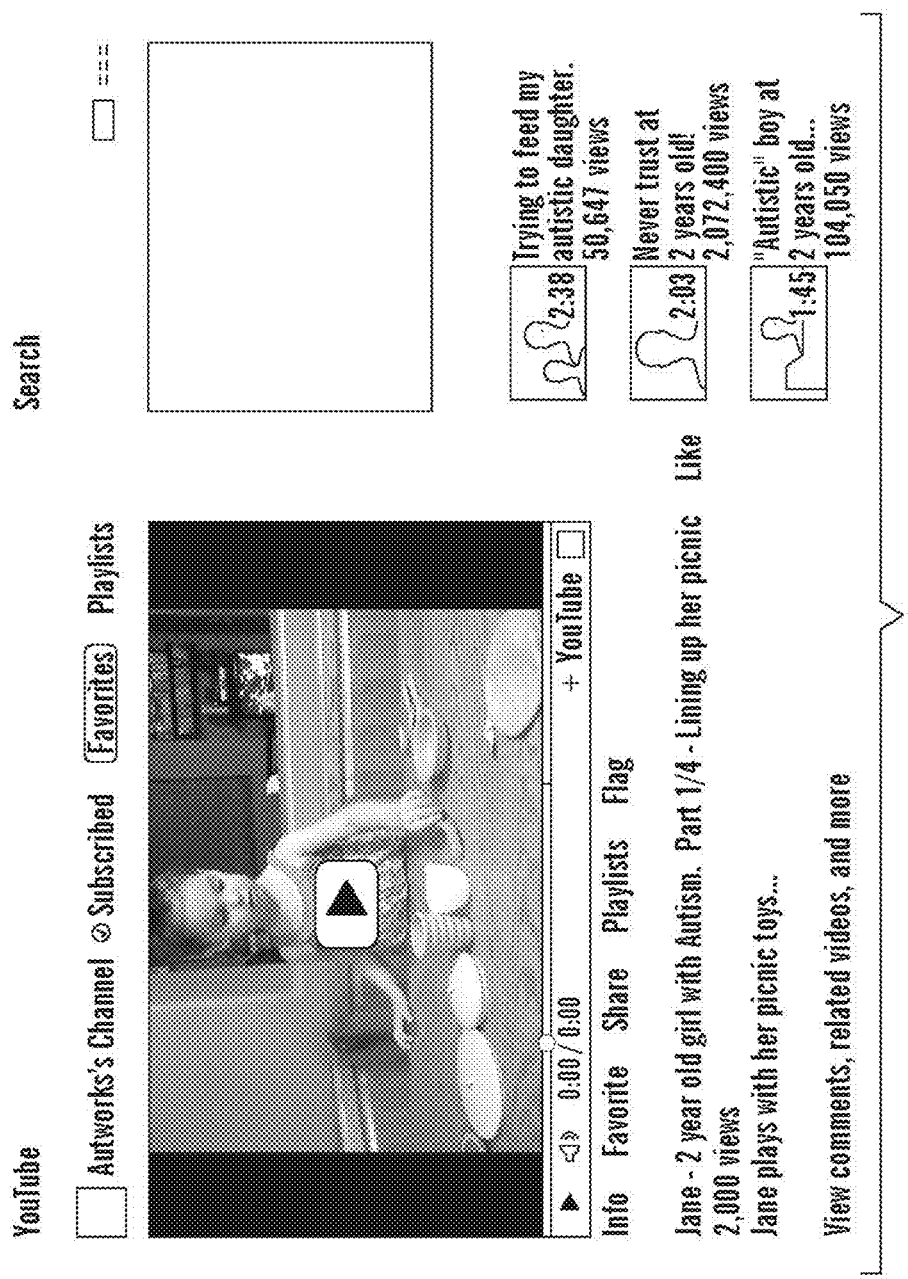
FIG. 19 shows an example of the use of YouTube with the present invention.

Communities can be built using social networking tools such as Facebook, as shown, for example, in FIG. 18. Also, videos can be shared and evaluated through use of a common website such as YouTube. For example, the Autworks YouTube Channel is shown in FIG. 19. Video-based clinical assistance includes the following steps: (1) clinician adds patient to online system; (2) caregiver of patient provides information; (3) analyst scores video; and (4) clinician receives score report and is able to provide a preliminary assessment.

A pre-portal workflow process can include the following steps: (1) caregiver calls clinic to make appointment; (2) clinician creates patient profile on online system; and (3) system sends email notification and instructions to caregiver.

Figure 20:
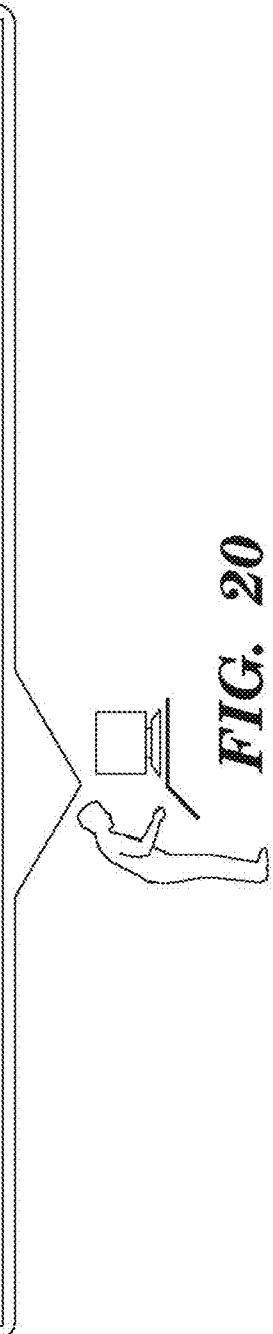
FIG. 20 shows an example of a parent and care provider portal.
Figure 21:
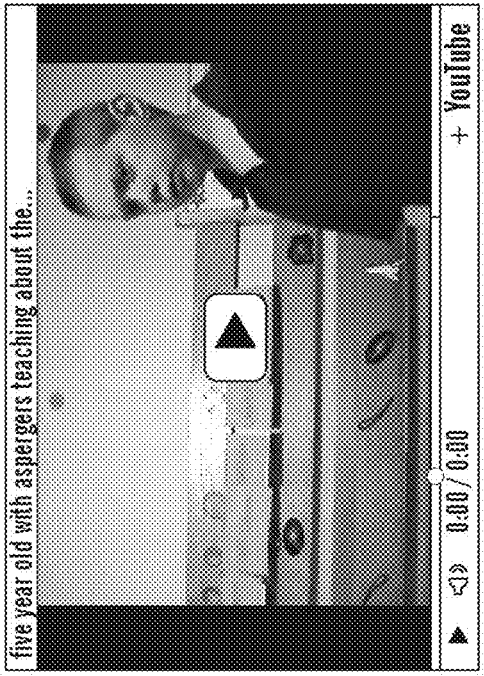
FIG. 21 shows an example of a portal that prompts the user for home video.
Figure 22:
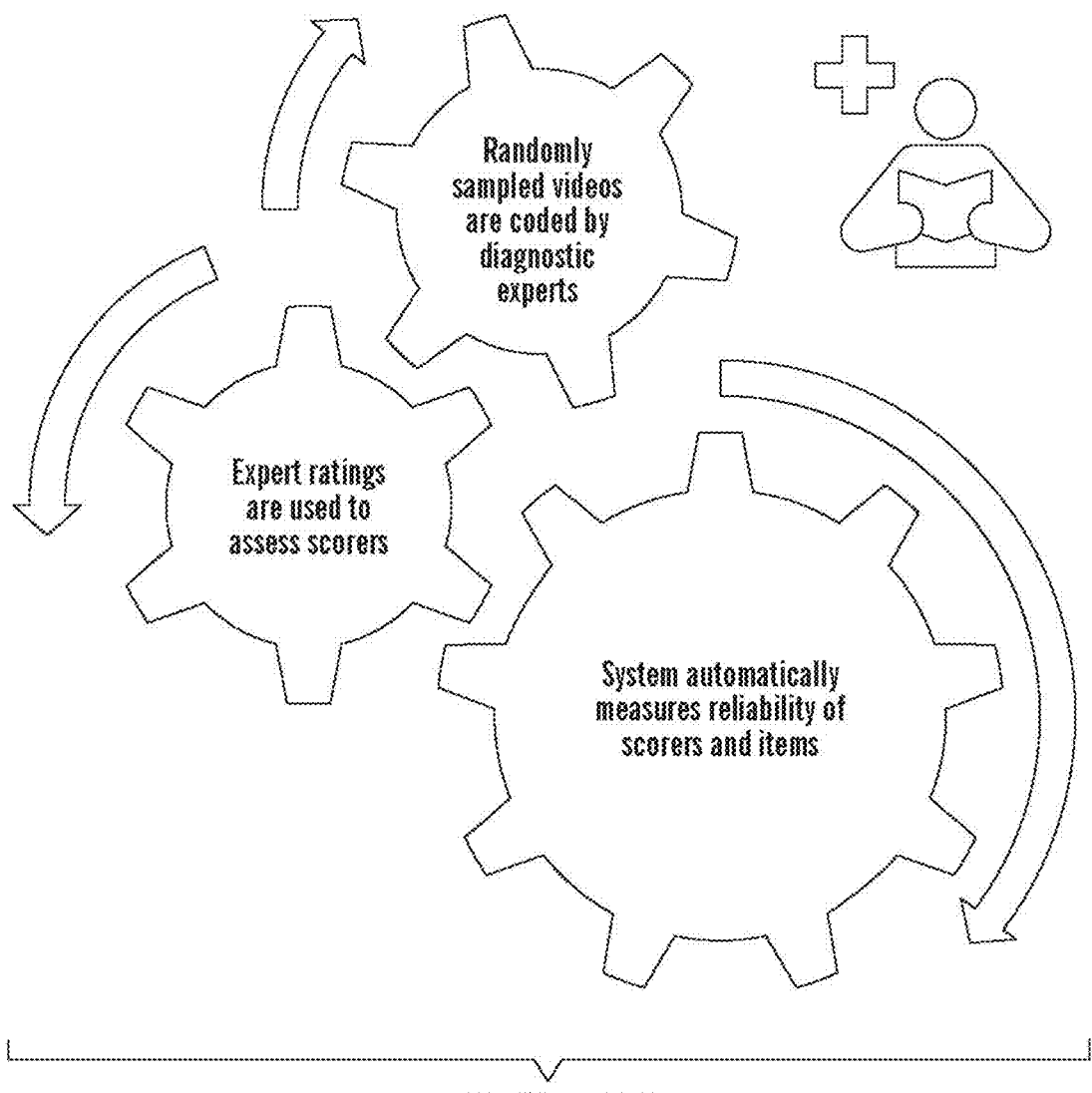
FIG. 22 shows an example of workflow associated with a video screening method.

An example of a parent and care provider portal is shown, for example, in FIG. 20. The portal can prompt the user for a home video as shown, for example, in FIG. 21. An example of the video screening workflow is shown, for example, in FIG. 22, where members of a scoring team watch a video and code answers based on subject behavior. Each scorer receives clinical training. Each expert has clinically administered the ADOS. Randomly sampled videos are coded by diagnostic experts. Expert ratings are used to assess scorers. The system automatically measures reliability of scorers and items. For example, an example of a "Watch and Score Home Videos" system is shown, for example, in FIG. 23.

Figure 24:
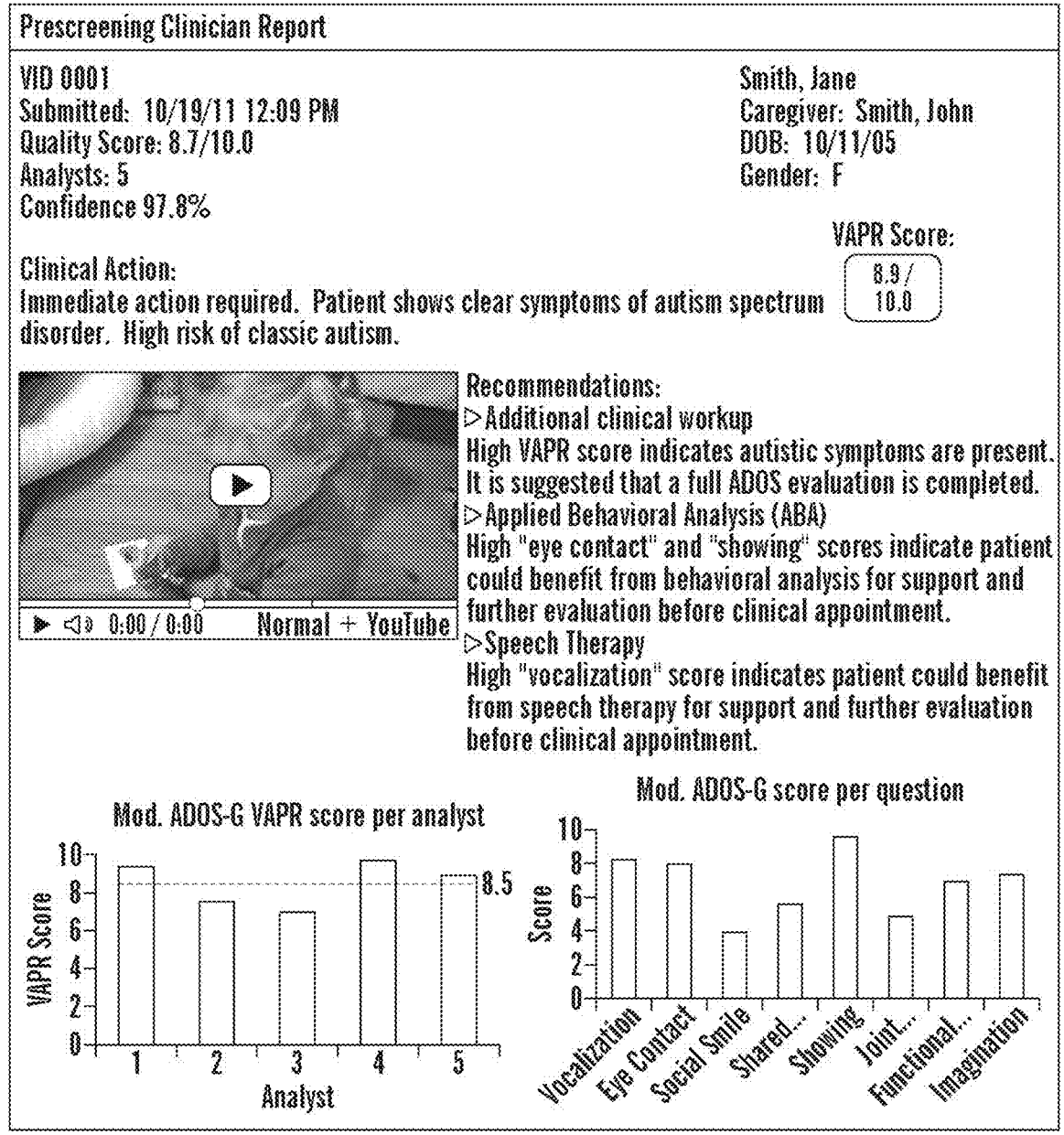
FIG. 24 shows an example of a Prescreening Clinician Report.

An example of a Prescreening Clinician Report is shown in FIG. 24 and includes the following data:

VID 0001
Submitted: 10/19/11 12:09 PM
Quality Score: 8.7/10.0
Analysts: 5
Confidence 97.8%
Wilson, Kate
Caregiver: Wilson, James
DOB: 09/02/06
Gender: F
Clinical Action: Immediate action required. Patient shows clear symptoms of autism spectrum disorder. High risk of classic autism.
VAPR Score: 8.9/10.0
Recommendations:
  i. Full ADOS
    1. High VAPR score indicates autistic symptoms are present. It is suggested that a clinical workup is completed.
  ii. Applied Behavioral Analysis (ABA)
    1. High "eye contact" and "showing" scores indicate patient could benefit from behavioral analysis for support and further evaluation before clinical appointment.
  iii. Speech Therapy
    1. High "vocalization" score indicates patient could benefit from speech therapy for support and further evaluation before clinical appointment.
Video-Based classifier score per analyst
Video-Based classifier score per question
DISCLAIMER: The information contained herein is based on information provided by the patient and/or others, and no attempt has been made to ascertain its accuracy. The material contained herein is for informational purposes only and is not intended to provide medical advice, diagnoses, or suggestions for treatment. We do not warrant that the information is complete, accurate, current or reliable or that it will be suitable for your needs. Under no circumstances, shall anyone else involve in creating or maintaining this information be liable for any direct, indirect, incidental, special or consequential damages, or lost profits that result from the use of this information.
Clinician: Dr. Robert Allen, M.D.

Figure 25:
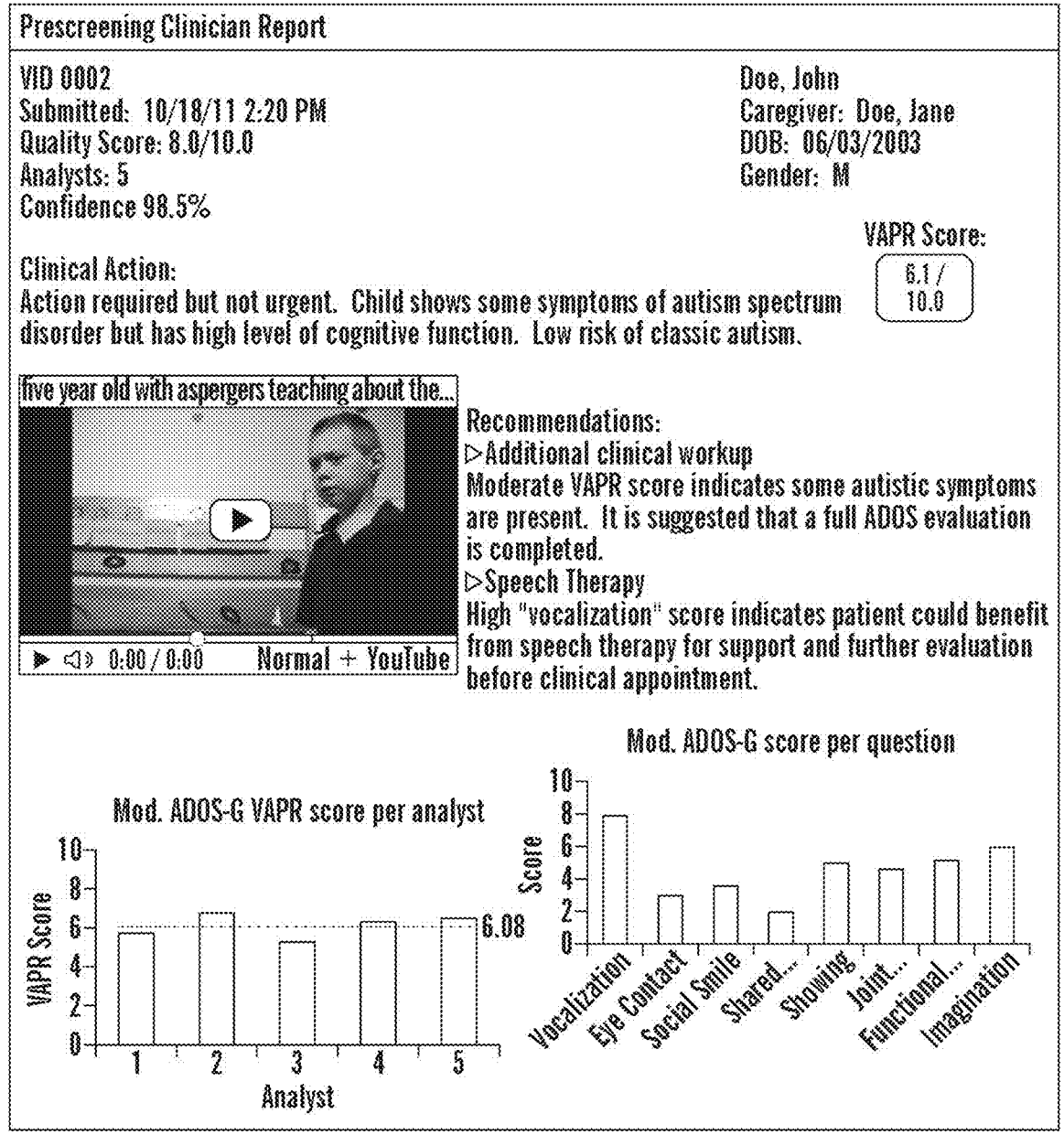
FIG. 25 is another example of a Prescreening Clinician Report.

An example of a Prescreening Clinician Report is shown in FIG. 25 and includes the following data:

VID 0002
Submitted: 10/18/11 2:20 PM
Quality Score: 8.0/10.0
Analysts: 5
Confidence 98.5%
Smith, Jeremy
Caregiver: Smith, Susan
DOB: 05/23/04
Gender: M
Clinical Action: Action required but not urgent. Child shows some symptoms of autism spectrum disorder but has high level of cognitive function. Low risk of classic autism.
VAPR Score: 6.1/10.0
Recommendations:
  i. Clinical workup
    1. Moderate VAPR score indicates some autistic symptoms are present. It is suggested that a clinical workup is conducted.
  ii. Speech Therapy
    1. High "vocalization" score indicates patient could benefit from speech therapy for support and further evaluation before clinical appointment.
Video Classifier score per analyst
Video Classifier score per question
DISCLAIMER: The information contained herein is based on information provided by the patient and/or others, and no attempt has been made to ascertain its accuracy. The material contained herein is for informational purposes only and is not intended to provide medical advice, diagnoses, or suggestions for treatment. We do not warrant that the information is complete, accurate, current or reliable or that it will be suitable for your needs. Under no circumstances, shall anyone else involve in creating or maintaining this information be liable for any direct, indirect, incidental, special or consequential damages, or lost profits that result from the use of this information.
Clinician: Dr. Robert Allen, M.D.

Figure 26:
FIG. 26 shows an example of a Prescreening Caregiver Report.

An example of a Prescreening Caregiver Report is shown in FIG. 26 and includes the following data:

VID 0001
Submitted: 10/18/11 2:20 PM
Smith, Jeremy
Caregiver: Smith, Susan
DOB: 5/23/04
Gender: M
Zip Code: 02421
VAPR Score: 6.1/10.0
Recommendation: Child shows some symptoms of autism spectrum disorder and should be evaluated by a licensed professional. Take patient to a care facility at your earliest convenience.
Video
Map
Facility
Address
Phone
Website
Miles
DISCLAIMER: The information contained herein is based on information provided by the patient and/or others, and no attempt has been made to ascertain it's accuracy. The material contained herein is for informational purposes only and is not intended to provide medical advice, diagnoses, or suggestions for treatment. We do not warrant that the information is complete, accurate, current or reliable or that it will be suitable for your needs. Under no circumstances, shall anyone else involve in creating or maintaining this information be liable for any direct, indirect, incidental, special or consequential damages, or lost profits that result from the use of this information.

Part V: Supporting Data, Experimental Data and Disclosure

Figure 27:
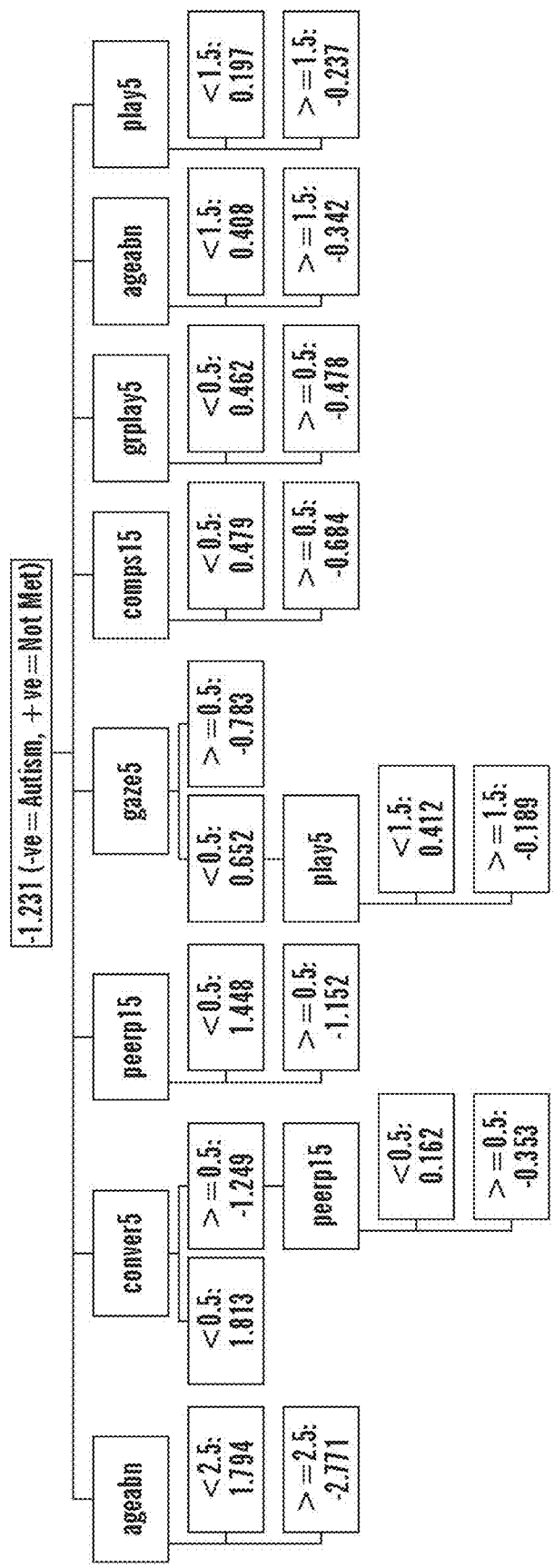
FIG. 27 shows an example of a parent-/caregiver-directed classifier.

FIG. 27 displays an example of a parent-/caregiver-directed classifier according to the invention. FIG. 27 displays the direct outcome of the decision tree learning algorithm used on data from the gold-standard instrument entitled "Autism Diagnostic Instrument-Revised" (ADI-R).

The decision tree learning algorithm can be applied to the answers to the complete set of questions found on the ADI-R (N=93) and the diagnostic outcome, Autism Spectrum Disorder (ASD, autism) vs. Not-Met (meant to indicate both neurotypical AND individuals with developmental delays or neurological impairments that are not ASD). The application of the decision tree learning algorithm results in a dramatic reduction in the number of questions required to achieve the below depicted 100% sensitive and 99% specific classifier. Each node in the decision tree represents one of the 7 questions, where each question represents a behavior or behavioral class deemed to be (by the machine learning processes of the invention) highly discerning in the recognition of ASD/autism. Three of the questions appear twice in the tree (ageabn, peerp15, play5). The 7 questions and their answers are provided in Example 1.

The input to the caregiver-directed classifier is a set of answers from a parent or caregiver of a child in his or her direct care, or about whom he or she is intimately familiar. The answer are numerically encoded from 0-8, where 8 represents "not applicable" or "cannot be answered." These numbers are converted into a vector and used during the execution of the classifier. The encoded answer of each question is evaluated by the algorithm at each node in the tree, and at each node a score is either increased or decreased. The outcome of this classification pipeline/process is a final score ranging between −10.0 and +10.0. A negative score suggests the presence of autism spectrum disorder, and a positive score suggests that the subject does not have all symptoms necessary for an autism diagnosis. The magnitude of the value indicates the severity of the behavior and also the confidence in the classification. Higher positive scores indicate more neurotypical behavior and higher negative scores indicate more severe symptoms of autism spectrum disorders.

Example 1

The 7 questions and answer choices. The answers to these 7 questions become the input to the classifier described in FIG. 27. According to the invention, these questions and the answers are preferably understood and answerable by the parent or caregiver without input or assistance by a clinician and within the framework of a web-based or smart device-based user interface.

1. How well does your child understand spoken language, based on speech alone? (Not including using clues from the surrounding environment) (compsl)

Further Consideration
Can you send her/him into another room to get something like her/his shoes or blanket?
What about your purse or a book?
Could s/he deliver a simple message?
Does s/he understand if you say "no" without gesturing or raising your voice?
How about "yes" or "okay"?
How about names of favorite foods or toys or people in your family?
Do you think s/he understands 10 words? 50?
Answer according to the most abnormal behavior your child has exhibited.
0: in response to a request can place an object, other than something to be used by himself/herself (such as the child's shoes or toy), in a new location in a different room (For example: "Please get the keys and put them on the kitchen table")
1: in response to a request can usually get an object, other than something for herself/himself from a different room ("please get the keys from the kitchen table"), but usually cannot perform a new task with the object such as put it in a new place
2: understands more than 50 words, including names of friends and family, names of action figures and dolls, names of food items, but does not meet criteria for the previous two answers
3: understands fewer than 50 words, but some comprehension of "yes" and "no" and names of a favorite objects, foods, people, and also words within daily routines
4: little or no understanding of words
8:
Not applicable 2. Can your child have a back-and-forth conversation with you? (conver)

Further Consideration
Will s/he say something when engaged in conversation?
Will s/he ever ask you a question or build on what you have said so that the conversation will continue?
Will s/he converse normally on topics that you have introduced? Can s/he also introduce appropriate topics?
1: conversation flows, with your child and another person both contributing to an ongoing dialogue
2: occasional back-and-forth conversation, but limited in flexibility or topics
3: little or no back-and-forth conversation; difficult to build a conversation; your child fails to follow conversation topic; may ask or answer questions but not as part of a dialogue
4: very little spontaneous speech
8:
Not applicable 3. Does your child engage in imaginative or pretend play? (play)

"Pretend Play" Examples
Does s/he play with toy tea sets or dolls or action figures or cars? Does s/he drink the tea/push the car/kiss the stuffed animal?
Has s/he ever given the doll a drink or the action figure a ride in the car?
Has s/he ever used the doll/action figure to initiate actions, so that the doll pours and serves the tea or the action figure walks to the car and gets in it? Does s/he ever talk to her/his dolls or animals?
Does s/he ever make them talk or make noises?
Has s/he ever made up a sort of story or sequence?
Further Consideration:
Does this type of play vary from day to day?
Answer according to the most abnormal behavior your child has exhibited. For children 10 years old or older, answer according to how the child played between the ages of 4 and 5.
0: variety of pretend play, including use of toys to engage in play activity
1: some pretend play, including pretending with toys, but limited in variety or frequency
2: occasional pretending or highly repetitive pretend play, or only play that has been taught by others
3: no pretend play
8:
Not Applicable 4. Does your child play pretend games when with a peer? Do they understand each other when playing? (peerpl)

Further Consideration

Does s/he ever take the lead in the play activity? Or does s/he mostly follow the other person's ideas?

Answer according to the most abnormal behavior your child has exhibited. For children 10 years or older, answer according to how she played between ages 4 and 5.

0: imaginative, cooperative play with other children in which your child leads and follows another child in pretend activities 1: some participation in pretend play with another child, but not truly back-and-forth, or level of pretending/imagination is limited in variety 2: some play with other children, but little or no pretending 3: no play with other children or no pretend play even on own

8:

Not Applicable

5. Does your child maintain normal eye contact for his or her age in different situations and with a variety of different people? (gaze)

Further Consideration

Does s/he sometimes watch you walk into the room?

Does s/he look back and forth to your face as other children would? What about with others?

(What is the most abnormal behavior your child has exhibited?)

0: normal eye contact used to communicate across a range of situations and people 1: makes normal eye contact, but briefly or inconsistently during social interactions 2: uncertain/occasional direct gaze, or eye contact rarely used during social interactions 3: unusual or odd use of eye contact

8:

Not Applicable

6. Does your child play with his or her peers when in a group of at least two others? (grplay)

Further Consideration

Is s/he different with children or others outside your immediate family?

Does s/he play cooperatively in games that need some participation such as musical games, hide-and-seek, or ball games?

Would s/he initiate such games? Or actively seek to join in?

Can s/he take different parts in these games (like being chased or doing the chasing, or hiding and looking for the other person?)

What is the most abnormal behavior your child has exhibited? For children 10 or older, please answer according to how the child behaved between the ages of 4 and 5.

0: actively seeks and plays cooperatively in several different groups (three or more people) in a variety of activities or situations 1: some play with peers, but tends not to initiate, or tends to be inflexible in the games played 2: enjoys "parallel" active play (such as jumping in turn on a trampoline or falling down during "ring around the rosie"), but little or no cooperative play 3: seeks no play that involves participation in groups of other children, though may chase or play catch

8:

Not Applicable

7. When were your child's behavioral abnormalities first evident? (ageabn)

Further Consideration

What was her/his play like? What toys did s/he play with? Any pretend games?

How was her/his talking then?

What about looking after herself/himself? Feeding? Toileting? Dressing?

What were her/his relationships with other children like?

0: development in the first 3 years of life clearly normal in quality and within normal limits for social, language, and physical milestones; no behavioral problems that might indicate developmental delay 1: development potentially normal during first 3 years, but uncertainty because of some differences in behavior or level of skills in comparison to children of the same age 2: development probably abnormal by the age of 3 years, as indicated by developmental delay, but milder and not a significant departure from normal development 3: development definitely abnormal in the first 3 years, but not obvious as autism 4: development definitely abnormal in the first 3 years and quality of behavior, social relationships, and communications appear to match behaviors consistent with autism Example 2

The present invention includes a python function to implement the caregiver-directed classifier represented in FIG. 27 given answers to all (or a majority (at least 4)) of the questions listed in Example 1. An example of code of the python function is provided in Appendix 1.

Figure 28:
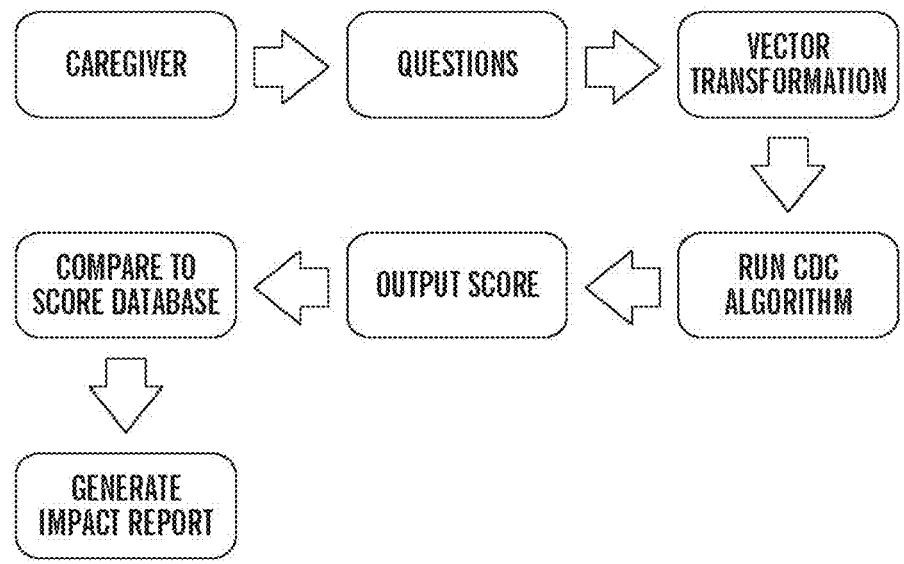
FIG. 28 shows an example of a pipeline for generating a classification score using the caregiver-directed classifier (CDC)

FIG. 28 is a pipeline for generating a classification score using the caregiver-directed classifier (CDC). A caregiver interacts with a system (website, smart device application, etc.) to answer the questions according to the invention (Example 1), the answers to these questions are transformed into a discrete numerical vector and delivered as input to the CDC (FIG. 27) to generate a score that is then plotted within a distribution of scores to create a preliminary impact report that can be used in the process of diagnosis a person with (or without) Autism Spectrum Disorder.

An example of workflow for the CDC is shown in FIG. 38. The CDC can have the following steps: a caregiver answers a questionnaire using a web enabled device; answers to the questionnaire are converted into a numerical vector; the vector is imported into an analytical system for scoring; a CDC algorithm (such as that shown, for example, in FIG. 2) is run natively within the analytical system; and a score and disorder classification are computed.

FIG. 5 shows an example of the video-based classifier (VBC). FIG. 5 displays the direct outcome of the decision tree learning algorithm used on data from the gold-standard instrument entitled "Autism Diagnostic Observation Schedule" (ADOS). The invention can apply the decision tree learning algorithm to the answers to the complete set of questions found on the ADOS-G Module 1 (N=29) and the diagnostic outcome, Autism Spectrum Disorder (ASD, autism) vs. Not-Met (meant to indicate both neurotypical AND individuals with developmental delays or neurological impairments that are not ASD). The application of the decision tree learning algorithm results in a dramatic reduction in the number of questions to a total of 8 given the tree classification algorithm depicted below. The answers to these 8 questions when run through the below depicted classifier of the present invention yield a classification outcome (ASD or non-ASD) that is 100% sensitive and 99% specific. Each node in the decision tree represents one of the 8 questions, where each question represents a behavior or behavioral class deemed to be (by the machine learning processes of the invention) highly discerning in the recognition of ASD/autism. Two of the questions appear twice in the tree (B9 and B10). The 8 questions and their answers are provided in Example 3.

Example 3

The 8 questions and their answer choices. The answers to these 8 questions become the input to the classifier described in FIG. 5. According to the invention, these questions and the answers are preferably understood and answerable by a video analyst (trained by the training materials according to the invention) without input or assistance by a clinician. The questions were also designed to be readily answered via examination of the subject in a short (2-15 minute) video and within the framework of a web-based or smart device-based user interface. However, the questions could be answered via other means of observation, including direct observation of the child.

A2: Frequency of Vocalization Directed to Others

This item is coded for the amount of socially-directed vocalization

0=Directs vocalizations to caregiver or other individuals in the video in a variety of contexts. Must include chatting or vocalizing to be friendly or to express interest, and/or to make needs known.

1=Directs vocalizations to caregiver or other individuals in the video regularly in one context, or directs vocalizations to caregiver or other individuals in the video irregularly across a variety of situations/contexts.

2=Occasionally vocalizes to caregiver or other individuals in the video inconsistently in a limited number of contexts. May include whining or crying due to frustration.

3=Almost never vocalizes or vocalizations never appear to be directed to caregiver or other individuals in the video.

8=Not Applicable

B1: Unusual Eye Contact

Coding for this item requires that clear, flexible, socially modulated, and appropriate gaze that is used for a variety of purposes be distinguished from gaze that is limited in flexibility, appropriateness, or contexts. This can occur at any point during the video (For example, if the subject's use of eye contact varies but at one point in the video it is clear that the individual uses appropriate gaze, score as 0).

0=Appropriate gaze with subtle changes meshed with other communication

2=Uses poorly modulated eye contact to initiate, terminate, or regulate social interaction.

8=Not applicable

B2: Responsive Social Smile

This item pertains to the child's facial response to a smile and/or playful verbal interaction with the caregiver or other individuals in the video. The child's smile must be in response to another person rather than to an action.

0=Smiles immediately in response to smiles by the caregiver or other individuals in the video. This must be a clear change from not smiling to a smile that is not followed by a specific request (e.g., "Give me a smile!").

1=Delayed or partial smile, or smiles only after repeated smiles by caregiver or other individuals in the video, or smiles only in response to a specific request.

2=Smiles fully or partially at the caregiver or other individuals in the video only after being tickled or touched in some way, or in response to a repeated action with an object (e.g., wagging a Teddy Bear in the air).

3=Does not smile in response to another person.

8=Not Applicable

B5: Shared Enjoyment in Interaction

The rating applies to his/her ability to indicate pleasure at any point throughout the video, not just to interact or respond.

0=Shows definite and appropriate pleasure with the caregiver or other individuals in the video during a couple or more activities.

1=Shows some appropriate pleasure caregiver's or other individuals in the video during more than one activity, OR shows definite pleasure directed to the caregiver or others in the video during one interaction.

2=Shows little or no expressed pleasure in interaction with the caregiver or others in the video. May show pleasure in his/her own actions or with toys.

8=Not Applicable

B9 Showing

Showing is defined as purposely placing an object so that another person can see it. For a score of 0, this must be accompanied by eye contact.

0=Spontaneously shows toys or objects at various times during the video by holding them up or placing them in front of others and using eye contact with or without vocalization 1=Shows toys or objects partially or inconsistently (e.g., holds them up and/or places them in front of others without coordinated eye contact, looks from an object in his/her hands to another person without clearly orienting it toward that person).

2=Does not show objects to another person.

8=Not Applicable

B10: Joint Attention

This rating codes the child's attempts to draw another person's attention to objects that neither of them is touching. This does not include such attempts if they are for the purpose of requesting.

0=Uses clearly integrated eye contact to reference an object that is out of reach by looking at the object, then at the examiner or the parent/caregiver, and then back to the object. Eye contact may be coordinated with pointing and/or vocalization. One clear example of an attempt to draw another person's attention to an object (i.e., more than just referencing) is sufficient for this rating.

1=Partially references an object that is clearly out of reach. May spontaneously look and point to the object and/or vocalize, but does not coordinate either of these with looking at another person, OR may look at an object and then look at or point to the examiner or the parent/caregiver, but not look back at the object.

2=No approximation of spontaneous initiation of joint attention in order to reference an object that is out of reach.

C1: Functional Play with Objects

This item describes appropriate use of toys.

0=Spontaneously plays with a variety of toys in a conventional manner, including appropriate play with several different miniatures (e.g., telephone, truck, dishes, materials at a Birthday Party).

1=Some spontaneous conventional play with toys.

2=Play with toys is limited to one type despite others being available, or play with a toy is imitation rather than genuine interest.

3=No play with toys or only stereotyped play.

8=Not Applicable

C2: Imagination/Creativity

This item describes flexible, creative use of objects.

0=Pretending that a doll or other toy is something else during an imaginative play scenario (e.g., using a block to give a doll a drink).

1=Self initiated Pretend play with a doll (e.g., feeding, hugging, or giving a drink) but within context and not with the creative flexibility represented in the answer above.

2=Imitates pretend play following the lead of a caregiver or other individual(s) in the video, but does not self-initiate pretending.

3=No pretend play.

8=Not Applicable

Example 4

The invention can include a python function to implement the video-based classifier represented in FIG. 5 given answers to all (or at least 4) of the questions listed in Example 3. An example of code of the python function is provided in Appendix 2.

FIG. 29 shows an example of a pipeline for generating a classification score using the video-based classifier (VBC). A caregiver interacts with a system according to the invention (including but not limited to a website and smart device application) to upload a home video from their computer, digital camera, smartphone or other device. The video is then evaluated by video analysts (usually 2 or more for inter-rater reliability and classification accuracy) to answer the questions (Example 3) needed by the classifier (FIG. 5). The answers to these questions are transformed into a discrete numerical vector and delivered as input to the VBC (FIG. 5) to generate a score that is then plotted within a distribution of scores to create a preliminary impact report that can be used in the process of diagnosis a person with (or without) Autism Spectrum Disorder.

An example of workflow for the VBC is shown in FIG. 39. The CDC can have the following steps: acquire a video; encode the video; import the video to an analytical system, wherein the video can be imported for simultaneous viewing and scoring; conduct analysis and scoring of the video, wherein a rating subject with respect to a small number of questions is calculated and wherein the results are converted into a vector of scores; import the scores to the VBC algorithm for scoring (such as that shown, for example, in FIG. 5); and compute a score for the classification.

Figure 30:
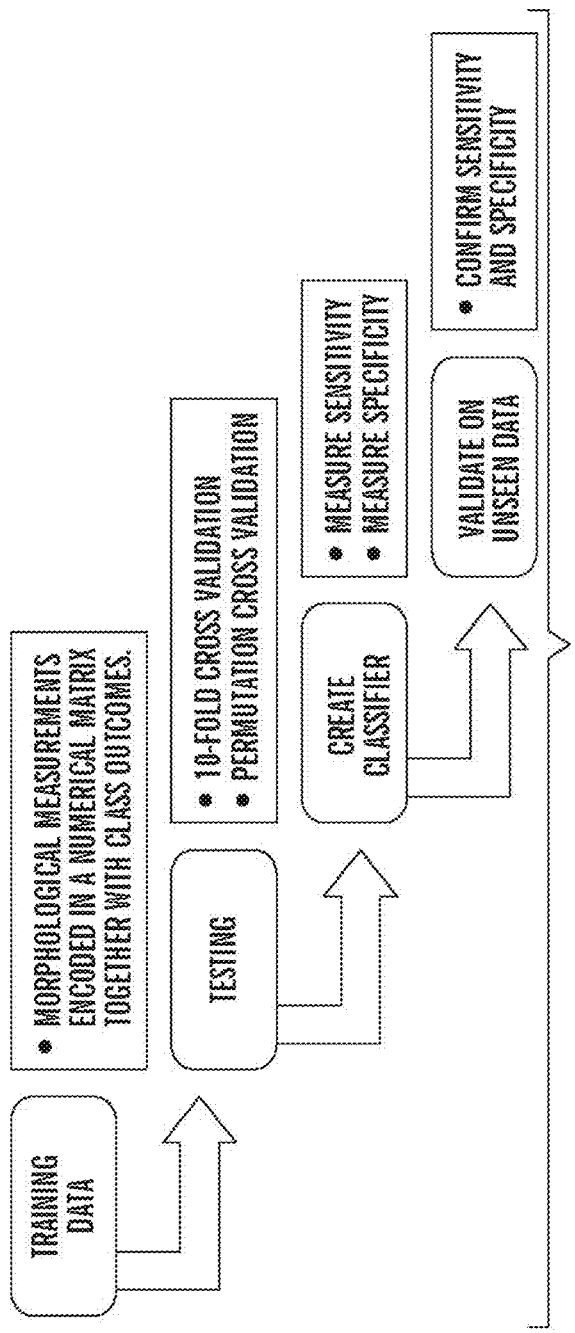
FIG. 30 shows an example of a machine learning classification method for creating Reduced Testing Procedures (RTPs) that can be embedded into mobilized frameworks for rapid testing outside of clinical sites.

FIG. 30 shows an example of a machine learning classification method for creating Reduced Testing Procedures (RTPs) that can be embedded into mobilized frameworks for rapid testing outside of clinical sites. The flow chart below details the process of creating RTPs using a machine learning algorithms on behavioral data designed for the diagnosis of a human condition or disease, such as autism spectrum disorder and ADHD. This classification algorithm creates a mapping from class instances (for example autism spectrum disorder vs. other) to real numbers that is defined in terms of a set of base rules that become summed to generate a real value prediction. The classification of an instance is the sign of the prediction. The numerical value of the prediction indicates confidence in the prediction with low values being less reliable.

Figure 31:
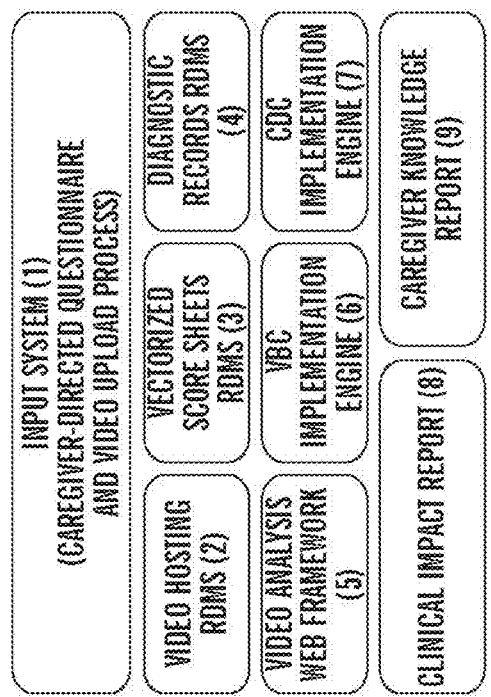
FIG. 31 shows an example of infrastructure for data hosting and report generation using the CDC and VBC.

FIG. 31 shows an example of infrastructure for data hosting and report generation using the CDC and VBC. The input system 1 is a web and smart device (iphone, ipad, etc) framework for registration and data input. The video hosting relational database management system (RDMS) 2 securely stores videos for delivery to the video analytics framework 5 and to the clinical and caregiver medical impact reports 8 and 9. The database layer contains a RDMS for storing the coded answers to both the caregiver questions (Example 1) and the observational questions (Example 3). The web input system 1 automatically encodes the former and the video analytics framework 5 automatically encodes the latter. The internal software layer contains the code needed to execute the video based classifier (VBC) 6 and the caregiver-directed classifier (CDC) 7 given a vector of answers from the vectorized score sheet RDMS 3. The diagnostic records RDMS 4 stores all VBC and CDC scores together with subject age, medical record data, and treatment plans. These data are collated into a clinical impact report 8 and a caregiver knowledge report 9. The questions, encoding, and code for the CDC are given in FIG. 1, Example 1 and Example 2. The questions, encoding, and code for the VBC are given in FIG. 5, Example 3 and Example 4.

More details on the input system (FIG. 32, FIG. 33 and FIG. 34), the video analytics framework (FIG. 35), the clinical impact report (FIG. 24), and the caregiver knowledge report (FIG. 26) are provided below.

FIG. 32, FIG. 33 and FIG. 34 show examples of the input system (Item 1 on FIG. 31).

FIG. 35 shows an example of video analysis web framework.

The above screen shot is backed by a relational database system shown in Table 11. Table 11 displays 31 tables provided in an exemplary MySQL database according to the invention.

TABLE 11 auth_group
auth_group_permissions
auth_message
auth_permission
auth_user
auth_user_groups
auth_user_user_permissions
clinic_analyst
clinic_clinicanswer
clinic_clinician
clinic_clinicquestion
clinic_clinicquestionset
clinic_clinicresponse
clinic_clinicscore
clinic_patient
clinic_video
django_admin_log
django_content_type
django_openid_auth_association
django_openid_auth_nonce
django_openid_auth_useropenid
django_session
django_site
score_answer
score_question
score_questionset
score_response
score_score
score_userprofile
south_migrationhistory
upload_video FIG. 24 shows an example of a clinical impact report. This report contains the scores generated by the VBC and CDC together with inter-rater reliability information on the VBC. The report contains a recommended clinical action, matched to the score. The report also contains a set of treatments likely to be needed by the child based on the severity of the score.

FIG. 26 shows an example of a parent/caregiver-directed knowledge report. This report gives information about the child's severity and makes a connection to the nearest and most appropriate clinical service provider.

Table 12 shows an example of diagnostic records RDMS containing information on the score from the two classifiers, age, additional medical record data, treatment schedule and video file locations.

TABLE 12

| CDC | VBC | AGE | EMR | Treatments | Videos |
|---|---|---|---|---|---|
| −9.43 | −8.7 | 2.1 | Comorbidities, parental diseases, | ABA Behavioral therapy | fdms1, fdms2 |
| −5.43 | −4.5 | 3.3 | Fragile X, Crohn's disease in mother | ABA Behavioral therapy | |
| ... | ... | ... | ... | ... | ... |

Part VI: Smart Device-Deployed Tool

The invention can include a smart device-deployed tool, designed as a machine-specific tool for rapid capture and delivery of home videos suitable for the video-based classifier. In one embodiment, a tool that is compatible with an iPhone, iPad or iTouch includes xCode (Apple's software development environment) classes, xib and storyboard files to create an autism video uploader User Interface.

Examples of code for the smart device-deployed tool are provided in Appendices 3 through 13, inclusive. Specifically, Appendix 3 lists code for "SurveyController.h," Appendix 4 lists code for "VideoTypeViewController.m," Appendix 5 lists code for "VideoTypeViewController.h," Appendix 6 lists code for "VideoInformationScreen.m," Appendix 7 lists code for "VideoInformationScreen.h," Appendix 8 lists code for "CameraInstructionsViewController.m," Appendix 9 lists code for "CameraInstructionsViewController.h," Appendix 10 lists code for "OverlayViewController.m," Appendix 11 lists code for "OverlayViewController.h," Appendix 12 lists code for "VideoInstructionsViewController.m" and Appendix 13 lists code for "VideoInstructionsViewController.h."

An example of a video upload process is shown in FIG. 36. The process can include a first step of prompting the user to start a video prescreening tool, and a second step of prompting the user to pick a video from a library (such as a video in a Camera Roll, where an iPhone, iPad or iTouch is used as the input device) or take a new video. If the user elects to take a new video, the user is given suggestions or instructions, prompted to start recording and guided through a multi-step analytical process, which may, in one embodiment, include 9 steps. Upon completion of the recording, the user can be returned to the third step in the process. The process can include a third step of prompting the user to enter an email address, the child's age and the gender of the child. The process can include a fourth step of uploading the video; and a fifth step of displaying a confirmation to the user.

The invention can also include a virtual machine to enable the video-based and parent/caregiver based classification of individuals suspected of autism. This machine can include a unix operating system, a webserver, Django framework and a MySQL relational database to store information about the users and videos. This machine enables a user to enter a portal authenticated via Django's built-in user authentication system (usernames and passwords are stored in a hashed table in the MySQL database). It then enables this authenticated user to provide detailed information on medical history, and to answer the questions associated with the caregiver-classifier. Next this machine can contain all necessary functionality for a user to upload video to an access-controlled directory in its original format. The machine contains the transcoding components including FFmpeg needed to transcode the video into .webm and .mp4 formats. The machine contains and automatically runs code to store details about the video files, including their locations within the file system and metatags.

This machine also contains the tools needed for an analyst to score a video and compute the video-based classifier. An analyst can securely login to the machine and be presented with a list of videos available for review sorted in order of priority. Finally the machine contains code and software connections needed to generate a report for both a clinical consumer as well as a caregiver consumer.

The present invention can be used to develop a pre-screening tool for general public use by individuals who are concerned about a particular disorder but not willing, ready or able to see a professional for a formal assessment and diagnosis or as a pre-screening tool in any environment, be it clinical or non-clinical. The invention can be applied to any disorder, particularly disorders that are diagnosed using screening techniques that may include lengthy and time-consuming questionnaires and/or observations of behavior to develop a pre-screening technique for the disorder. The present invention can be applied to any disorder that has a behavioral component, that manifests itself in behavior, that manifests itself in the motion or movement of a subject, that manifests itself in an observable manner or that manifests itself in a morphological attribute of the subject.

For example, the invention can be applied in the manner described herein to any mental disorder such as acute stress disorder, adjustment disorder, amnesia, anxiety disorder, anorexia nervosa, antisocial personality disorder, asperger syndrome, attention deficit/hyperactivity disorder, autism, autophagia, avoidant personality disorder, bereavement, bestiality, bibliomania, binge eating disorder, bipolar disorder, body dysmorphic disorder, borderline personality disorder, brief psychotic disorder, bulimia nervosa, childhood disintegrative disorder, circadian rhythm sleep disorder, conduct disorder, conversion disorder, cyclothymia, delirium, delusional disorder, dementia, dependent personality disorder, depersonalization disorder, depression, disorder of written expression, dissociative fugue, dissociative identity disorder, down syndrome, dyslexia, dyspareunia, dyspraxia, dysthymic disorder, erotomania, encopresis, enuresis, exhibitionism, expressive language disorder, factitious disorder, folie a deux, ganser syndrome, gender identity disorder, generalized anxiety disorder, general adaptation syndrome, histrionic personality disorder, hyperactivity disorder, primary hypersomnia, hypochondriasis, hyperkinetic syndrome, hysteria, intermittent explosive disorder, joubert syndrome, kleptomania, mania, munchausen syndrome, mathematics disorder, narcissistic personality disorder, narcolepsy, nightmares, obsessive-compulsive disorder, obsessive-compulsive personality disorder, oneirophrenia, oppositional defiant disorder, pain disorder, panic attacks, panic disorder, paranoid personality disorder, parasomnia, pathological gambling, perfectionism, pervasive developmental disorder, pica, postpartum depression, post-traumatic embitterment disorder, post-traumatic stress disorder, primary insomnia, psychotic disorder, pyromania, reading disorder, reactive attachment disorder, retts disorder, rumination syndrome, schizoaffective disorder, schizoid, schizophrenia, schizophreniform disorder, schizotypal personality disorder, seasonal affective disorder, self injury, separation anxiety disorder, sadism and masochism, shared psychotic disorder, sleep disorder, sleep terror disorder, sleepwalking disorder, social anxiety disorder, somatization disorder, stereotypic movement disorder, stuttering, suicide, tourette syndrome, transient tic disorder, trichotillomania and the like.

Figure 37:
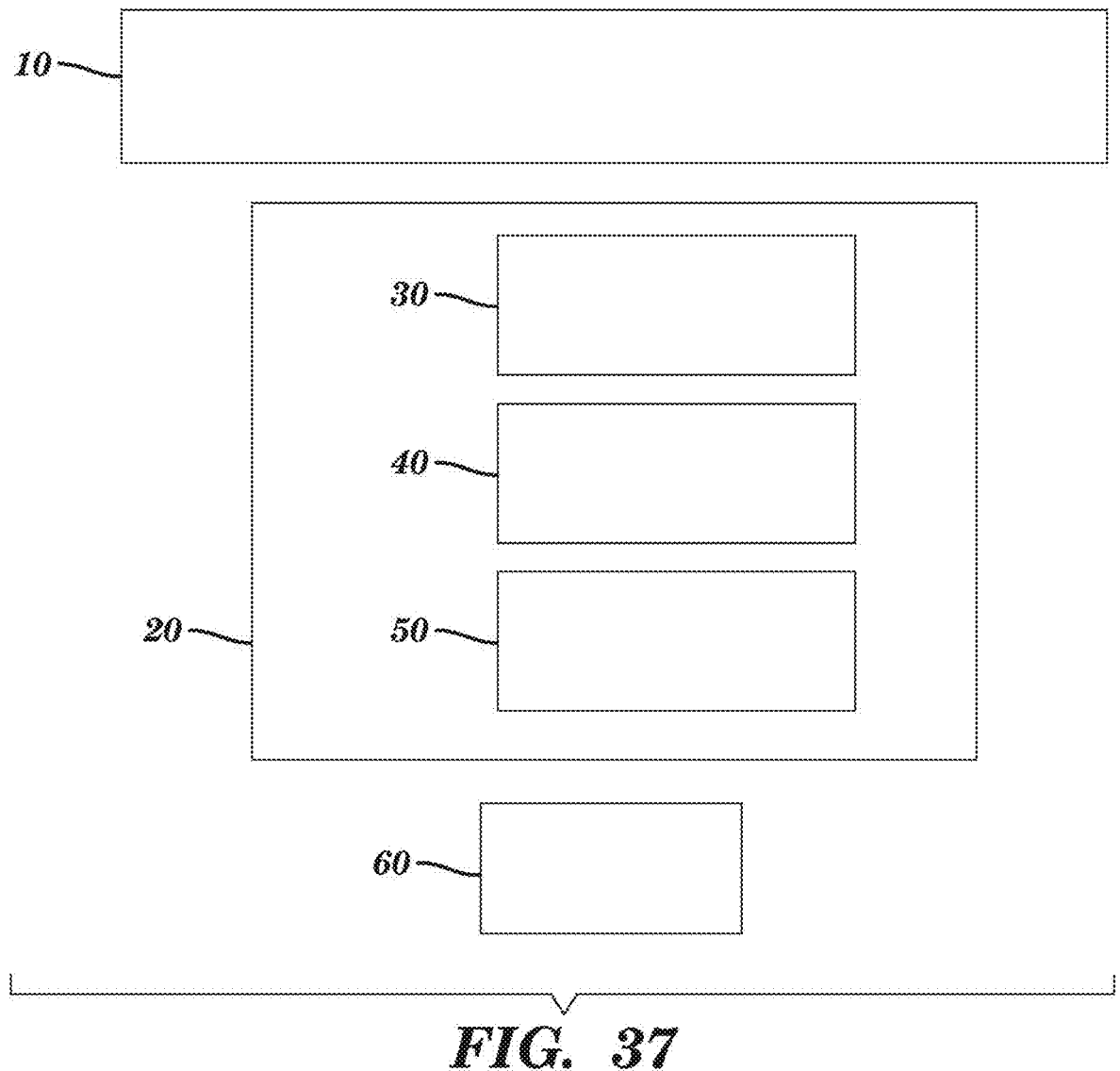
FIG. 37 is a block diagram including an instrument, a diagnostic tool, a computer system, a processor, a memory and a computer program.

As shown, for example, in FIG. 37, the present invention can include a computer implemented method of generating a diagnostic tool 60 of an instrument for diagnosis of a disorder 10, wherein the instrument comprises a full set of diagnostic items. The computer implemented method can comprise on a computer system 20 having one or more processors 30 and a memory 40 storing one or more computer programs 50 for execution by the one or more processors 30, the one or more computer programs 50 including instructions for implementing the method, described in detail herein. The present invention can also include a non-transitory computer-readable storage medium storing the one or more computer programs 50, which, can, in turn, be installed on the computer system 20.

In the present application, each client can include a client application. The client can be any number of devices (e.g., computer, internet kiosk, personal digital assistant, cell phone, gaming device, desktop computer, laptop computer, tablet computer, a television with one or more processors embedded therein or attached thereto, or a set-top box) which can be used to connect to a communication network. The communication network can be a wireless, optical, wired or other type of network that facilitates the passage of information. It can include the Internet, one or more local area networks (LANs), one or more wide area networks (WANs), other types networks, or a combination of such networks. The client application is an application that is executed by the client (e.g., browser, e-mail client, word processor) and that displays or presents information to a user of the client (the client application can also perform other tasks not relevant to the present discussion). Client can also include a location determiner for reporting a geolocation of the client.

A customer client system can include one or more processing units (CPU's), one or more network or other communications interfaces, memory, and one or more communication buses for interconnecting these components. The customer client system can include a user interface, for instance a display and a keyboard. The memory can include high speed random access memory and can also include non-volatile memory, such as one or more magnetic or optical storage disks. The memory can include mass storage that is remotely located from CPU's. The memory can store the following elements, or a subset or superset of such elements: an operating system that includes procedures for handling various basic system services and for performing hardware dependent tasks; a network communication module (or instructions) that is used for connecting the customer client system to other computers via the one or more communications interfaces (wired or wireless), such as the Internet, other wide area networks, local area networks, metropolitan area networks, and so on; a client application as described above; a client assistant as described above; optionally, a cache of downloaded and a cache downloaded, as well as other information for viewing using the client application, and information retrieved by user selection of one or more items.

Although some of various drawings illustrate a number of logical stages in a particular order, stages which are not order dependent can be reordered and other stages can be combined or broken out. Alternative orderings and groupings, whether described above or not, can be appropriate or obvious to those of ordinary skill in the art of computer science. Moreover, it should be recognized that the stages could be implemented in hardware, firmware, software or any combination thereof.

The present invention is not to be limited in scope by the specific embodiments described herein. Indeed, various modifications of the present invention, in addition to those described herein, will be apparent to those of ordinary skill in the art from the foregoing description and accompanying drawings. Thus, such modifications are intended to fall within the scope of the invention. Furthermore, many functions described herein can be implemented in hardware or in software. Further, software descriptions of the invention can be used to produce hardware implementing the invention. Software can be embodied on any known non-transitory computer-readable medium having embodied therein a computer program for storing data. In the context of this document, a computer-readable storage medium can be any tangible medium that can contain, or store a program for use by or in connection with an instruction execution system, apparatus, or device. A computer-readable storage medium can be, for example, an electronic, magnetic, optical, electromagnetic, infrared, or semiconductor system, apparatus, or device, or any suitable combination of the foregoing. More specific examples of the computer-readable storage medium include the following: a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. Further, although aspects of the present invention have been described herein in the context of a particular implementation in a particular environment for a particular purpose, those of ordinary skill in the art will recognize that its usefulness is not limited thereto and that the present invention can be beneficially implemented in any number of environments for any number of purposes.

The foregoing description, for purpose of explanation, has been described with reference to specific embodiments. However, the illustrative discussions above are not intended to be exhaustive or to be limiting to the precise forms disclosed. Many modifications and variations are possible in view of the above teachings. The embodiments were chosen and described in order to best explain the principles of the aspects and its practical applications, to thereby enable others skilled in the art to best utilize the aspects and various embodiments with various modifications as are suited to the particular use contemplated.

The invention claimed is:

1. A computer-implemented method for evaluating and treating a subject for a behavioral disorder, a developmental delay, or a neurological impairment, said method comprising:
   (a) receiving, by at least one computing device, an input comprising items obtained without requiring assistance by a clinician;
   (b) providing, by the at least one computing device, the input to a prediction algorithm based on at least one machine learning model that is trained with data from a plurality of individuals having the behavioral disorder, the developmental delay, or the neurological impairment, wherein the prediction algorithm is configured to evaluate the subject with respect to a presence or absence of the behavioral disorder, the developmental delay, or the neurological impairment based on the input;
   (c) determining, by the at least one computing device, an evaluation result comprising an indication that the behavioral disorder, the developmental delay, or the neurological impairment is present in said subject using the prediction algorithm; and (d) providing, by the at least one computing device, treatment to the subject for the behavioral disorder, the developmental delay, or the neurological impairment based on the evaluation result.

2. The method of claim 1, wherein the treatment is based on a severity of the behavioral disorder, the developmental delay, or the neurological impairment.

3. The method of claim 1, wherein the treatment comprises at least one of applied behavioral analysis (ABA) or a speech therapy.

4. The method of claim 1, further comprising determining a treatment plan for treating the subject based on the evaluation result.

5. The method of claim 1, further comprising scoring the subject based on the evaluation result, wherein said score is indicative of a likelihood of a presence or an absence of the behavioral disorder, the developmental delay, or the neurological impairment in said subject.

6. The method of claim 5, wherein the final score comprises a magnitude, and wherein the magnitude of the final score is indicative of one or more of a severity of the behavioral disorder, the developmental delay, or the neurological impairment or a confidence in the evaluation result.

7. The method of claim 1, further comprising transforming the input into discrete numerical vectors, and wherein the discrete numerical vectors are provided to the classifier to determine the evaluation result.

8. The method of claim 1, wherein the at least one computing device comprises a mobile computing device.

9. The method of claim 8, wherein the mobile computing device is a smart device.

10. The method of claim 9, wherein the smart device is a smart phone or a tablet.

11. The method of claim 1, wherein the input comprises a video of the subject.

12. The method of claim 1, wherein the prediction algorithm comprises a classifier generated using a machine learning technique selected from the group consisting of ADTree, BFTree, DecisionStump, FT, J48, J48graft, Jrip, LADTree, LMT, Nnge, OneR, PART, RandomTree, REPTree, Ridor and SimpleCart.

13. The method of claim 1, wherein the prediction algorithm is configured to evaluate a statistically accurate set of items as the input to allow efficient evaluation.

14. The method of claim 1, wherein the evaluation result is based on the Autism Diagnostic Instrument-Revised or the Autism Diagnostic Observation Schedule.

15. The method of claim 1, wherein the behavioral disorder, the developmental delay, or the neurological impairment comprises ADHD, autism, or autism spectrum disorder.

16. The method of claim 1, wherein the prediction algorithm is configured to generate the evaluation result with a statistical accuracy of at least about 90%.

17. A computing system for evaluating and treating a subject for a behavioral disorder, a developmental delay, or a neurological impairment, said computing system comprising:

a processor;
a prediction algorithm based on at least one machine learning model that is trained with data from a plurality of individuals having the behavioral disorder, the developmental delay, or the neurological impairment, wherein the prediction algorithm is configured to evaluate the subject with respect to a presence or absence of the behavioral disorder, the developmental delay, or the neurological impairment based on an input comprising items obtained without requiring assistance from a clinician; and
a non-transitory computer readable medium that stores instructions that when executed by the processor, causes the processor to:
receive, using the computing system, the input comprising items obtained without requiring assistance from a clinician, wherein the input is related to the behavioral disorder, the developmental delay, or the neurological impairment;
provide, by the computing system, the input to the prediction algorithm;
determine, by the computing system, an evaluation result comprising an indication that the behavioral disorder, the developmental delay, or the neurological impairment is present in said subject using the prediction algorithm; and
provide, by the computing system, a treatment to the subject for the behavioral disorder, the developmental delay, or the neurological impairment based on the evaluation result.

18. The system of claim 17, wherein the behavioral disorder, the developmental delay, or the neurological impairment comprises ADHD, autism, or autism spectrum disorder.

19. The system of claim 17, wherein the treatment comprises at least one of applied behavioral analysis (ABA) or a speech therapy.

20. The system of claim 17, wherein the treatment comprises a treatment plan for treating the subject based on the evaluation result.

* * * * *